US009951339B2

(12) United States Patent
De Lange et al.

(10) Patent No.: US 9,951,339 B2
(45) Date of Patent: Apr. 24, 2018

(54) CELL MODIFICATION METHOD USING ESSENTIAL GENES AS MARKERS AND OPTIONALLY RECYCLING THESE

(71) Applicant: DSM IP ASSETS B.V., Heerlen (NL)

(72) Inventors: Ilse De Lange, Echt (NL); Bernard Meijrink, Echt (NL); Johannes Andries Roubos, Echt (NL); Siew-loon Ooi, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 14/427,698

(22) PCT Filed: Sep. 19, 2013

(86) PCT No.: PCT/EP2013/069532
§ 371 (c)(1),
(2) Date: Mar. 12, 2015

(87) PCT Pub. No.: WO2014/044782
PCT Pub. Date: Mar. 27, 2014

(65) Prior Publication Data

US 2015/0225728 A1 Aug. 13, 2015

(30) Foreign Application Priority Data

Sep. 19, 2012 (EP) .................................... 12185052

(51) Int. Cl.
*C12N 15/65* (2006.01)
*C12N 15/80* (2006.01)
*C12N 15/81* (2006.01)

(52) U.S. Cl.
CPC ............. *C12N 15/65* (2013.01); *C12N 15/80* (2013.01); *C12N 15/81* (2013.01)

(58) Field of Classification Search
None
See application file for complete search history.

(56) References Cited

FOREIGN PATENT DOCUMENTS

| | | | |
|---|---|---|---|
| CN | 101784666 | A | 7/2010 |
| WO | 0200907 | A1 | 1/2002 |

OTHER PUBLICATIONS

International Search Report from corresponding PCT/EP2013/069532, dated Dec. 6, 2013, 3 pages.
Johansson et al., "Multiple Gene Expression by Chromosomal Integration and Cre-Loxp-Mediated Marker Recycling in *Saccharomyces cerevisiae*", Methods in Molecular Biology, Humana Press Inc., NJ, vol. 267, Jan. 1, 2004, pp. 287-296, XP009072375.
Peubez et al., "Antibiotic-free selection in *E. coli*: new considerations for optimal design and improved production", Microbial Cell Factories, Biomed Central, London, NL, vol. 9, No. 1, Sep. 7, 2010, pp. 1475-2859, XP021077213.
Goh et al., "Plasmid selection in *Escherichia coli* using an endogenous essential gene marker", BMC Biotechnology, Biomed Central Ltd. London, GB, vol. 8, No. 1, Aug. 11, 2008, pp. 1472-6750, XP021043258.
Prade, Rolf A. et al., "Genomics of Plants and Fungi", 2003, pp. 180-184.
Zhang, Ren et al., "DEG 5.0, a database of essential genes in both prokaryotes and eukaryotes", Nucleic Acids Research, 2009, vol. 37, pp. D455-D458.
Hu, Wenqi et al., "Essential Gene Identification and Drug Target Prioritization in Aspergillus fumigatus", PLoS Pathogens, Mar. 2007, vol. 3, No. 3, pp. 0001-0015.
Juhas, Mario et al., "Essence of life: essential genese of minimal genomes", Cell Press, Oct. 2011, vol. 21, No. 10, pp. 562-568.
Firon, Arnaud et al., "Identifying essential genes in fungal pathogens of humans", Trends in Microbiology, Oct. 2002, vol. 10, No. 10, pp. 456-462.

*Primary Examiner* — Channing S Mahatan
(74) *Attorney, Agent, or Firm* — McBee Moore Woodward & Vanik IP, LLC; Susan McBee; Chester Moore

(57) ABSTRACT

The invention relates to a method for modification of a host cell at a target locus, which method comprises: providing a host cell comprising, at a first locus, at least two site-specific recombination sites and a nucleic acid having an essential function or encoding a product having an essential function; introducing into the host cell, at the target locus, a further nucleic acid having the essential function or encoding for a product having the essential function; and carrying out recombination at the first locus via the at least two site-specific recombination sites, so that the nucleic acid having an essential function or encoding a product having an essential function is rendered non-functional, thereby to modify the host cell at the target locus. The invention also relates to a cell obtainable by a method of the invention.

18 Claims, 12 Drawing Sheets

Pathway integration construct pDSM-Sc3

5'YPRC/ LacZ  lox66  Tet-off  Cre  TIF35  RFP  Nourseo-  lox71  3'YPRC/
TAU3                                         thricin          TAU3
                                             resistance Pathway integration construct pDSM-Sc3a 5'YPRC/ LacZ  FRT  Tet-off  FLP  TIF35  RFP  Nourseo-  FRT  3'YPRC/
TAU3                                         thricin       TAU3
                                             resistance Pathway integration construct pDSM-An3

5'amyB  amyB  lox66  Tet-off  Cre  TIF35  DsRed-SKL  Hygromycin B  lox71  3'amyB
                                                    resistance Pathway integration construct pDSM-An3a 5'amyB  amyB  FRT  Tet-off  FLP  TIF35  DsRed-SKL  Hygromycin B  FRT  3'amyB
                                                   resistance

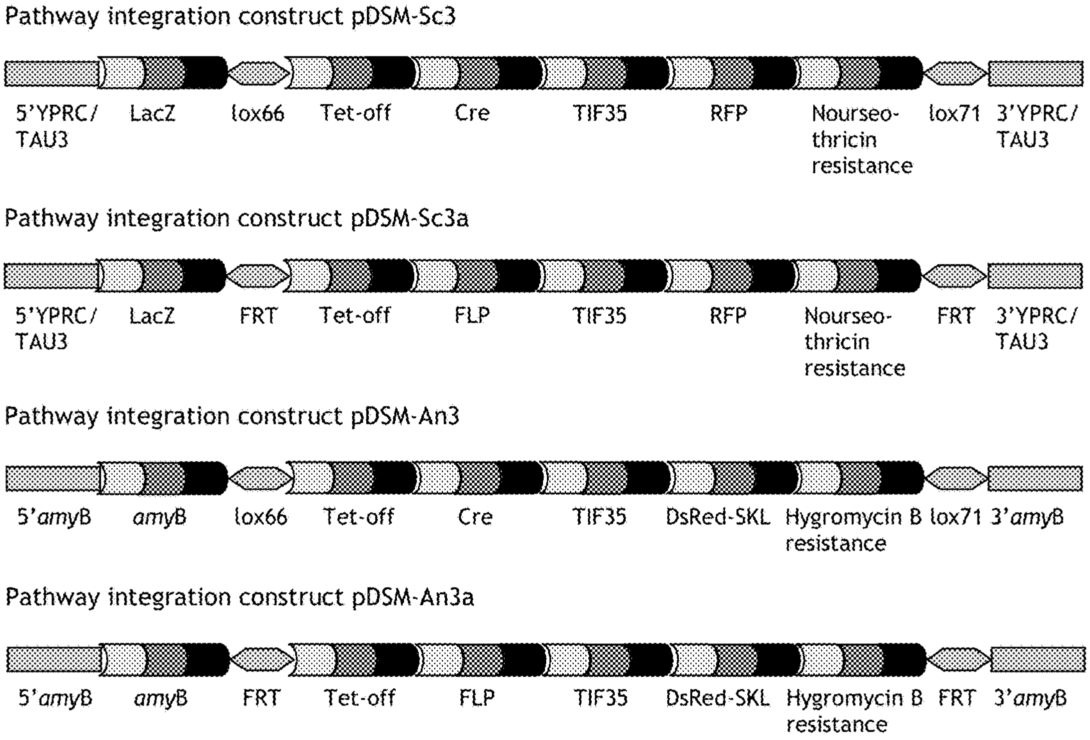

Fig. 3

Multiple genes of interest

5' Int-x    Orf 1    Orf 2    Orf 3    TIF35    3' Int-x

Multiple genes of interest

5' Int-x    Orf 1    Orf 2    Orf i    TIF35    3' Int-x

5' Int-x    Orf 1    TIF35    Orf 2    Orf i    3' Int-x

5' Int-x    Orf 1    2    i    TIF35          3' Int-x

Knock-out construct gene X

5' Int-x    TIF35    3' Int-x

Promoter replacement construct gene X

5' Int-x    TIF35    Pro    Orf X   3' Int-x

Protein modular domain replacement construct gene X

5' Int-x  Pro  Orf X    Orf X        TIF35      3' Int-x
              (left)    (right)

Growth before transformation: 2% glucose till OD~1 followed by 2% galactose 2h
Recovery: 2% glucose, 1.5h (30°C)
Plates: 2% glucose + 200 ug/ml HygB Growth before transformation: 2% glucose till OD~1
Recovery: 2% galactose, 1.5 h
Plates: 2% glucose + 200 ug/ml HygB Growth before transformation: 2% glucose till OD~1
Recovery: 2% galactose, overnight
Selection plates: 2% galactose + 200 ug/ml HygB

CELL MODIFICATION METHOD USING ESSENTIAL GENES AS MARKERS AND OPTIONALLY RECYCLING THESE

CROSS REFERENCE TO RELATED APPLICATIONS

This application is a § 371 National Stage Application of PCT/EP2013/069532, filed Sep. 19, 2013, which claims priority to EP 12185052.3, filed Sep. 19, 2012.

BACKGROUND

Field of the Invention

The invention relates to a method for the modification of a host cell at a target locus. The invention also relates to a host cell obtainable by such a method. The invention further relates to a method for the production of a biological compound of interest using a cell modified according to the invention with a nucleic acid of interest.

Description of Related Art

Transformation of micro-organisms, such as fungi or yeasts, is a well-known procedure to enhance, introduce or alter specific traits. For this purpose, both foreign and endogenous DNA-sequences can be used. As transformation is not 100% efficient, marker genes are used to select transformed strains, i.e. individuals containing the desired trait. The marker gene is part of the introduced DNA and confers a new property to the transformed strain that may be selected for. Examples of commonly used markers are antibiotic or other toxic compound resistance genes, genes relieving auxotrophy or genes involved in the metabolism of a certain compound.

Marker genes are used with varying rates of success. Factors hampering success include: 1) depletion of the antibiotic/toxic compound from culture media by true transformed strains, allowing non-transformed strains to grow; and 2) cross-feeding of essential components. These factors cause background growth and thus multiple purification rounds are required to obtain pure transformed strains. This process can be time-consuming. Moreover, for certain classes of selection markers, such as auxotrophic markers or markers involved in metabolism, the use of defined media is necessary to select transformed strains. Often, these defined media reduce growth in comparison with non-defined growth media.

Fungi often show multi-nuclei which hampers the selection for the cell where all nuclei have the same genotype. This requires multiple selection rounds, often via a sporulation phase for the identification of single-nuclei stadia, which is time-consuming.

In addition, marker genes typically need to be removed from the strain for usage in commercial fermentations. This removal might lead to unexpected genotypic and/or phenotypic effects.

When performing high-throughput (HTP) transformations in microtiter plate format, minimization of background growth becomes even more difficult. Fewer markers are suitable for this purpose and, due to the limited growth area in microwells, depletion of the selective agent or cross-feeding are common. Typically, selection plates are applied, while automation might benefit from selection in liquid media, which is not possible when depletion of the selective agent or cross-feeding occurs.

Accordingly, the efficiency of HTP transformations is severely hampered by these effects.

SUMMARY

The present invention relates to a method for modification of an organism. The method may be used, for example, to knock-out a gene or to transfer any desired nucleic acid or nucleic acids into an organism. That is to say, the method may be used as a method for transformation of an organism.

The present invention is based on the use of essential genes, i.e. a nucleic acid (or nucleic acids), which have a functionality or encode for a functionality without which an individual cell is non-viable or may not divide (in the particular conditions to which the cell is exposed). Such genes may be used for selection by complementation of the essential functionality. Use of such genes ensures that the only surviving strains are those containing a complementing essential functionality, so that background growth is mitigated.

Herein, a nucleic acid (or nucleic acids) which has a functionality, or which encodes for a functionality, without which an individual cell is non-viable or may not divide/replicate (in the particular conditions to which the cell is exposed) may be referred to as an essential nucleic acid. The essential nucleic acid may be a single nucleic acid. However, the invention may be carried out in a format where two or more nucleic acids taken together have or encode for an essential functionality In order to be able to use an essential gene as a selection marker, this gene is typically first inactivated, i.e. rendered non-functional, for example by deletion, in the host genome. There are several ways to knock-out expression of an essential gene, such as silencing with siRNA, suppression of promoter activity, mutagenesis, partial or complete removal from the chromosome or rearrangement of the essential gene DNA. In the invention, a different approach is typically used for essential gene knock-out.

In particular, the selected essential gene is replaced, entirely or in part, with either an exact copy or with a variant of the gene, or with one or more genes that, together, may replace the essential functionality encoded by the gene that is replaced.

This replacement (essential) gene is provided together with site-specific recombination sites, which can be recognized by a recombinase, such as a tyrosine recombinase, for example Cre-recombinase. The replacement (essential gene) may be located between two site-specific recombination sites.

A nucleic acid encoding the recombinase may also be provided, for example situated between the same recombination sites (so that it will be deleted upon induction and expression of the recombinase) or elsewhere in the genome, via a plasmid or provided via transient expression.

The recombinase-encoding nucleic acid may be expressed under the control of an inducible promoter, so that, upon induction of the promoter, the recombinase is produced.

The recombinase is selected so that it is capable of recognising the site-specific recombination sites and the site-specific recombination sites are positioned so that, in the presence of the recombinase, recombination occurs so that the "replacing" essential gene is rendered non-functional. Typically, site-specific recombination sites will be located on both sites (i.e. "upstream" and "downstream") of the replacing essential gene so that it is deleted in its entirety (in the presence of the recombinase).

The essential gene is (either simultaneously, sequentially or separately) re-introduced in a transformation round at a target locus. Direct replacement of the essential gene in this way thus enables survival of successful transformants. In this transformation round, a nucleic acid comprising the essential gene is introduced at the target locus. The transformation round may be carried out so that the essential gene replaces a sequence at the target locus, for example, resulting in a knock-out at the target locus (see FIG. 5). Alternatively or in addition, one or more genes of interest (for example each member of a biochemical pathway) may also be introduced at the target locus (see FIG. 4).

As a further improvement, the essential gene in the introduced at the target locus may also be provided with site-specific recombination sites and, optionally, a recombinase encoding sequence. In this way, iterative transformation rounds can be performed, using a sequence having the same essential functionality (or sequences which, taken together, provide the same essential functionality). In each round, an essential sequence may be rendered non-functional at one location and a replacement copy of the essential sequence introduced at a target locus. Each target locus may be a different locus or the same locus as the target locus in the previous transformation cycle.

To fine-tune deletion of the marker via recombinase activity, dual induction of the recombinase gene can be used, for instance with the tet-on/tet-off system. In this way, the recombinase can only be induced from one location at the same time. Also, different recombination sites and recombinases can be used in an alternating manner.

According to the invention, there is thus provided a method for modification of a host cell at a target locus, which method comprises:

providing a host cell comprising, at a first locus, at least two site-specific recombination sites and a nucleic acid having an essential function or encoding a product having an essential function;

introducing into the host cell, at a target locus, a further nucleic acid having the essential function or encoding for a product having the essential function; and carrying out recombination at the first locus via the at least two site-specific recombination sites, so that the nucleic acid having an essential function or encoding a product having an essential function (positioned at the first locus) is rendered non-functional, thereby to modify the host cell at the target locus.

The invention also provides a host cell obtainable by a method according to any one of the preceding claims. The method of the invention is set out schematically in FIGS. 6 and 7—see steps 1 and 2. Step 3 of FIG. 6 sets out schematically how the method of the invention may be used for iterative modifications of a cell.

BRIEF DESCRIPTION OF THE DRAWINGS

FIGS. 1-7 depict embodiments as described herein.

DETAILED DESCRIPTION OF A PREFERRED EMBODIMENT

The invention may also be carried out in a format wherein a host cell is provided with two or more nucleic acids having an essential function or encoding a product having an essential function (herein an "essential nucleic acid"), each one provided with two or more site-specific recombination sites.

In this way, modifications of a host cell may be targeted to two or more target loci simultaneously, sequentially or separately. The two or more essential nucleic acids in a host cell may be provided with the same or different site-specific recombination sites. That is to say, one recombinase may be used to remove more than one essential nucleic acid at the same time.

The method of the invention may be used to produce stable transformants. The transformants are stable since the nucleic acid of interest is tightly linked to the essential gene in the host cell.

Where the method of the invention is used to introduce a nucleic acid of interest, the nucleic acid of interest may be any nucleic acid of interest, for example a nucleic acid which encodes a desired protein.

Accordingly, the invention provides a method for the production of a biological compound of interest, which method comprises culturing a host cell of the invention transformed with a nucleic acid encoding the biological compound of interest or a compound involved in the synthesis of the biological compound of interest under conditions conducive to the production of the biological compound of interest and, optionally, isolating the compound of interest from the culture broth.

Also, the invention provides a method for the production of a biological compound of interest, which method comprises transforming a host cell with a nucleic acid encoding the biological compound of interest or a compound involved in the synthesis of the biological compound of interest according to the method of the invention and culturing the resulting host cell under conditions conducive to the production of the biological compound of interest and optionally isolating the compound of interest from the culture broth.

The nucleic acid of interest may be a promoter sequence. Accordingly, the invention relates to a method in which the resulting transformant comprises an essential nucleic acid at the target locus followed by a replacement sequence for the promoter sequence at the target locus. This allows for adapting the promoter activity of the nucleic acid in controls. Such a method may be desirable for creating transformants with modified expression profiles of one or more genes.

The nucleic acid of interest may be the essential nucleic acid itself. Accordingly, the invention relates to a method in which the resulting transformant comprises an essential nucleic acid at the second locus which essential nucleic acid is also the nucleic acid of interest. Such a method may be desirable for creating knock-out transformants.

BRIEF DESCRIPTION OF THE DRAWINGS

Figure 1:
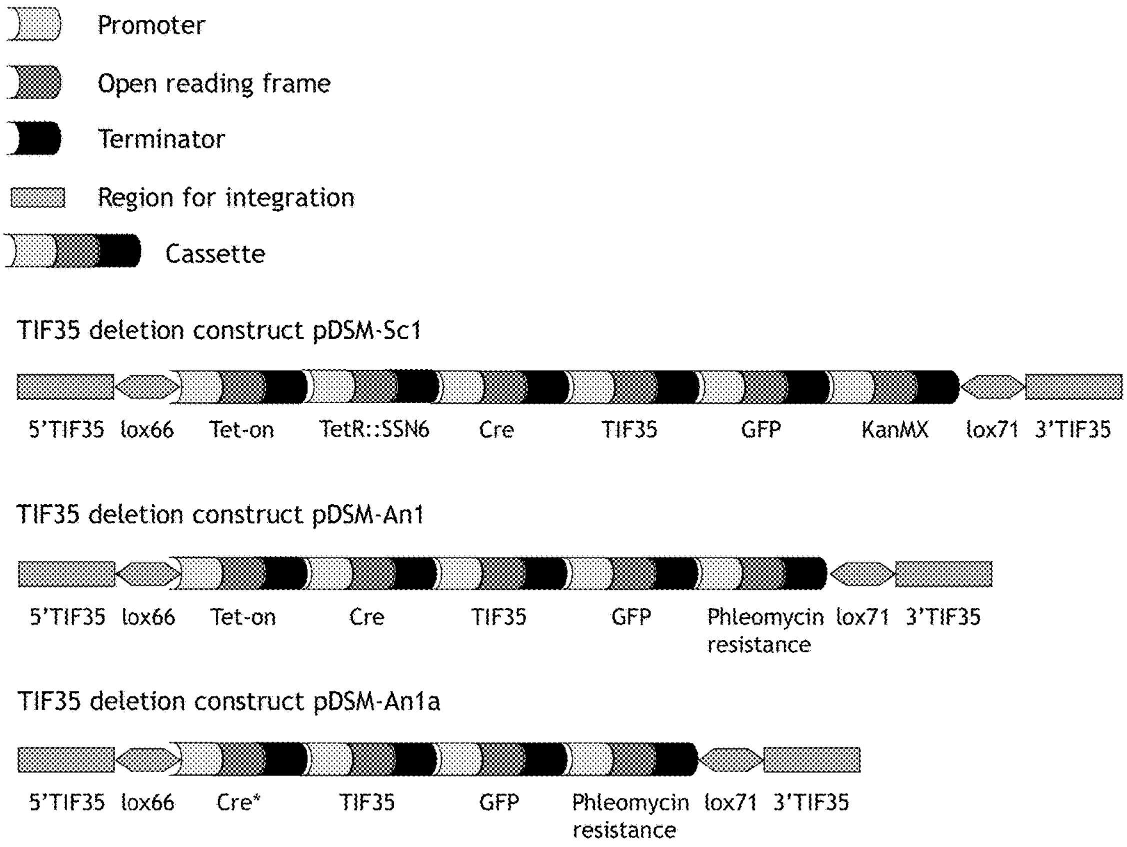

FIG. 1 shows TIF35 deletion constructs pDSM-Sc1, pDSM-An1 and pDSM-An1a. The essential TIF35 marker gene in this construct is used to replace the original endogenous TIF35 gene. Cre-recombinase (either induced by the tet-on system or xylose) and loxP sites are added to be able to excise the construct at a later stage. TetR-SSN6 helps to decrease basal expression of Cre-recombinase in *S. cerevisiae* under non-inducing conditions. Additional markers like KanMX, phleomycin resistance and GFP are optional and only used for testing purposes.

Figure 2:
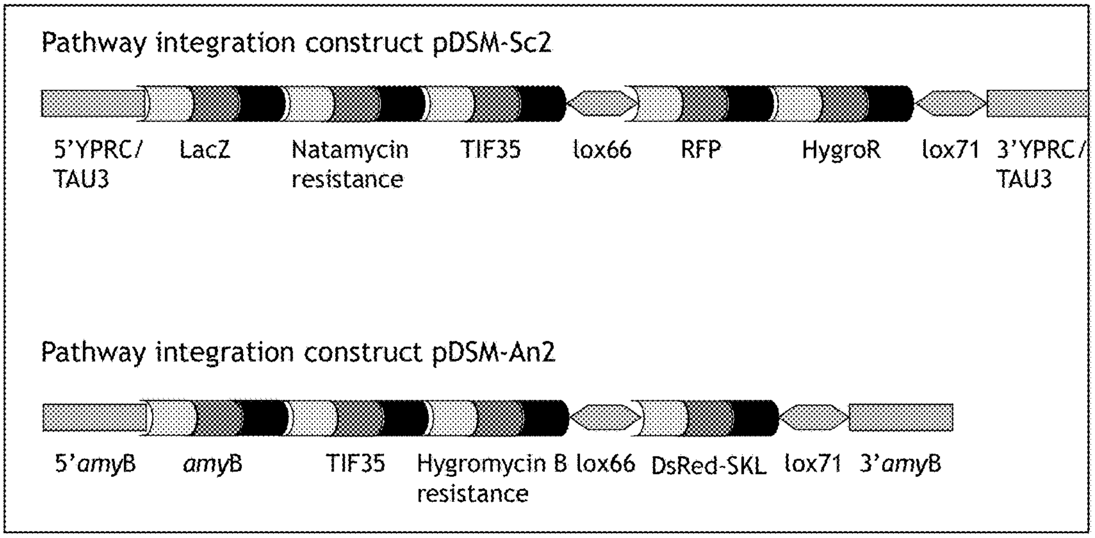

FIG. 2 shows pathway integration constructs pDSM-Sc2 and pDSM-An2. Genes of interest, like LacZ and amyB, are integrated at selected loci using TIF35 as essential marker. Additional markers like nourseothricin resistance, hygromycin B resistance and DsRed/RFP are optional and only used for testing purposes. DsRed/RFP and Hygro R in case of pDSM-Sc2 are placed between loxP recombination sites to test the effect of Cre-recombinase expression from constructs pDSM-Sc1, pDSM-An1 or pDSM-An1a.

FIG. 3 shows pathway integration constructs pDSM-Sc3, pDSM-Sc3a, pDSM-An3 and pDSM-An3a. Genes of interest, like LacZ and amyB, are integrated at selected loci using TIF35 as essential marker. Additional markers like nourseothricin resistance, hygromycin B resistance and DsRed/RFP are optional and only used for testing purposes. Cre-recombinase, controlled by the Tet-off system, is included to be able to excise the markers. This will allow for iterative transformation rounds, using the TIF35 essential marker gene. As alternative for Cre-recombinase, including loxP recombination sites, FLP recombinase is used together with FRT recombination sites. An alternative for the Tet_off promoter is a second regulatable promoter such as GAL10 in *S. cerevisiae*. This allows for independent regulation of the two CRE recombinase genes on separate chromosomes, or CRE and FLP.

Figure 4:
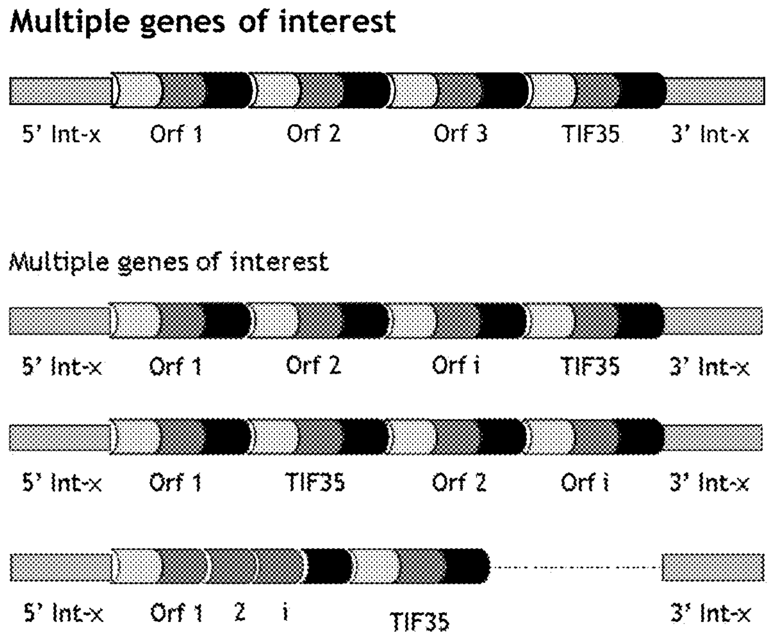

FIG. 4: Integration construct with the essential TIF35 gene as marker containing multiple genes of interest, which may form a (partial) pathway. Orf: open reading frame; Int-x: integration site x. Also variants showing that TIF35 can be at different locations, and a variant showing multiple Orfs in a bacterial operon structure.

Figure 5:
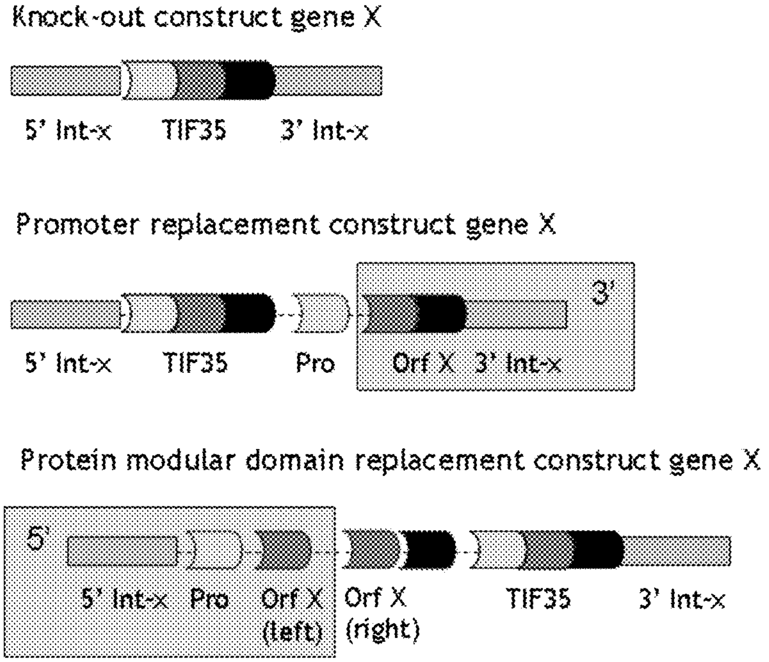

FIG. 5: The method of the invention can also be applied for knock-out of DNA sequence or for example replacement of a full gene including promoter and terminator or multiple genes, or just disruption of a certain functionality by splitting a promoter or Orf by inserting the essential functionality. In addition, the method can be applied for example for (partial) promoter replacement (middle) or partial replacement of a protein, for example to exchange part of a protein to make hybrid proteins or do (partial) protein engineering.

Figure 6:
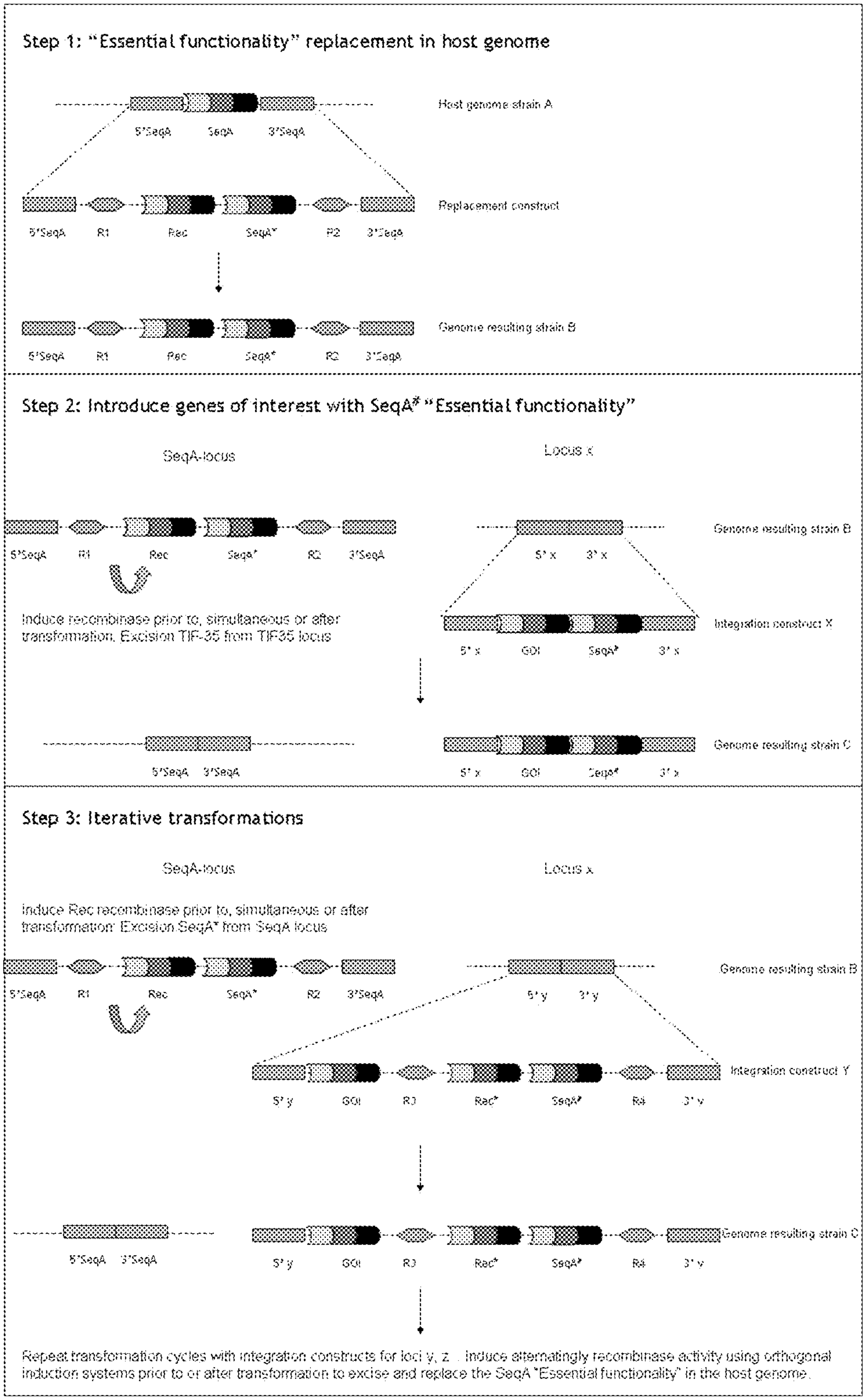

FIG. 6: Schematic overview of the procedure. In step 1 the "Essential functionality" encoded by SeqA is replaced by a copy or variant construct that can replace the "Essential functionality" called SeqA* between recombination sites R1 and R2. In step 2, this SeqA* is excised from the SeqA locus by a recombinase, which is induced and gene(s) of interest (GOI) are introduced via construct X on locus x, together with a new copy or variant construct that can replace the "Essential functionality" SeqA/SeqA*by SeqA$^{\#}$. As an alternative, iterative transformation is possible using step 3 instead of step 2, the same is done with construct Y on locus y. Construct Y contains, besides genes of interest (GOI), the SeqA* between R3 and R4 recombination sites, together with the same or another recombinase gene under the same or a different orthogonal induction system. This enables subsequent excision of the SeqA (or variants) from locus y by the recombinase at Y, which is induced via the same or an orthogonal induction system. Thereby, this strain can be used in iterative transformation rounds using the essential SeqA (or variants) gene as selection system.

Figure 7:
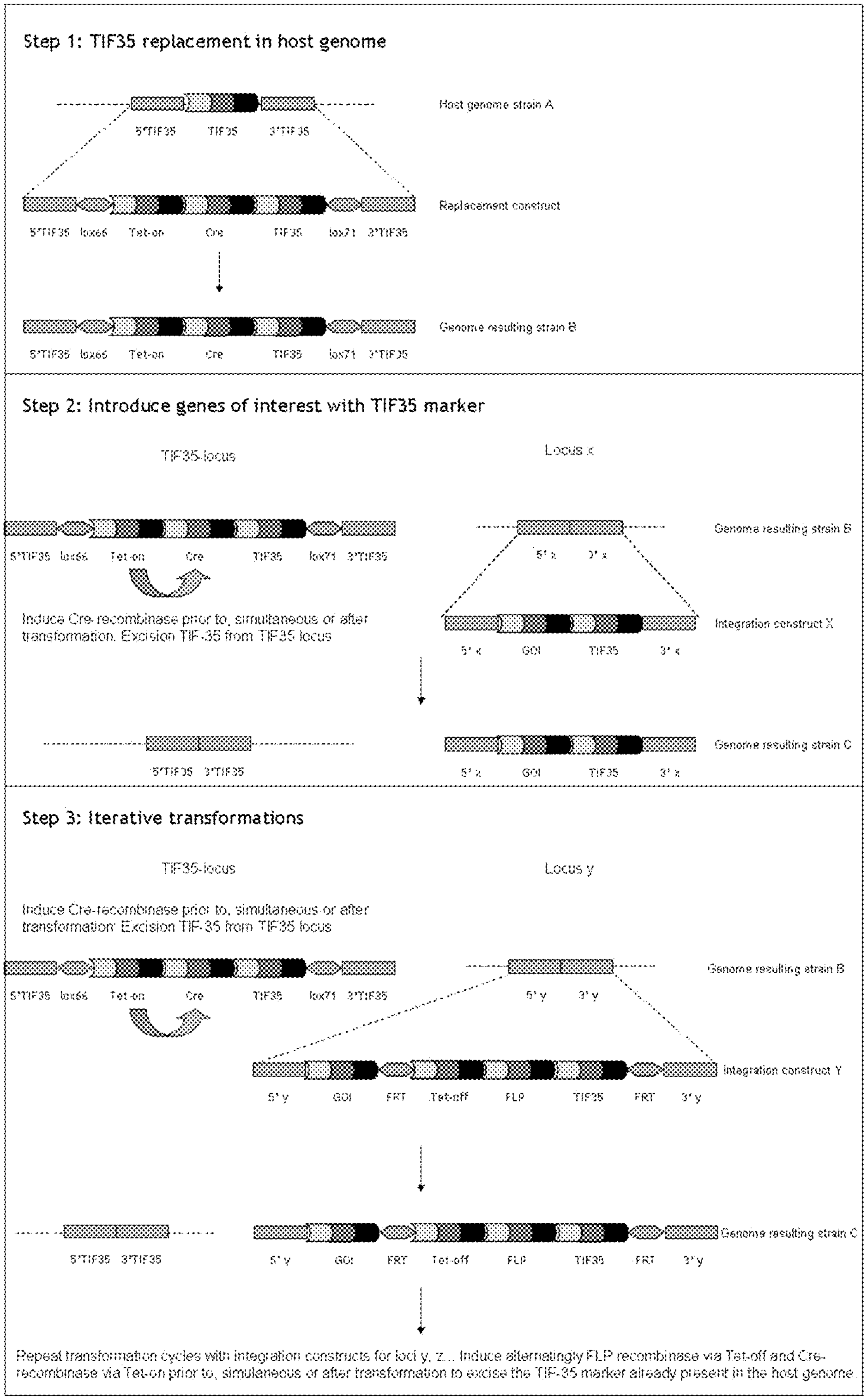

FIG. 7: Schematic overview of the procedure. In step 1 the essential TIF35 marker gene is replaced by a copy between loxP recombination sites. In step 2, this TIF35 copy is excised from the TIF35 locus by Cre-recombinase, which is induced via the Tet-on system and gene(s) of interest (GOI) are introduced via construct X on locus x, together with a new copy of the TIF35 gene. As an alternative, iterative transformation is possible using step 3 instead of step 2, the same is done with construct Y on locus y. Construct Y contains, besides genes of interest (GOI), the TIF35 marker between FRT recombination sites, together with the FLP recombinase gene. This enables subsequent excision of the TIF35 marker from locus y by FLP recombinase, which is induced via the Tet-off system. Thereby, this strain can be used in iterative transformation rounds using the essential TIF35 gene as marker.

FIG. **8*a*** shows a schematic overview of a replacement construct. The essential TIF35 marker gene in this construct is used to replace an original endogenous TIF35 gene. Cre-recombinase (induced by galactose) and loxP sites are added to be able to excise the construct at a later stage.

FIG. **8*b*** shows a schematic overview of a pathway integration construct. A gene of interest, LacZ, may be integrated at a selected loci (YPRC/TUA3) using TIF35 as essential marker. Additional markers, hygromycin B resistance and kanMX, are provided for testing purposes.

Figure 9:
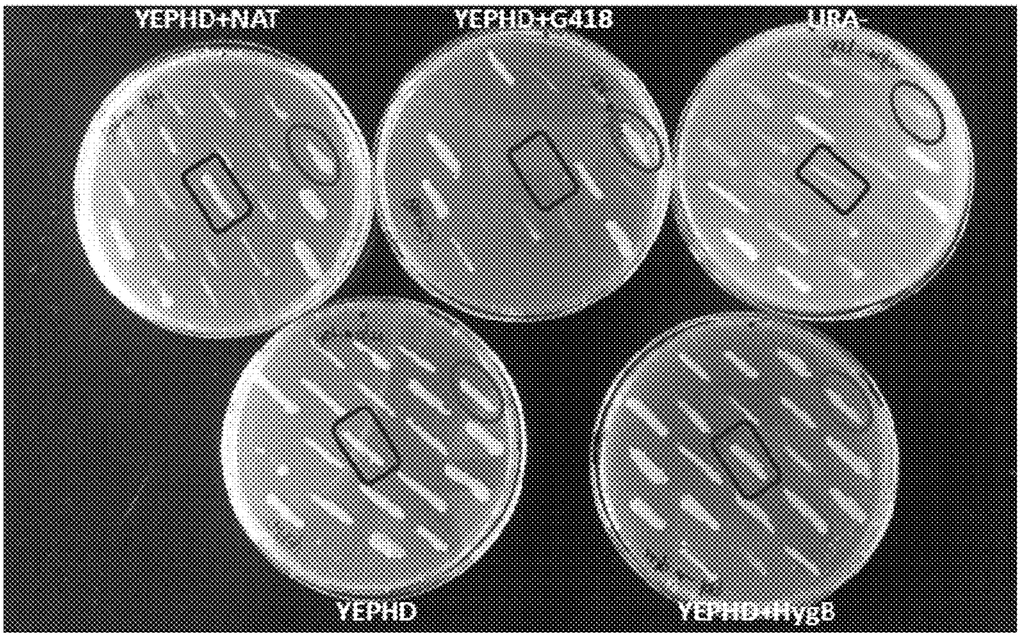

FIG. 9 shows the growth of yeast colonies on media applying alternative selection as indicated. A yeast strain comprising a replacement construct were grown in 2% glucose until an OD of ~1 OD/ml, followed by CRE induction in 2% galactose for 2 hour. After transformation with fragments for the assembly of a pathway integration construct, cells were grown in 2% glucose without selection for 1.5 hour (30° C.) followed by plating onto hygromycin selective plate (2% glucose+200 μg/ml HygB). 21 independent colonies were then streaked onto different selective plates for genotyping.

Figure 10:
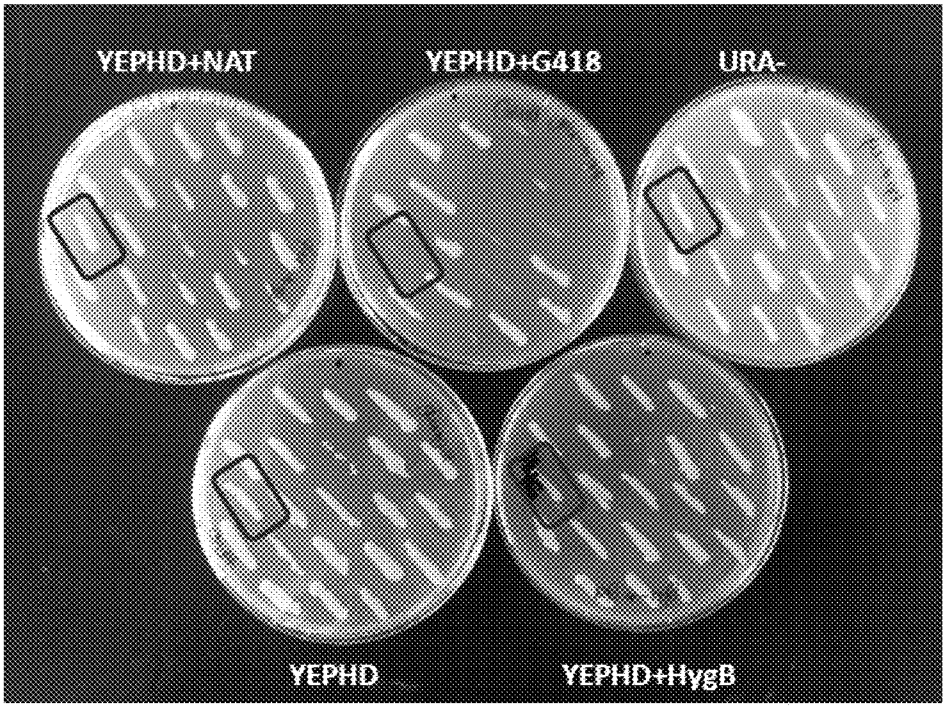

FIG. 10 shows the growth of yeast colonies on media applying alternative selection as indicated. A yeast strain comprising a replacement construct were grown in 2% glucose until an OD of ~1 OD/ml. After transformation with fragments for the assembly of a pathway integration construct, cells were grown in 2% glucose for 1.5 hour (30° C.) in the presence of 2% galactose, followed by plating onto hygromycin selective plate (2% glucose+200 μg/ml HygB). 21 independent colonies were then streaked onto different selective plates for genotyping.

Figure 11:
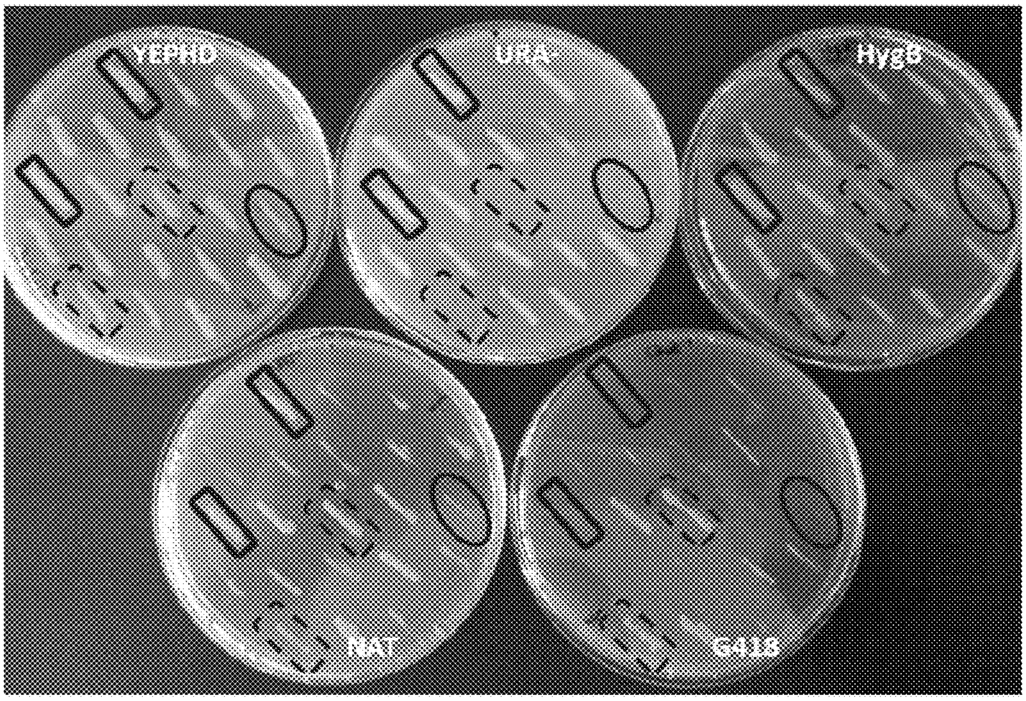

FIG. 11 shows the growth of yeast colonies on media applying alternative selection as indicated. A yeast strain comprising a replacement construct were grown in 2% glucose until an OD of ~1 OD/ml. After transformation with fragments for the assembly of a pathway integration construct, cells were grown in 2% glucose overnight in the presence of 2% galactose, followed by plating onto hygromycin selective plate (2% glucose+200 μg/ml HygB). 21 independent colonies were then streaked onto different selective plates for genotyping.

Figure 12:
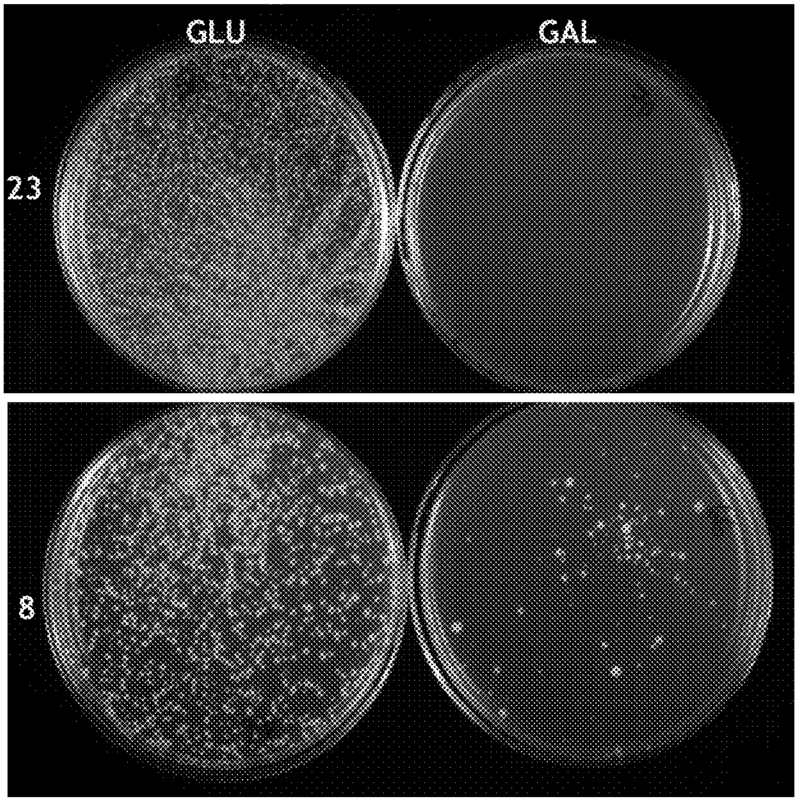

FIG. 12 shows characterization of TIF35 and CRE-dependent lethality of a yeast strain containing a replacement construct. Different colonies of the yeast strain were grown in YEP+2% glucose (as controls, should be viable) or in YEP+2% galactose (to induce CRE recombinase). About 1000 fold dilution of a 0.5 to 2 OD/ml of a 48 hr culture was plated out for independent transformation colonies.

BRIEF DESCRIPTION OF THE SEQUENCE LISTING

SEQ ID NOs: 1 to 6 sets out flanking regions for use in *S. cerevisiae*.

SEQ ID NOs: 7 to 14, 75 and 80 set out promoters for use in *S. cerevisiae*.

SEQ ID NOs: 15 to 24, 74 and 76 set out coding sequences for use in *S. cerevisiae*.

SEQ ID NOs: 25 to 36 and 77 set out terminators for use in *S. cerevisiae*.

SEQ ID NOs: 37 to 41 set out flanking regions for use in fungi.

SEQ ID NOs: 42 to 51 set out promoters for use in fungi.

SEQ ID NOs: 52 to 61 set out coding sequences for use in fungi.

SEQ ID NOs: 62 to 69 set out terminators for use in fungi.

SEQ ID NOs: 70 to 73 set out recombination site sequences.

SEQ ID NO: 78 sets out the sequence of a URA3 marker cassette (including promoter and terminator).

SEQ ID NO: 79 sets out the sequence of a NAT marker cassette (including promoter and terminator).

Throughout the present specification and the accompanying claims, the words "comprise", "include" and "having" and variations such as "comprises", "comprising", "includes" and "including" are to be interpreted inclusively. That is, these words are intended to convey the possible inclusion of other elements or integers not specifically recited, where the context allows.

The articles "a" and "an" are used herein to refer to one or to more than one (i.e. to one or at least one) of the grammatical object of the article. By way of example, "an element" may mean one element or more than one element.

The invention relates to a method for modification of a cell. Modification of a cell, for the purposes of this invention, implies that the genetic make-up of an organism is changed using the method of the invention. Such changes may be any change to the genetic make-up of the organism, for example deletion or replacement of genetic material or the introduction of new genetic material. Thus, the invention relates to knock-out and replacement of genetic sequences and also to the introduction of one or more nucleic acids of interest.

Where the method of the invention involves the introduction of one or more nucleic acids of interest, the invention may be seen as a method of transformation of a cell.

Transformation of a cell means a process in which one or more nucleic acids are introduced into a cell. Thus, transformation is the genetic alteration of a cell resulting from the direct uptake, incorporation and, optionally, expression of exogenous genetic material from its surroundings and taken up through the cell membrane(s). The genetic material is referred to as exogenous since originates outside of the organism of concern or study.

Transformation occurs naturally in some species of bacteria, but it can also be effected by artificial means in other cells. Herein, "transformation" is also used to describe the incorporation of new genetic material into non-bacterial cells, including animal and plant cells. Introduction of nucleic acids into eukaryotic cells is often called "transfection", but herein the term "transformation" also encompasses transfection.

The method of the invention may be an in vitro method, an ex vivo method or an in vivo method.

Nucleic acids introduced into a cell using the method of the invention may be nucleic acid(s) which are naturally present in the organism of concern or study, for example to add a further copy of a given nucleic acid. Alternatively, the introduced nucleic acids may be nucleic acids which do not naturally occur in the organism of concern of study. Thus, nucleic acid may be introduced into a cell which would not normally be seen in such a cell.

As set out herein, the method may be used to knock-out a nucleic acid in a cell. Thus, the invention may be used to make gene deletions. Such deletion may involve the partial or complete removal of a gene sequence. Typically, though the deletion is intended to render the gene non-functional.

In a knock-out procedure, the deleted sequence may be replaced with different nucleic acid, for example, a nucleic acid of interest.

A method for modification of a host cell at a target locus, which method comprises:

providing a host cell comprising, at a first locus, at least two site-specific recombination sites and a nucleic acid having an essential function or encoding a product having an essential function;

introducing into the host cell, at a target locus, a further nucleic acid having the essential function or encoding for a product having the essential function; and carrying out recombination at the first locus via the at least two site-specific recombination sites, so that the nucleic acid having an essential function or encoding a product having an essential function (located at the first locus) is rendered non-functional, thereby to modify the host cell at the target locus.

Accordingly, the method of the invention is typically carried out in three steps:

(a) modification of the host cell with a first copy of the essential nucleic acid;

(b) introduction of a second version of the essential nucleic acid (this version may be the same of different from the first copy, but will have or encode for the same essential functionality); and (c) removal of the first copy of the essential nucleic acid.

These steps may be carried out simultaneously, sequentially or separately. Typically, step (a) is carried out, followed by step (b) and (c), which two steps may be carried out simultaneously. Alternatively, step (c) may follow step (b).

Step (a) may need to be carried out only once in order to provide a strain of the host cell which may be used in multiple modifications, i.e. using steps (b) and (c) either simultaneously, sequentially or separately In the method of the invention, a cell is provided which, at a first locus, comprises a nucleic acid having an essential function or encoding an essential function ("essential nucleic acid") and at least two site-specific recombination sites. The recombination sites are arranged, in relation to the essential nucleic acid, so that in the presence of a recombinase which recognizes the recombination sites, recombination occurs so that the essential nucleic acid is rendered non-functional.

Typically, therefore, the essential nucleic acid is flanked by at least two site-specific recombination sites, arranged so that there is at least one site-specific recombination site on both sides of the essential nucleic acid. In this format, the site-specific recombination sites are selected so that, in the presence of a suitable recombinase, the essential nucleic acid may be out-recombined. However, depending on the orientation of the site-specific recombination sites, the orientation of the essential nucleic acid could be reversed (by recombination) to render it non-functional.

The site-specific recombination sites may be arranged, so that only a portion of the essential nucleic acid is removed in order to render it non-functional. For example, where in the essential nucleic acid comprises a promoter and a coding sequence, the site-specific recombination sites may be arranged so that only the promoter of the coding sequence is removed (in the presence of a recombinase), thus rendering the essential nucleic acid non-functional. Alternatively, site-specific recombination sites may be arranged so that sequence within a essential nucleic acid is removed, for example to induce a frame-shift in a coding sequence.

Typically, the provision of such a cell will involve the deletion or replacement of any copy or copies of the essential nucleic acid comprised by the cell. The cell will thus typically be provided in a form where only one copy of the essential nucleic acid (flanked by two or more site-specific recombination sites) is present. The essential nucleic acid used to replace the endogenous essential nucleic acid may be the same as or different from the endogenous version, so long as it has or encodes for the same essential function.

The essential nucleic acid may, conveniently, be provided to the cell via use of a replacement/deletion construct (see FIG. 6). In such a construct, a codon variant of the endogenous essential nucleic acid may be used to minimize single cross-over integration with the endogenous essential nucleic acid. The construct may also be provided with an alternative promoter and/or terminator sequence to minimize single cross-over integration with the endogenous essential nucleic acid.

The construct may also be provided with a recombinase encoding sequence, typically in a format so that expression of the recombinase is inducible. These elements are located between site-specific recombination sites. The site-specific recombination sites are typically further flanked (on both sides) by sequences which allow recombination with the first locus which will typically be the endogenous copy of the essential nucleic acid.

Introduction of such a construct into a host cell generally results in replacement of the endogenous essential nucleic acid with a copy of the essential nucleic acid flanked by one or more site-specific recombination sites. However, the invention may be carried out such that integration of the essential nucleic acid flanked by site-specific recombination sites takes place at a different locus that that of the endogenous essential nucleic acid and the endogenous copy is simultaneously or subsequently deleted/replaced.

In the step of introducing a modification at the target locus, a further copy of the essential nucleic acid is introduced at the target locus, optionally together with one or more nucleic acids of interest. The further copy of the essential nucleic acid and optional nucleic acid(s) of interest may, conveniently, be provided to the cell via use of an integration construct (see FIG. 6).

In such an integration construct, integration sites are typically used to enable targeting of the second copy of the essential nucleic acid and optional nucleic acid(s) to the target locus. Typically, integration sites are nucleic acid sequences that allow homologous recombination of the construct with the second locus. Integration sequences may be used so that a specific target locus is selected. Typically, such sequences and the target locus are selected so that there is no deleterious effect on strain fitness. However, integration sequences may be used such that random integration takes place.

A replacement/deletion construct and/or an integration construct may be provided as a single construct or in the form of two or more nucleic acid fragments which may recombine as a single nucleic acid (i.e. entire construct) in a host cell. Thus, the essential gene and/or a recombinase encoding sequence may be provided as split fragments. This approach is described in patent publication nos. WO2013/135729 and WO2013/135728.

The nucleic acid of interest may be any nucleic acid which is intended to be incorporated at the second locus. The nucleic acid of interest may, when expressed, give rise to a RNA which has some desired effect in the host cell, for example a non-coding RNA such as tRNA, rRNA, snoRNA, microRNA, siRNA, piRNA or a long non-coding RNA. Alternatively, the nucleic acid of interest may comprise coding sequence, i.e. will give rise, when expressed, to a peptide/polypeptide. Typically, the nucleic acid of interest will incorporate one or more control sequences which are operably linked to the sequence giving rise to RNA and/or a peptide/protein.

The nucleic acid of interest may be a control sequence, such as a promoter. Thus, an integration construct may be designed so that an endogenous promoter is replaced with a different promoter (see FIG. 5 which illustrates a promoter replacement integration construct). The nucleic acid of interest may comprise control sequence and coding sequence, for example all of part of an open reading frame. FIG. 5 illustrates the use of an integration construct which replaces a portion of an open reading frame, for example a domain, with an alternative version of that portion.

One or more nucleic acids of interest may be incorporated at the second locus using the method of the invention. That is to say, an integration construct may comprise two or more nucleic acids of interest. For example, one or more nucleic acids each encoding a different protein, for example the members of a metabolic pathway, may be incorporated at the second locus (see FIG. 4).

An integration construct may comprise an essential nucleic acid and no additional nucleic acid of interest. Such an integration construct may be useful in creating knock-out transformants. That is to say, such an integration may be used to generate, for example, a transformant which is disrupted at a targeted locus. For example, an entire promoter or open reading frame or part of either thereof may be replaced with the further copy of the essential nucleic acid carried by the integration construct (see Example 5 for an illustration of a knock-out construct).

An integration construct designed to knock-out/delete sequence from a host cell may also carry a nucleic acid of interest in addition to the essential nucleic acid, for example a nucleic acid of interest which is a coding sequence. Thus, knock-out and overexpression of a nucleic acid of interest may be carried out simultaneously.

Typically of course, the method of the invention will be carried out simultaneously on multiple host cells. Accordingly, a heterogeneous population of integration constructs may be used to transform multiple cells at the same time. For example, a library of integration constructs may be generated, which library comprises variation at the level of the nucleic acid of interest. Such a library of integration constructs may be used to transform host cells in order to generate a library of host cells.

The step of removing the first copy of the essential nucleic acid may be carried out by providing the cell with a recombinase which recognizes two of the site-specific recombination sites flanking that first copy of the essential nucleic acid. See steps 1 and 2 of FIGS. 6 and 7 which show essential nucleic acids flanked by site-specific recombination sites.

Typically, the recombinase may be provided by incorporating a recombinase-encoding nucleic acid sequence into the replacement/integration construct. Preferably, the recombinase-encoding sequence is operably linked with one or more control sequences so that expression of the recombinase may be induced. Preferably, the recombinase-encoding nucleic acid is located between at least two site-specific recombination sites, so that, on expression of the recombinase, the recombinase-encoding sequence is removed along with the essential nucleic acid.

Alternatively, the recombinase may be provided in the form of protein which is introduced into the host cell or in the form of an episomal construct, such as a plasmid, incorporating a recombinase-encoding nucleic acid sequence which is introduced into the host cell.

Provision and incorporation of the integration construct and removal of the first copy of the essential nucleic acid may take place simultaneously, sequentially or separately.

Typically, the method of the invention will be carried out in a format in which many cells simultaneously are treated according to the invention. Cells into which the nucleic acid of interest has been introduced may be readily identified since they are the only cells which will survive. Cells into which the nucleic acid of interest is not incorporated will not be present since lack of a copy of the essential nucleic acid means that such cells cannot multiply.

The method of the invention may be carried out in a format such that iterative and/or multiple modifications are possible (see step 3 of FIGS. 6 and 7 for one format in which such iterative modifications may be carried out). There are several alternative approaches in which such transformations may be made possible.

In one alternative, the host cell may be provided with two or more essential nucleic acids, each incorporated at different loci and each flanked by at least two site-specific recombination sites. In this way, more than one nucleic acid of interest may be introduced into the host cell at different loci.

Such a method of the invention may be carried out by providing a host cell which comprises a first essential nucleic acid flanked by at least two site-specific recombination sites at a first locus and at least one further essential nucleic acid flanked by at least two site-specific incorporated at least one further locus. Typically, this may be achieved via multiple replacement/deletion constructs, each providing a different essential gene flanked by site-specific recombination sites.

Multiple nucleic acids of interest may then be introduced at multiple loci. This may be achieved by use of multiple integration constructs, each of which may carry an essential nucleic acid corresponding to one of those introduced by a replacement/deletion construct. Thus, as many loci may be targeted with a nucleic acid of interest as essential nucleic acids are introduced into the host cell via replacement/deletion constructs. The multiple integration constructs could be introduced may be introduced simultaneously, sequentially or separately.

Each of the essential nucleic acids introduced into the host cell using a replacement/deletion construct may be flanked by site-specific recombination sites recognized by the same recombinase. Typically, this will mean that all nucleic acids of interest present on integration constructs will need to be introduced simultaneously with or prior to introduction of the recombinase. In this format of the method of the invention, all, some or only one of the replacement/deletion constructs may be provided with a recombinase-encoding nucleic acid sequence. When expression of that sequence is induced, all of the incorporated essential nucleic acids will be removed.

Alternatively, each of the essential nucleic acids introduced into the host cell using a replacement/deletion construct may be flanked by site-specific recombination sites recognized by different recombinases. In this way, a host cell may be provided in which nucleic acids of interest may be introduced sequentially at different loci, each time making use of a different essential gene and recombinase.

Alternatively, a replacement/deletion construct may comprise two or more essential nucleic acids flanked by site-specific recombination sites. In this way, two integration or more constructs may be used simultaneously to introduce one or more nucleic acids of interest at two or more separate loci.

Of course, in this approach the replacement/deletion construct will only be able to replace/delete all of the corresponding endogenous copies of the essential nucleic acids if the essential nucleic acids chosen are positioned at the same locus. If the two or more essential nucleic acids are not positioned at the same loci additional steps will need to be taken to delete all of the endogenous copies of all of the essential nucleic acids being used.

The two approaches may be combined so that a host cell is provided which comprise multiple different essential genes, each essential gene located at a different locus and flanked by site-specific recombination sites, wherein two or more essential nucleic acids are flanked by site-specific recombination sites recognized by the same recombinase and two or more essential nucleic acids are flanked by site-specific recombination sites recognized by different recombinases.

In a further format of the method of the invention which provides for iterative transformation, the nucleic acid of interest in introduced in the host cell together with the further copy of the essential nucleic acid, wherein the essential nucleic acid is flanked by site-specific recombination sites.

Thus, an integration construct may be used in which the essential nucleic acid is flanked by site-specific recombination sites (see FIG. 3). In this way, the resulting cell (with incorporated nucleic acid of interest) may act as the starting host cell for a further cycle of transformation. That is to say, a further integration construct comprising a further nucleic acid of interest and further copy of the essential nucleic acid (targeted to a further locus) may be used. Incorporation of this construct and removal of the essential gene incorporated with the first integration construct leads to incorporation of a further nucleic acid of interest.

This format of the method of the invention may be carried out so that the essential nucleic acid present on the first integration construct is flanked by site-specific recombination sites recognized by a recombinase different from that which recognizes the site-specific recombination sites flanking the essential nucleic acid on the replacement/deletion construct. In that way, the essential nucleic acid introduced by the replacement/deletion construct may be removed without removing the essential nucleic acid incorporated with the first integration construct. A second integration construct may be used which comprises an essential nucleic acid, which may be optionally flanked by site-specific recombinase recognized by the recombinase used to remove the essential nucleic acid introduced by the replacement/deletion construct.

In this way, reiterative transformation may be carried out with each cycle introducing the essential nucleic acid flanked by site-specific recombination sites which are not recognized by the recombinase used in the subsequent cycle of transformation.

An alternative approach for reiterative transformation relies on the use of inducible promoters for recombinase expression which have the opposite induction in the deletion and pathway integration construct (see FIGS. 1 and 2).

In this approach, the replacement/deletion and integration constructs carry the same recombinase-encoding sequence and the same site-specific recombination sites, but are operably linked to promoters such that the inducer of the recombinase from the replacement/deletion construct represses expression of the recombinase from the integration construct.

For example, a replacement/deletion construct may be used wherein expression of the recombinase is under the control of the tet-on system so that doxycycline may be used to induce recombinase expression. The integration construct by contrast may comprise the same recombinase-encoding sequence under control of the tet-off system so that presence of doxycycline represses expression of the recombinase. By choosing an appropriate amount and duration of doxycycline, enough recombinase expression may be induced from the replacement/deletion construct such that the essential nucleic it provides is removed, but not enough to remove the essential nucleic acid from the integration construct.

In a further cycle of transformation, Tet_off::Cre will be used for excision of the essential nucleic acid from the integration construct. The second integration construct used in a further cycle of transformation may comprise a Tet_on::Cre, so again recombinase expression from this construct will be repressed under the conditions in which recombinase is expressed from the first integration construct.

The essential nucleic acid is preferably a nucleic acid (or nucleic acids taken together) that has not been shown to be non-essential. More preferably, the essential nucleic acid is a nucleic acid, the absence of which, renders the host cell non-viable. In particular, an essential nucleic acid is typically one, the absence of which, renders the cell incapable of dividing. More preferably, the essential nucleic acid is a nucleic acid whose deficiency renders the host cell non-viable under all conditions and on any medium, in particular complex (undefined) medium. However, an essential nucleic acid may be a nucleic acid, the absence of which renders the cell non-viable only under certain defined conditions. An essential nucleic acid in the context of the present invention may be a nucleic acid that renders the host cell non-viable when another (non-essential) nucleic acid has been rendered deficient.

Preferably, the essential gene is an essential gene in other host cells as well. In one embodiment, the essential gene is a gene which is essential in fungi. Preferably, the essential gene is essential in yeast and/or filamentous fungi.

Suitable examples of classes of essential genes include, but are not limited to, genes involved in DNA synthesis & modification, RNA synthesis & modification, protein synthesis & modification, proteasome function, the secretory pathway, cell wall biogenesis and cell division. In the context of the present application, the essential gene is not a auxotrophic marker (such as pyrG), dominant growth marker (such as niaD and amdS) and dominant resistance marker (such as ble). A preferred essential gene is the tif35 gene encoding the g subunit of translation initiation factor 3, which has an ortholog in all eukaryotes. In one embodiment, the tif35 gene encoding the g subunit of translation initiation factor 3, for example from *P. chrysogenum*, may be used as the essential gene. A further example of a suitable essential gene is the *A. nidulans* aur1 gene encoding the enzyme phosphatidylinositol:ceramide phosphoinositol transferase, which is required for sphingolipid synthesis. Thus, in one embodiment, the aur1 gene encoding the enzyme phosphatidylinositol:ceramide phosphoinositol transferase from *A. nidulans* may be used as the essential gene.

Accordingly, out-recombination of the essential nucleic acid will render a host cell non-viable or incapable of dividing (preferably under any conditions, but optionally under specific defined conditions).

In a replacement/deletion construct, the essential nucleic acid is typically flanked by at least two site-specific recombination sites, i.e. the essential nucleic acid has at least one site-specific recombination site positioned 5' and at least one site-specific recombination site position 3' of its location on the construct. These sites enable out-recombination of the essential nucleic acid in the presence of a recombinase via site-specific recombination.

The term "construct", for example in the context of a "replacement/deletion construct" or "integration construct" is herein referred to as a nucleic acid molecule, either single- or double-stranded, which is isolated from a naturally occurring gene or which has been modified to contain segments of nucleic acid which are combined and juxtaposed in a manner which would not otherwise exist in nature. Such constructs may comprise natural and/or non-natural nucleotides.

The term "operably linked" is defined herein as a configuration in which a control sequence is appropriately placed at a position relative to the coding sequence of the DNA sequence such that the control sequence directs the production of an mRNA or a polypeptide.

The term "control sequences" is defined herein to include all components, which are necessary or advantageous for the production of mRNA or a polypeptide, either in vitro or in a host cell. Each control sequence may be native or foreign to the nucleic acid sequence encoding the polypeptide. Such control sequences include, but are not limited to, a leader, Shine-Delgarno sequence, optimal translation initiation sequences (as described in Kozak, 1991, J. Biol. Chem. 266:19867-19870), a polyadenylation sequence, a pro-peptide sequence, a pre-pro-peptide sequence, a promoter, a signal sequence, and a transcription terminator. At a minimum, the control sequences include a promoter, and a transcriptional stop signal as well as translational start and stop signals. Control sequences may be optimized to their specific purpose. Preferred optimized control sequences used in the present invention are those described in WO2006/077258.

In order to facilitate expression, a nucleic acid of interest or encoding the polypeptide involved in the production of the compound of interest may be a synthetic polynucleotide. The synthetic polynucleotides may be optimized in codon use, preferably according to the methods described in WO2006/077258 or WO2008/000632. WO2008/000632 addresses codon-pair optimization. Codon-pair optimization is a method wherein the nucleotide sequences encoding a polypeptide have been modified with respect to their codon-usage, in particular the codon-pairs that are used, to obtain improved expression of the nucleotide sequence encoding the polypeptide and/or improved production of the encoded polypeptide. Codon pairs are defined as a set of two subsequent triplets (codons) in a coding sequence (CDS).

"Site-specific recombination", also known as conservative site-specific recombination, is a type of recombination in which nucleic acid strand exchange takes place between segments possessing only a limited degree of sequence homology. Site-specific recombinase enzymes perform rearrangements of nucleic acid segments by recognizing and binding to short DNA sequences ("site-specific recombination sites" herein), at which they cleave the DNA backbone, exchange the two DNA helices involved and rejoin the DNA strands. In some site-specific recombination systems having just a recombinase enzyme together with the recombination sites is enough to perform all these reactions, in some other systems a number of accessory proteins and accessory sites may also needed.

The site-specific recombination sites and recombinase are selected such that the recombinase may target the site-specific recombination sites leading to out-recombination (or removed or excised of the like) of sequence locate between the recombination sites.

The terms "recombinase" or "site-specific recombinase" or the like refers to enzymes or recombinases that recognize and bind to a short nucleic acid site or "site-specific recombinase site", i.e., a recombinase recognition site, and catalyze the recombination of nucleic acid in relation to these sites. These enzymes include recombinases, transposases and integrases.

The recombinase may be a tyrosine recombinase or a serine recombinase. Typical examples of tyrosine recombinases are the well-known enzymes such as Cre (from the P1 phage), FLP (from yeast *S. cerevisiae*) and Λ integrase (from lambda phage) while famous serine recombinases include enzymes such as: gamma-delta resolvase (from the Tn1000 transposon), Tn3 resolvase (from the Tn3 transposon) and φC31 integrase (from the φC31 phage).

The "site-specific recombinase site" or the like refers to short nucleic acid sites or sequences, i.e., recombinase recognition sites, which are recognized by a sequence- or site-specific recombinase and which become the crossover regions during a site-specific recombination event. Recombination sites are typically between 30 and 200 nucleotides in length and consist of two motifs with a partial inverted-repeat symmetry, to which the recombinase binds, and which flank a central crossover sequence at which the recombination takes place. Examples of sequence-specific recombinase target sites include, but are not limited to, lox sites, att sites, dif sites and FRT sites.

The term "lox site" as used herein refers to a nucleotide sequence at which the product of the cre gene of bacteriophage P1, the Cre recombinase, can catalyze a site-specific recombination event. A variety of lox sites are known in the art, including the naturally occurring loxP, loxB, loxL and loxR, as well as a number of mutant, or variant, lox sites, such as lox66, lox71, loxP511, loxP514, loxΔ86, loxΔ117, loxC2, loxP2, loxP3 and lox P23.

The term "FRT site" as used herein refers to a nucleotide sequence at which the product of the FLP gene of the yeast 2 micron plasmid, FLP recombinase, can catalyze site-specific recombination.

The site-specific recombination sites may be such that out-recombination following recombinase expression gives rise to a single mutant site-specific recombination site at the target locus which is not recognized by the recombinase. In particular, the lox sites may be lox66 and lox 71 (Albert, H., Dale, E. C., Lee, E., & Ow, D. W. (1995). Site-specific integration of DNA into wild-type and mutant lox sites placed in the plant genome. *Plant Journal,* 7(4), 649-659).

The loci at which nucleic acids are introduced into a cell may be chromosomal or extra-chromosomal. Typically, the replacement/deletion construct will be introduced at a chromosomal location since it will be used to replace the endogenous copy of an essential nucleic acid. An integration construct, however, may be designed so that it integrates at a chromosomal locus or a non-chromosomal locus, for example into a plasmid or other episomal vector or an artificial chromosome. The locus chosen for integration of an integration construct will typically be one, the disruption of which leads to no lack of fitness of the host cell.

The nucleic acids introduced into a cell in the method of the invention may be targeted to a specific locus or may be incorporated randomly at a locus in the host cell. Typically, the replacement/deletion construct will be targeted so that its incorporation at a locus will result in replacement/deletion of an endogenous essential nucleic acid. However, the replacement/deletion construct may be randomly integrated in the host cell, but this would typically require a further step to remove the endogenous essential nucleic acid.

An integration construction may be targeted to a specific locus, for example one, the disruption of which, is known not to lead to loss of fitness of the host cell. However, random integration strategies may also be used.

Thus, the nucleic acids introduced into a cell in the method of the invention may comprise sequence allowing incorporation at a target locus, for example by homologous recombination. Thus, nucleic acids to be introduced typically comprise a sequence which recombines, for example by homologous recombination, with a sequence 5' of the target locus and a sequence which recombines, for example by homologous recombination, with a sequence 3' of the target locus.

Homologous recombination is a type of genetic recombination in which nucleotide sequences are exchanged between two similar or identical molecules of DNA. In the method of the invention, the sequences enabling homologous recombination may be from about 20 bp to about 500 kb in length.

The lengths of the sequences mediating homologous recombination between polynucleotide subgroups and with the target locus may be at least about 30 bp, preferably at least about 50 bp, preferably at least about 0.1 kb, even preferably at least about 0.2 kb, more preferably at least about 0.5 kb, even more preferably at least about 1 kb or most preferably at least about 2 kb.

It will be obvious to the skilled person that, in order to achieve homologous recombination via a double cross-over event, the sequences chosen for replacement and integration constructs for integration at a desired locus need to be present at both sides/ends of the construct and need to be substantially homologous to sequences at both sides of the first/target or subsequent target loci. Thus, the sequences capable of homologous recombination are typically provided such that they are located at the "5'" and "3'" ends of the replacement/integration construct.

With the term "substantially homologous" as used in this invention is meant that a first nucleic acid sequence has a degree of identity with a second nucleic acid sequence with which it is to be recombined of at least about 70%, at least about 80%, preferably at least about 90%, over a region of not more than about 3 kb, preferably not more than about 2 kb, more preferably not more than about 1 kb, even more preferably not more than about 0.5 kb, even more preferably not more than about 0.2 kb, even more preferably not more than about 0.1 kb, such not more than about 0.05 kb, for example not more than about 0.03 kb. The degree of required identity may thereby depend on the length of the substantially homologous sequence. The shorter the homologous sequence, the higher the percentage homology may be.

Alternatively, nucleic acids may be provide without sequences directing targeted integration, so that they are randomly incorporated in a host cell.

The method of the invention may be carried out in any suitable format. For example, the method may be carried out wherein a cell treated according to the method of the invention may be carried out in a conventional fashion in which transformed cells are streaked out on a solid medium. Only those cells which contain the further copy of the essential nucleic acid will be viable and thus form colonies.

Alternatively, the method of the invention may be carried out in liquid media. This is not typically possible using conventional transformation protocols in view of cross-feeding effects. However, the method of the invention is advantageous because it eliminates cross-feeding effects seen in conventional transformation techniques and, accordingly, the method of the invention may be carried out in liquid medium. Only those cells carrying a further copy of the essential nucleic acid will be viable and capable of dividing.

The host cell may be any host cell. The host cell may be a prokaryotic cell, an archaeal cell or a eukaryotic host cell.

A host cell suitable for use in the method according to the invention may be a prokaryotic cell. Preferably, the prokaryotic host cell is a bacterial cell. The term "bacterial cell" includes both Gram-negative and Gram-positive microorganisms. Suitable bacteria may be selected from e.g. *Escherichia, Anabaena, Caulobactert, Gluconobacter, Rhodobacter, Pseudomonas, Paracoccus, Bacillus, Brevibacterium, Corynebacterium, Rhizobium (Sinorhizobium), Flavobacterium, Klebsiella, Enterobacter, Lactobacillus, Lactococcus, Methylobacterium, Staphylococcus* or *Streptomyces*. Preferably, the bacterial cell is selected from the group consisting of *B. subtilis, B. amyloliquefaciens, B. licheniformis, B. puntis, B. megaterium, B. halodurans, B. pumilus, G. oxydans, Caulobactert crescentus* CB 15, *Methylobacterium extorquens, Rhodobacter sphaeroides, Pseudomonas zeaxanthinifaciens, Paracoccus denitrificans, E. coli, C. glutamicum, Staphylococcus carnosus, Streptomyces lividans, Sinorhizobium melioti* and *Rhizobium radiobacter*.

Preferably, the eukaryotic cell is a mammalian, insect, plant, fungal, or algal cell. Preferred mammalian cells include e.g. Chinese hamster ovary (CHO) cells, COS cells, 293 cells, PerC6 cells, and hybridomas. Preferred insect cells include e.g. Sf9 and Sf21 cells and derivatives thereof. More preferably, the eukaryotic cell is a fungal cell, e.g. a yeast cell, such as *Candida, Hansenula, Kluyveromyces, Pichia, Saccharomyces, Schizosaccharomyces,* or *Yarrowia* strain. More preferably a *Kluyveromyces lactis, Saccharomyces cerevisiae, Hansenula polymorpha, Yarrowia lipolytica* or *Pichia pastoris*, or a filamentous fungal cell. Most preferably, the eukaryotic cell is a filamentous fungal cell.

"Filamentous fungi" include all filamentous forms of the subdivision Eumycota and Oomycota (as defined by Hawksworth et al., In, Ainsworth and Bisby's Dictionary of The Fungi, 8th edition, 1995, CAB International, University Press, Cambridge, UK). The filamentous fungi are characterized by a mycelial wall composed of chitin, cellulose, glucan, chitosan, mannan, and other complex polysaccharides. Vegetative growth is by hyphal elongation. Filamentous fungal strains include, but are not limited to, strains of *Acremonium, Agaricus, Aspergillus, Aureobasidium, Chrysosporium, Coprinus, Cryptococcus, Filibasidium, Fusarium, Geosmithia, Humicola, Magnaporthe, Mucor, Myceliophthora, Neocallimastix, Neurospora, Paecilomyces, Penicillium, Piromyces, Panerochaete, Pleurotus, Rasamsonia, Schizophyllum, Talaromyces, Thermoascus, Thermomyces, Thielavia, Tolypocladium,* and *Trichoderma*.

Preferred filamentous fungal cells belong to a species of an *Acremonium, Aspergillus, Chrysosporium, Myceliophthora, Penicillium, Rasamsonia, Talaromyces, Thielavia, Fusarium* or *Trichoderma* genus, and even more preferably a species of *Aspergillus niger, Acremonium alabamense, Acremonium chrysogenum, Aspergillus awamori, Aspergillus foetidus, Aspergillus sojae, Aspergillus fumigatus, Talaromyces emersonii, Talaromyces thermophilus, Thermomyces lanuginosus, Thermoascus thermophilus, Thermoascus aurantiacus, Thermoascus crustaceus, Rasamsonia emersonii, Rasamsonia byssochlamyoides, Rasamsonia argillacea, Rasamsonia brevistipitata, Rasamsonia cylindrospora, Aspergillus oryzae, Chrysosporium lucknowense, Fusarium oxysporum, Myceliophthora thermophila, Trichoderma reesei, Thielavia terrestris* or *Penicillium chrysogenum*. Most preferred species are *Aspergillus niger* or *Penicillium chrysogenum*. When the host cell is an *Aspergillus* host cell, the host cell preferably is CBS 513.88, CBS124.903 or a derivative thereof. When the host cell is a *Penicillium* host cell, the host cell is preferably *Penicillium chrysogenum* strain NRRL 1951 and Wisconsin 54-1255 and all industrial derivatives, in particular *Penicillium chrysogenum* strains DS54465 and DS61187. When the host cell belongs to the genus *Rasamsonia* also known as *Talaromyces*, more preferably the host cell belongs to the species *Talaromyces emersonii* also known as *Rasamsonia emersonii*. When the host cell according to the invention is a *Talaromyces emersonii* also known as *Rasamsonia emersonii* host cell, the host cell preferably is CBS 124.902 or a derivative thereof.

The *Rasamsonia emersonii* (*R. emersonii*) strains used herein are derived from ATCC16479, which is used as wild-type strain. ATCC16479 was formerly also known as *Talaromyces emersonii* and *Penicillium geosmithia emersonii*. Upon the use of the name *Rasamsonia emersonii* also *Talaromyces emersonii* is meant. Other strain designations of *R. emersonii* ATCC16479 are CBS393.64, IFO31232 and IM1116815.

*Rasamsonia* (*Talaromyces*) *emersonii* strain TEC-142 is deposited at CENTRAAL BUREAU VOOR SCHIMMELCULTURES, Uppsalalaan 8, P.O. Box 85167, NL-3508 AD Utrecht, The Netherlands on 1 Jul. 2009 having the Accession Number CBS 124902. TEC-142S is a single isolate of TEC-142.

Such strains are suitable for use in the invention.

Several strains of filamentous fungi are readily accessible to the public in a number of culture collections, such as the American Type Culture Collection (ATCC), Deutsche Sammlung von Mikroorganismen und Zellkulturen GmbH (DSM), Centraalbureau Voor Schimmelcultures (CBS), and Agricultural Research Service Patent Culture Collection, Northern Regional Research Center (NRRL) *Aspergillus niger* CBS 513.88, *Aspergillus oryzae* ATCC 20423, IFO 4177, ATCC 1011, ATCC 9576, ATCC14488-14491, ATCC 11601, ATCC12892, *P. chrysogenum* CBS 455.95, *Penicillium citrinum* ATCC 38065, *Penicillium chrysogenum* P2, *Talaromyces emersonii* CBS 124.902, *Acremonium chrysogenum* ATCC 36225 or ATCC 48272, *Trichoderma reesei* ATCC 26921 or ATCC 56765 or ATCC 26921, *Aspergillus sojae* ATCC11906, *Chrysosporium lucknowense* C1, Garg 27K, VKM-F 3500 D, ATCC44006 and derivatives thereof.

When the host cell is a filamentous fungal host cell, in particular *A. niger*, the host cell may additionally comprise modifications in its genome such that it is deficient in at least one of glucoamylase (glaA), acid stable alpha-amylase (amyA), neutral alpha-amylase (amyBI and amyBII), oxalic acid hydrolase (oahA), a toxin, such as ochratoxin and fumonisin, and protease transcriptional regulator PrtT. Preferably, the host cell additionally comprises a disruption of the pepA gene encoding the major extracellular aspartic protease PepA.

Preferably, the host cell additionally comprises a modification of Sec61. A preferred Sec61 modification is a modification which results in a one-way mutant of Sec61; i.e. a mutant wherein the de novo synthesized protein can enter the ER via Sec61, but the protein cannot leave the ER via Sec61. Such modifications are extensively described in WO2005/123763. Most preferably, the Sec 61 modification is the S376W mutation in which Serine 376 is replaced by Tryptophan. These and other possible host modifications are also described in WO2012/001169, WO2011/009700, WO2007/062936, WO2006/040312 or WO2004/070022.

In one embodiment, the host cell according to the invention is, preferably inducibly, increased in its efficiency of homologous recombination (HR) as defined earlier herein in the section "vector-host system". The host cell is preferably decreased in its efficiency of non-homologous recombination (NHR). The ratio of non-homologous recombination/homologous recombination (NHR/HR) will typically be decreased in a preferred host cell of the invention.

Host cells having a decreased NHR/HR ratio as compared to a parent cell may be obtained by modifying the parent eukaryotic cell by increasing the efficiency of the HR pathway and/or by decreasing the efficiency of the NHR pathway. Preferably, the NHR/HR ratio thereby is decreased at least twice, preferably at least 4 times, more preferably at least 10 times. Preferably, the NHR/HR ratio is decreased in the host cell of the vector-host system according to the invention as compared to a parent host cell by at least 5%, more preferably at least 10%, even more preferably at least 20%, even more preferably at least 30%, even more preferably at least 40%, even more preferably at least 50%, even more preferably at least 60%, even more preferably at least 70%, even more preferably at least 80%, even more preferably at least 90% and most preferably by at least 100%.

Introduction of nucleic acids, such as a replacement/deletion and/or integration construct, into a host cell is preferably performed by techniques well known in the art (see Sambrook & Russell; Ausubel, supra). Introduction of nucleic acid may involve a process consisting of protoplast formation, transformation of the protoplasts, and regeneration of the cell wall in a manner known per se. Suitable procedures for introduction of nucleic acids into of *Aspergillus, Penicillium* and *Rasamsonia* cells are described in EP 238 023 and Yelton et al., 1984, Proceedings of the National Academy of Sciences USA 81:1470-1474 and Cantoral et al., 1987; Bio/Technol. 5: 494-497. Suitable procedures for transformation of *Aspergillus* and other filamentous fungal host cells using *Agrobacterium tumefaciens* are described in e.g. De Groot et al., *Agrobacterium tumefaciens*-mediated transformation of filamentous fungi. Nat Biotechnol. 1998, 16:839-842. Erratum in: Nat Biotechnol 1998 16:1074. A suitable method of transforming *Fusarium* species is described by Malardier et al., 1989, Gene 78:147156 or in WO 96/00787. Other methods can be applied such as a method using biolistic transformation as described in: Christiansen et al., *Biolistic transformation of the obligate plant pathogenic fungus, Erysiphe graminis* f.sp. *hordei*. 1995, Curr Genet. 29:100-102. Yeast may be transformed using the procedures described by Becker and Guarente, In Abelson, J. N. and Simon, M. I., editors, Guide to Yeast Genetics and Molecular Biology, Methods in Enzymology, Volume 194, pp 182-187, Academic Press, Inc., New York; Ito et al., 1983, Journal of Bacteriology 153: 163; and Hinnen et al., 1978, Proceedings of the National Academy of Sciences USA 75: 1920.

The transformation method of the invention may be used to generate a host cell which can conveniently be used for the production of a compound of interest. The host cell may already be capable to produce the compound of interest. The host cell may also be provided with a nucleic acid or nucleic acids of interest that encode(s) a polypeptide(s) involved in the production of the compound of interest.

Accordingly, the method according to the invention may comprise introduce of a nucleic acid of interest encoding a compound involved in the synthesis of the compound of interest. The nucleic acid may also directly encode a compound of interest.

More than one nucleic acid of interest may be introduced simultaneously into a host cell using the method of the invention. That is to say, an integration construct may comprise two or more nucleic acids of interest. For example, the nucleic acids of interest acids introduced into a cell on a single integration construct could encode some or all of the members of a biochemical/metabolic pathway. Alternatively, the nucleic acids could encode separate domains of a multidomain protein or the various polypeptide constituents of a multimeric protein.

If two or more nucleic acids are introduced simultaneously, for example on a single or different integration constructs, there is no requirement for multiple nucleic acids to encode polypeptides of the same pathway, or polypeptides which are functionally related. Thus, polypeptides encoded by nucleic acids of interest on an integration construct could be unrelated, for example relating to two unrelated functionalities to be expressed in a host cell.

The method of the invention may be carried out so that one integration construct results in knock-out of endogenous sequence from the host cell and a further integration may provide a nucleic acid of interest which is overexpressed. Thus, knock-out and overexpression may be carried out at the same time. A single integration construct may also be capable of achieving knock-out and overexpression at the same time.

The compound of interest according to the invention can be any biological compound. The biological compound may be biomass or any biopolymer or metabolite. The biological compound may be encoded by a single nucleic acid of interest or a series of nucleic acids composing a biosynthetic or metabolic pathway or may be the direct product of a single nucleic acid of interest or may be products of a series of nucleic acids of interest. The biological compound may be native to the host cell or heterologous. The biological compound may be modified according WO2010/102982.

The term "heterologous biological compound" is defined herein as a biological compound which is not native to the cell; or a native biological compound in which structural modifications have been made to alter the native biological compound.

The term "biopolymer" is defined herein as a chain (or polymer) of identical, similar, or dissimilar subunits (monomers). The biopolymer may be any biopolymer. The biopolymer may for example be, but is not limited to, a nucleic acid, polyamine, polyol, polypeptide (or polyamide), or polysaccharide.

The biopolymer may be a polypeptide. The polypeptide may be any polypeptide having a biological activity of interest. The term "polypeptide" is not meant herein to refer to a specific length of the encoded product and, therefore, encompasses peptides, oligopeptides, and proteins. Polypeptides further include naturally occurring allelic and engineered variations of the above-mentioned polypeptides and hybrid polypeptides. The polypeptides may be a modified polypeptide according WO2010/102982. The polypeptide may be native or may be heterologous to the host cell. The polypeptide may be a collagen or gelatin, or a variant or hybrid thereof. The polypeptide may be an antibody or parts thereof, an antigen, a clotting factor, an enzyme, a hormone or a hormone variant, a receptor or parts thereof, a regulatory protein, a structural protein, a reporter, or a transport protein, protein involved in secretion process, protein involved in folding process, chaperone, peptide amino acid transporter, glycosylation factor, transcription factor, synthetic peptide or oligopeptide, intracellular protein. The intracellular protein may be an enzyme such as, a protease, ceramidases, epoxide hydrolase, aminopeptidase, acylases, aldolase, hydroxylase, aminopeptidase, lipase, non-ribosomal synthetase or polyketide synthetase. The polypeptide may be an enzyme secreted extracellularly, such as an oxidoreductase, transferase, hydrolase, lyase, isomerase, catalase, cellulase, chitinase, cutinase, deoxyribonuclease, dextranase, esterase. The enzyme may be a carbohydrase, e.g. cellulases such as endoglucanases, β-glucanases, cellobiohydrolases or 3-glucosidases, GH61-enzymes, hemicellulases or pectinolytic enzymes such as xylanases, xylosidases, mannanases, galactanases, galactosidases, pectin methyl esterases, pectin lyases, pectate lyases, endo polygalacturonases, exopolygalacturonases rhamnogalacturonases, arabanases, arabinofuranosidases, arabinoxylan hydrolases, galacturonases, lyases, or amylolytic enzymes; hydrolase, isomerase, or ligase, phosphatases such as phytases, esterases such as lipases, phospholipases, galactolipases, proteolytic enzymes, dairy enzymes and products (e.g. chymosin, casein), oxidoreductases such as oxidases, transferases, or isomerases. The enzyme may be a phytase. The enzyme may be an aminopeptidase, asparaginase, amylase, carbohydrase, carboxypeptidase, endo-protease, metallo-protease, serine-protease, catalase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, protein deaminase, invertase, laccase, lipase, mannosidase, mutanase, oxidase, pectinolytic enzyme, peroxidase, phospholipase, polyphenoloxidase, ribonuclease, transglutaminase, or glucose oxidase, hexose oxidase, monooxygenase.

According to the present invention, a polypeptide can also be a fused or hybrid polypeptide to which another polypeptide is fused at the N-terminus or the C-terminus of the polypeptide or fragment thereof. A fused polypeptide is produced by fusing a nucleic acid sequence (or a portion thereof) encoding one polypeptide to a nucleic acid sequence (or a portion thereof) encoding another polypeptide.

Techniques for producing fusion polypeptides are known in the art, and include, ligating the coding sequences encoding the polypeptides so that they are in frame and expression of the fused polypeptide is under control of the same promoter (s) and terminator. The hybrid polypeptides may comprise a combination of partial or complete polypeptide sequences obtained from at least two different polypeptides wherein one or more may be heterologous to the host cell.

The biopolymer may be a polysaccharide. The polysaccharide may be any polysaccharide, including, but not limited to, a mucopolysaccharide (e. g., heparin and hyaluronic acid) and nitrogen-containing polysaccharide (eg., chitin). In a more preferred option, the polysaccharide is hyaluronic acid.

The polynucleotide of interest according to the invention may encode an enzyme involved in the synthesis of a primary or secondary metabolite, such as organic acids, carotenoids, antibiotics, anti-cancer drug, pigments isoprenoids, alcohols, fatty acids and vitamins. Such metabolite may be considered as a biological compound according to the present invention.

The term “metabolite” encompasses both primary and secondary metabolites; the metabolite may be any metabolite. Preferred metabolites are citric acid, gluconic acid and succinic acid, antibiotics, bioactive drugs, biofuels and building blocks of biomaterials.

The metabolite may be encoded by one or more genes, such as in a biosynthetic or metabolic pathway. Primary metabolites are products of primary or general metabolism of a cell, which are concerned with energy metabolism, growth, and structure. Secondary metabolites are products of secondary metabolism (see, for example, R. B. Herbert, The Biosynthesis of Secondary Metabolites, Chapman and Hall, New York, 1981).

The primary metabolite may be, but is not limited to, an amino acid, carboxylic acid, fatty acid, nucleoside, nucleotide, sugar, triglyceride, or vitamin.

The compounds of interest may be an organic compound selected from glucaric acid, gluconic acid, glutaric acid, adipic acid, succinic acid, tartaric acid, oxalic acid, acetic acid, lactic acid, formic acid, malic acid, maleic acid, malonic acid, citric acid, fumaric acid, itaconic acid, levulinic acid, xylonic acid, aconitic acid, ascorbic acid, kojic acid, coumeric acid, a poly unsaturated fatty acid, ethanol, 1,3-propane-diol, ethylene, glycerol, xylitol, carotene, astaxanthin, lycopene and lutein.

The secondary metabolite may be, but is not limited to, an alkaloid, coumarin, flavonoid, polyketide, quinine, steroid, peptide, or terpene, a β-lactam antibiotic such as Penicillin G or Penicillin V and fermentative derivatives thereof, a cephalosporin, cyclosporin or lovastatin. The secondary metabolite may be an antibiotic, antifeedant, attractant, bacteriocide, fungicide, hormone, insecticide, or rodenticide. Preferred antibiotics are cephalosporins and beta-lactams.

The invention also provides a host cell obtainable by a method according to the invention as herein described.

The invention also relates to a method for the production of a biological compound of interest, which method comprises culturing a host cell of the invention transformed with a nucleic acid encoding the biological compound of interest or a compound involved in the synthesis of the biological compound of interest under conditions conducive to the production of the biological compound of interest and, optionally, isolating the compound of interest from the culture broth.

A method for the production of a biological compound of interest, which method comprises transforming a host cell with a nucleic acid encoding the biological compound of interest or a compound involved in the synthesis of the biological compound of interest according to the method of the invention and culturing the resulting host cell under conditions conducive to the production of the biological compound of interest and optionally isolating the compound of interest from the culture broth.

Culturing as used herein means that the microbial cells are cultivated in a nutrient medium suitable for production of the biological compound of interest using methods known in the art. For example, the host cells may be cultivated by shake flask cultivation, small-scale or large-scale fermentation (including continuous, batch, fed-batch, or solid state fermentations) in laboratory or industrial fermentors performed in a suitable medium and under conditions allowing the compound of interest to be produced and, optionally, isolated. The cultivation takes place in a suitable nutrient medium comprising carbon and nitrogen sources and inorganic salts, using procedures known in the art (see, e. g., Bennett, J. W. and LaSure, L., eds., *More Gene Manipulations in Fungi*, Academic Press, CA, 1991). Suitable media are available from commercial suppliers or may be prepared using published compositions (e. g., in catalogues of the American Type Culture Collection). The system according to the present invention is stable and versatile enough to maintain the vector-host system on all kinds of media, including non-selective, complex media which are typically exploited in industrial fermentations. If the compound of interest is secreted into the nutrient medium, the compound can be isolated directly from the medium. If the compound of interest is not secreted, it can be isolated from cell lysates.

The biological compound of interest may be isolated by methods known in the art. For example, the biological compound of interest may be isolated from the nutrient medium by conventional procedures including, but not limited to, centrifugation, filtration, extraction, spray drying, evaporation, or precipitation. The isolated biological compound of interest may then be further purified by a variety of procedures known in the art including, but not limited to, chromatography (e. g., ion exchange, affinity, hydrophobic, chromatofocusing, and size exclusion), electrophoretic procedures (e.g., preparative isoelectric focusing, differential solubility (e. g., ammonium sulfate precipitation), or extraction (see, e.g., *Protein Purification*, J.-C. Janson and Lars Ryden, editors, VCH Publishers, New York, 1989). In some applications the biological compound of interest may be used without substantial isolation from the culture broth; separation of the culture medium from the biomass may be adequate.

Furthermore, standard molecular cloning techniques such as DNA isolation, gel electrophoresis, enzymatic restriction modifications of nucleic acids, Southern analyses, transformation of cells, etc., are known to the skilled person and are for example described by Sambrook et al. (1989) "Molecular Cloning: a laboratory manual", Cold Spring Harbor Laboratories, Cold Spring Harbor, N.Y. and Innis et al. (1990) "PCR protocols, a guide to methods and applications" Academic Press, San Diego.

A nucleic acid may be amplified using cDNA, mRNA or alternatively, genomic DNA, as a template and appropriate oligonucleotide primers according to standard PCR amplification techniques. The nucleic acid so amplified can be cloned into an appropriate vehicle and characterized by DNA sequence analysis.

The invention is further illustrated by the Examples:

EXAMPLES

Example 1: Preparation of TIF35 Deletion Constructs pDSM-Sc1, pDSM-An1 and pDSM-An1a Construct pDSM-Sc1 contains, from 5' site to 3' site, the following standardized elements and/or cassettes:

- 5' TIF35 region (SEQ ID NO 5)
- lox66 recombination site (included in SEQ ID NO 13)
- tet-on cassette: CMV promoter (SEQ ID NO 13), tet-on gene (SEQ ID NO 17), *Saccharomyces cerevisiae* (Sc) PGI1 terminator (SEQ ID NO 25)
- TetR::SSN6 cassette: *S. pombe* ADH1 promoter (SEQ ID NO: 75), TetR domain fused to SSN6 (SEQ ID NO: 76), *S. cerevisiae* SSN6 terminator (SEQ ID NO: 77)
- Cre cassette: tet-promoter (SEQ ID NO 8), Cre-recombinase gene (SEQ ID NO 73), ScADH2 terminator (SEQ ID NO 26)
- TIF35 cassette: *K. lactis* (Kl) promoter 10 (SEQ ID NO 11), codon variant of the Sc TIF35 gene (SEQ ID NO 16), Sc TAL1 terminator (SEQ ID NO 31)
- GFP cassette (optional): Kl promoter 2 (SEQ ID NO 10), codon optimized version of Venus GFP (SEQ ID NO 20), Sc TPI1 terminator (SEQ ID NO 33)
- KanMX cassette (optional): TEF1 promoter (SEQ ID NO 7), *Streptomyces kanamyceticus* (Sk) KanMX gene (SEQ ID NO 22), TEF1 terminator (SEQ ID NO 34)
- lox71 recombination site (included in SEQ ID NO 34)
- 3' TIF35 region (SEQ ID NO 6)

Construct pDSM-An1 contains, from 5'site to 3' site, the following standardized elements and/or cassettes:

- 5' TIF35 region (SEQ ID NO 37)
- lox66 recombination site (included in SEQ ID NO 43)
- tet-on cassette: *A. nidulans* gpdA promoter (SEQ ID NO 43), tet-on gene (SEQ ID NO 54), *Penicillium chrysogenum* (Pc) Pc21g01520 terminator (SEQ ID NO 63)
- Cre cassette: tet-promoter (SEQ ID NO 46), Cre-recombinase gene (SEQ ID NO 73), Pc PenDE terminator (SEQ ID NO 64)
- TIF35 cassette: Pc TIF35 promoter (SEQ ID NO 42), Pc TIF35 gene (SEQ ID NO 52), Pc TIF35 terminator (SEQ ID NO 62)
- GFP cassette (optional): An glaA promoter (SEQ ID NO 47), codon optimized version of Venus GFP (SEQ ID NO 57), *A. nidulans* AN7354 terminator (SEQ ID NO 65)
- phleomycin resistance cassette (optional): An MCP promoter (SEQ ID NO 49), *Streptoalloteichus hindustanus* (Sh) ble gene (SEQ ID NO 58), CYC1 terminator (SEQ ID NO 66)
- lox71 recombination site (included in SEQ ID NO 66)
- 3' TIF35 region (SEQ ID NO 38)

Construct pDSM-An1a contains the same elements and/or cassettes as construct pDSM-An1, except for the tet-on and Cre cassettes. The tet-on cassette is deleted and the Cre cassette is adapted with the xyn1 promoter:

- Cre* cassette: xyn1 promoter (SEQ ID NO 45), Cre-recombinase gene (SEQ ID NO 73), Pc PenDE terminator (SEQ ID NO 64)

All standardized elements are synthesized. The lox recombination sites are fused directly during synthesis to one of the neighboring elements. The cassettes are assembled from the respective standardized elements via Golden Gate cloning (Engler et al. 2008: A one pot, one step, precision cloning method with high throughput capability. PLoS ONE 3 (11): e3647). The resulting elements and cassettes will be further assembled into the final expression construct via recombination in yeast. Recombination in yeast is enabled through the use of connector sequences [see patent publication no. WO2013/076280 and co-pending patent application no. PCT/EP2013/056623] flanking the corresponding elements and cassettes. The yeast constructs are directly integrated into the yeast genome via recombination of the 5' and 3' TIF35 regions.

Constructs pDSM-An1 and pDSM-An1a will also be assembled via recombination in yeast, in combination with a selected backbone (bbn). In these cases, the constructs will form a plasmid.

Example 2: Preparation of Pathway Integration Constructs pDSM-Sc2 and pDSM-An2

Construct pDSM-Sc2 contains, from 5' site to 3' site, the following standardized elements and/or cassettes:

- 5'YPRC/TAU3
- LacZ cassette: Sc ENO1 promoter (SEQ ID NO 12), *E. coli* LacZ gene (SEQ ID NO 24), Sc PGI1 terminator (SEQ ID NO 25)
- Natamycin resistance cassette (optional): Kl promoter 1 (SEQ ID NO 9), *Streptomyces noursei* (Sn) nourseothricin acetyltransferase (SEQ ID NO 23), Sc TEF2 terminator (SEQ ID NO 32)

TIF35 cassette: *K. lactis* (Kl) promoter 10 (SEQ ID NO 11), ScTIF35 gene (SEQ ID NO 15), ScGPM1 terminator (SEQ ID NO 27)

lox66 recombination site (included in SEQ ID NO 13)

RFP cassette (optional): CMV promoter (SEQ ID NO 13), RFP gene (SEQ ID NO 21), Sc TEF2 terminator (SEQ ID NO 32)

HygroR cassette: Ag TEF1 promoter (SEQ ID NO: 7), HygroR marker gene (SEQ ID NO: 74, ScTEF1 terminator (SEQ ID NO: 34)

lox71 recombination site (included in SEQ ID NO 34)

3' YPRC/TAU3

Construct pDSM-An2 will contain from 5' site to 3' site the following standardized elements and/or cassettes:

5' amyB (SEQ ID NO 39)

amyB cassette: An TEF promoter (SEQ ID NO 51), amyB gene (SEQ ID NO 59), Pc Pc21g01520 terminator (SEQ ID NO 63)

TIF35 cassette: An THI promoter (SEQ ID NO 48), An TIF35 gene (SEQ ID NO 53), *A. nidulans* AN7354 terminator (SEQ ID NO 65)

Hygromycin B resistance cassette (optional): An MCP promoter (SEQ ID NO 49), HygB gene (SEQ ID NO 60), Pc PenDE terminator (SEQ ID NO 64)

lox66 recombination site (included in SEQ ID NO 43)

RFP cassette (optional): *A. nidulans* gpdA promoter (SEQ ID NO 43), DsRed-SKL (SEQ ID NO 61), CYC1 terminator (SEQ ID NO 66)

lox71 recombination site (included in SEQ ID NO 66)

3' amyB (SEQ ID NO 40)

The 5' YPRC/TAU3 region and 3' YPRC/TAU3 region from construct pDSM-Sc2 are amplified via PCR with primers with SEQ. ID NO 1 combined with 2, and 3 combined with 4, respectively. All other standardized elements are synthesized. The lox recombination sites will be fused directly during synthesis to one of the neighboring elements. The cassettes will be assembled from the respective standardized elements via Golden Gate cloning (Engler et al. 2008, supra). The resulting elements and cassettes will be further assembled into the final expression construct via recombination in yeast. Recombination in yeast is enabled through the use of connector sequences [see patent publication no. WO2013/076280 and co-pending patent application no. PCT/EP2013/056623] flanking the corresponding elements and cassettes. The yeast constructs will be directly integrated into the yeast genome via recombination over the 5' and 3' YPRC/TAU3 regions.

Construct pDSM-An2 is also assembled via recombination in yeast, in combination with a selected backbone (bbn). This construct will form a plasmid.

Example 3: Preparation of Pathway Integration Constructs pDSM-Sc3, pDSM-Sc3a, pDSM-An3 and pDSM-An3a Construct pDSM-Sc3 contains, from 5' site to 3' site, the following standardized elements and/or cassettes:

5'YPRC/TAU3

LacZ cassette: Sc ENO1 promoter (SEQ ID NO 12), *E. coli* LacZ gene (SEQ ID NO 24), Sc PGI1 terminator (SEQ ID NO 25)

lox66 recombination site (included in SEQ ID NO 13)

tet-off cassette: CMV promoter (SEQ ID NO 13), tet-off gene (SEQ ID NO 18), Sc PDC1 terminator (SEQ ID NO 28)

Cre cassette: tet-promoter (SEQ ID NO 8), Cre-recombinase gene (SEQ ID NO 73), Sc PGK1 terminator (SEQ ID NO 29)

TIF35 cassette: *K. lactis* (Kl) promoter 10 (SEQ ID NO 11), ScTIF35 gene (SEQ ID NO 15), Sc PMA1 terminator (SEQ ID NO 30)

RFP cassette (optional): TEF1 promoter (SEQ ID NO 7), RFP gene (SEQ ID NO 21), GPM1 terminator (SEQ ID NO 27)

Nourseothricin resistance cassette (optional): Kl promoter 1 (SEQ ID NO 9), *Streptomyces noursei* (Sn) nourseothricin acetyltransferase (SEQ ID NO 23), Sc TEF2 terminator (SEQ ID NO 35)

lox71 recombination site (included in SEQ ID NO 35)

3' YPRC/TAU3

Construct pDSM-Sc3a contains the same elements and cassettes as construct pDSM-Sc3, except for the lox recombination sites, which are replaced by FRT recombination sites and the Cre-recombinase gene, which is replaced by the Sc FLP (flipase) gene. SEQ ID NO 13 is replaced by SEQ ID NO 14; SEQ ID NO 73 is replaced by SEQ ID NO 19; SEQ ID NO 35 is replaced by SEQ ID NO 36.

Construct pDSM-An3 contains, from 5' site to 3' site, the following standardized elements and/or cassettes:

5' amyB (SEQ ID NO 39)

amyB cassette: An TEF promoter (SEQ ID NO 51), amyB gene (SEQ ID NO 59), Pc Pc21g01520 terminator (SEQ ID NO 63)

lox66 recombination site (included in SEQ ID NO 43)

tet-off cassette: *A. nidulans* gpdA promoter (SEQ ID NO 43, tet-off gene (SEQ ID NO 55), *Penicillium chrysogenum* (Pc) Pc20g11623 terminator (SEQ ID NO 69)

Cre cassette: tet-promoter (SEQ ID NO 46), Cre-recombinase gene (SEQ ID NO 73), Pc PenDE terminator (SEQ ID NO 64)

TIF35 cassette: An THI promoter (SEQ ID NO 48), An TIF35 gene (SEQ ID NO 53), *A. nidulans* AN7354 terminator (SEQ ID NO 65)

RFP cassette (optional): Pc PCB1 promoter (SEQ ID NO 50), DsRed-SKL (SEQ ID NO 61), *A. nidulans* AN4594 terminator (SEQ ID NO 68)

Hygromycin B resistance cassette (optional): An MCP promoter (SEQ ID NO 49), HygB gene (SEQ ID NO 60), CYC1 terminator (SEQ ID NO 66)

lox71 recombination site (included in SEQ ID NO 66)

3' amyB (SEQ ID NO 41)

Construct pDSM-An3a contains the same elements and cassettes as construct pDSM-An3, except for the lox recombination sites, which are replaced by FRT recombination sites and the Cre-recombinase gene, which is replaced by the Sc FLP (flipase) gene. SEQ ID NO 43 is replaced by SEQ ID NO 44; SEQ ID NO 73 is replaced by SEQ ID NO 56; SEQ ID NO 66 is replaced by SEQ ID NO 67.

The 5' YPRC/TAU3 region and 3' YPRC/TAU3 region from construct pDSM-Sc3 and -3a are amplified via PCR with primers with SEQ. ID NO 1 combined with 2, and 3 combined with 4, respectively. All other standardized elements are synthesized. The lox or FRT recombination sites will be fused directly during synthesis to one of the neighbouring elements. The cassettes will be assembled from the respective standardized elements via Golden Gate cloning (Engler et al. 2008, supra). The resulting elements and cassettes will be further assembled into the final expression construct via recombination in yeast. Recombination in yeast is enabled through the use of connector sequences [see patent publication no. WO2013/076280 and co-pending patent application no. PCT/EP2013/056623] flanking the corresponding elements and cassettes. The yeast constructs are directly integrated into the yeast genome via recombination over the 5' and 3' YPRC/TAU3 regions.

Constructs pDSM-An3 and pDSM-An3a are assembled via recombination in yeast, in combination with a selected backbone (bbn). These constructs will form a plasmid.

Example 4: Preparation of TIF35 Deletion Strains

A *Saccharomyces cerevisiae* TIF35 deletion strain is obtained via transformation of strain CenPK1137d with the elements and cassettes that form construct pDSM-Sc1. These elements and cassettes are assembled in vivo via recombination over connector sequences [see patent publication no. WO2013/076280 and co-pending patent application no. PCT/EP2013/056623] and integrated into the genome of strain CenPK1137d via recombination over the 5' TIF35 and 3' TIF35 regions. Transformant strains are selected via resistance towards kanamycin. Through the integration of construct pDSM-Sc1, the original Sc TIF35 gene is replaced by a codon variant between loxP recombination sites. The Cre-recombinase gene is also integrated, under control of the tet-on system (Meyer et al. 2011, supra: Fungal gene expression on demand: an inducible, tunable and metabolism-independent expression system for *Aspergillus niger*. Applied and environmental microbiology, vol. 77, no. 9, p. 2975-2983; Urlinger et al. 2000: Exploring the sequence space for tetracycline dependent transcriptional activators: novel mutations yield expanded range and sensitivity. PNAS, vol. 97, no. 14, p. 7963-7968; and Vogt et al. 2005: Doxycycline-regulated gene expression in the opportunistic fungal pathogen *Aspergillus fumigatus*. BMC Microbiology 5:1).

Correct replacement of the original TIF35 gene is verified by expression of the Cre-recombinase. This results in excision of the integrated TIF35 codon variant which, in turn, will lead to cell death in case the original TIF35 gene is replaced. Cre-recombinase expression is induced by addition of doxycycline. Alternatively, replacement of the original TIF35 gene may be verified by other methods known to a person skilled in the art, like PCR or Southern blot analysis. The resulting TIF35 deletion strain is designated CenPK1137d-delTIF35.

The *Aspergillus niger* TIF35 deletion strain is obtained via transformation of strain GBA-306 (see WO2011/09700) with the deletion cassette of construct pDSM-An1 or -An1a. This deletion cassette is either amplified via PCR (as complete cassette or as two separate fragments with a split marker approach (Catlett et al. 2003: Split-marker recombination for efficient targeted deletion of fungal genes. Fungal Genetics Newsletter 50, p. 9-11) or obtained via NotI restriction enzyme digestion from pDSM-An1. The original TIF35 gene is replaced by the Pc TIF35 gene through recombination of construct pDSM-An1 or -An1a with the 5' TIF35 and 3' TIF35 regions. The Pc TIF35 gene is placed between loxP recombination sites. The Cre-recombinase gene is also integrated, under control of the tet-on system (Meyer et al. 2011, supra; Urlinger et al. 2000, supra; Vogt et al. 2005, supra) or under control of the xylanase promoter. Transformant strains are selected via resistance towards phleomycin. True replacement of the original TIF35 gene is verified by expression of the Cre-recombinase. This results in excision of the integrated Pc TIF35 gene which, in turn, leads to cell death in case the original TIF35 gene is replaced. Cre-recombinase expression is induced by addition of doxycycline or xylose, respectively. Alternatively, replacement of the original TIF35 gene is verified by other methods known to a person skilled in the art, like PCR or Southern blot analysis. The resulting TIF35 deletion strain is designated GBA-306delTIF35.

Example 5: Integration of Pathway Integration Constructs pDSM-Sc2 and pDSM-An2; Excision of TIF35 Marker Gene Following Transformation Sc CenPK1137d-delTIF35 is transformed with pDSM-Sc2. The transformation mixture is cultivated on medium containing doxycycline to induce Cre-recombinase expression and excise the TIF35 gene from construct pDSM-Sc1. The resulting strains are cultivated on medium containing no antibiotic, G418, G418 and nourseothricin, nourseothricin. A comparison is made of the number of strains:

- No antibiotic: both strains from which the TIF35 gene from construct pDSM-Sc1 has been excised as strains in which no excision has occurred are able to grow
- Only G418 as antibiotic: only strains in which no excision has occurred are able to grow. Integration of pDSM-Sc2 may or may not have taken place
- G418 and nourseothricin added: only strains in which no excision has taken place and integration of pDSM-Sc2 has occurred are able to grow
- Only nourseothricin added: only strains in which integration of pDSM-Sc2 has taken place are able to grow. Excision of TIF35 from pDSM-Sc1 may or may not have taken place Desired strains are sensitive towards G418 and resistant to nourseothricin. The number and percentage of acquired desired strains may be calculated from the number of colonies present on the media described above.

An GBA-306delTIF35 is transformed with pDSM-An2. The transformation mixture is cultivated on medium containing doxycycline to induce Cre-recombinase expression and excise the TIF35 gene from construct pDSM-An1. If construct pDSM-An1a is used to create An GBA-306delTIF35, Cre-recombinase expression is induced with xylose. The resulting strains are cultivated on medium containing no antibiotic, phleomycin, phleomycin and hygromycin B, hygromycin B. A comparison will be made of the number of strains:

- No antibiotic: both strains from which the TIF35 gene from construct pDSM-An1 has been excised as strains in which no excision has occurred are able to grow
- Only phleomycin as antibiotic: only strains in which no excision has occurred are able to grow. Integration of pDSM-An2 may or may not have taken place
- Phleomycin and hygromycin B added: only strains in which no excision has taken place and integration of pDSM-An2 has occurred are able to grow
- Only hygromycin B added: only strains in which integration of pDSM-An2 has taken place are able to grow. Excision of TIF35 from pDSM-An1 may or may not have taken place Desired strains are sensitive towards phleomycin and resistant to hygromycin B. The number and percentage of acquired desired strains is calculated from the number of colonies present on the media described above.

Example 6: Integration of Pathway Integration Constructs pDSM-Sc2 and pDSM-An2; Excision of TIF35 Marker Gene Prior to Transformation Sc CenPK1137d-delTIF35 are transformed with pDSM-Sc2. Prior to transformation, directly after biomass formation, Cre-recombinase is induced through addition of doxycycline to excise the TIF35 gene from construct pDSM-Sc1. The transformation mixture is cultivated on medium containing no antibiotic, G418, G418 and nourseothricin, nourseothricin. A comparison is made of the number of strains:

No antibiotic: both strains from which the TIF35 gene from construct pDSM-Sc1 has been excised as strains in which no excision has occurred are able to grow Only G418 as antibiotic: only strains in which no excision has occurred are able to grow. Integration of pDSM-Sc2 may or may not have taken place G418 and nourseothricin added: only strains in which no excision has taken place and integration of pDSM-Sc2 has occurred are able to grow Only nourseothricin added: only strains in which integration of pDSM-Sc2 has taken place are able to grow. Excision of TIF35 from pDSM-Sc1 may or may not have taken place Desired strains are sensitive towards G418 and resistant to nourseothricin. The number and percentage of acquired desired strains is calculated from the number of colonies present on the media described above.

An GBA-3-6delTIF35 is transformed with pDSM-An2. Prior to transformation, directly after biomass formation, Cre-recombinase will be induced through addition of doxycycline to excise the TIF35 gene from construct pDSM-Sc1. The transformation mixture is cultivated on medium containing no antibiotic, phleomycin, phleomycin and hygromycin B, hygromycin B. A comparison is made of the number of strains:

No antibiotic: both strains from which the TIF35 gene from construct pDSM-An1 has been excised as strains in which no excision has occurred are able to grow Only phleomycin as antibiotic: only strains in which no excision has occurred are able to grow. Integration of pDSM-An2 may or may not have taken place Phleomycin and hygromycin B added: only strains in which no excision has taken place and integration of pDSM-An2 has occurred are able to grow Only hygromycin B added: only strains in which integration of pDSM-An2 has taken place are able to grow. Excision of TIF35 from pDSM-An1 may or may not have taken place Desired strains are sensitive towards phleomycin and resistant to hygromycin B. The number and percentage of acquired desired strains is calculated from the number of colonies present on the media described above.

Example 7: Integration of Pathway Deletion Constructs pDSM-Sc3 and pDSM-An3: Excision of TIF35 Marker Gene Following Transformation Sc CenPK1137d-delTIF35 will be transformed with pDSM-Sc3. The transformation mixture will be cultivated on medium containing doxycycline to induce Cre-recombinase expression and excise the TIF35 gene from construct pDSM-Sc1. The resulting strains is cultivated on medium containing no antibiotic, G418, G418 and nourseothricin, nourseothricin. A comparison will be made of the number of strains:

No antibiotic: both strains from which the TIF35 gene from construct pDSM-Sc1 has been excised as strains in which no excision has occurred are able to grow Only G418 as antibiotic: only strains in which no excision has occurred are able to grow. Integration of pDSM-Sc3 may or may not have taken place G418 and nourseothricin added: only strains in which no excision has taken place and integration of pDSM-Sc3 has occurred are able to grow Only nourseothricin added: only strains in which integration of pDSM-Sc3 has taken place are able to grow. Excision of TIF35 from pDSM-Sc1 may or may not have taken place. Excision of TIF35 from DSM-Sc3 should not have occurred Desired strains are sensitive towards G418 and resistant to nourseothricin. The number and percentage of acquired desired strains is calculated from the number of colonies present on the media described above.

An GBA-306delTIF35 is transformed with pDSM-An3. The transformation mixture will be cultivated on medium containing doxycycline to induce Cre-recombinase expression and excise the TIF35 gene from construct pDSM-An1. The resulting strains are cultivated on medium containing no antibiotic, phleomycin, phleomycin and hygromycin B, hygromycin B. A comparison is made of the number of strains:

No antibiotic: both strains from which the TIF35 gene from construct pDSM-An1 has been excised as strains in which no excision has occurred are able to grow Only phleomycin as antibiotic: only strains in which no excision has occurred are able to grow. Integration of pDSM-An3 may or may not have taken place Phleomycin and hygromycin B added: only strains in which no excision has taken place and integration of pDSM-An3 has occurred are able to grow Only hygromycin B added: only strains in which integration of pDSM-An3 has taken place are able to grow. Excision of TIF35 from pDSM-An1 may or may not have taken place. Excision of TIF35 from pDSM-An3 should not have occurred Desired strains are sensitive towards phleomycin and resistant to hygromycin B. The number and percentage of acquired desired strains is calculated from the number of colonies present on the media described above.

Example 8: Integration of Pathway Deletion Constructs pDSM-Sc3 and pDSM-An3: Excision of TIF35 Marker Gene Prior to Transformation Sc CenPK1137d-delTIF35 is transformed with pDSM-Sc3. The transformation mixture is cultivated on medium containing doxycycline to induce Cre-recombinase expression and excise the TIF35 gene from construct pDSM-Sc1. The resulting strains are cultivated on medium containing no antibiotic, G418, G418 and nourseothricin, nourseothricin. A comparison is made of the number of strains:

No antibiotic: both strains from which the TIF35 gene from construct pDSM-Sc1 has been excised as strains in which no excision has occurred are able to grow Only G418 as antibiotic: only strains in which no excision has occurred are able to grow. Integration of pDSM-Sc3 may or may not have taken place G418 and nourseothricin added: only strains in which no excision has taken place and integration of pDSM-Sc3 has occurred are able to grow Only nourseothricin added: only strains in which integration of pDSM-Sc3 has taken place are able to grow. Excision of TIF35 from pDSM-Sc1 may or may not have taken place Desired strains are sensitive towards G418 and resistant to nourseothricin. The number and percentage of acquired desired strains is calculated from the number of colonies present on the media described above.

An GBA-306delTIF35 is transformed with pDSM-An3. The transformation mixture is cultivated on medium containing doxycycline to induce Cre-recombinase expression and excise the TIF35 gene from construct pDSM-An1. The resulting strains are cultivated on medium containing no antibiotic, phleomycin, phleomycin and hygromycin B, hygromycin B. A comparison is made of the number of strains:

No antibiotic: both strains from which the TIF35 gene from construct pDSM-An1 has been excised as strains in which no excision has occurred are able to grow Only phleomycin as antibiotic: only strains in which no excision has occurred are able to grow. Integration of pDSM-An3 may or may not have taken place Phleomycin and hygromycin B added: only strains in which no excision has taken place and integration of pDSM-An3 has occurred are able to grow Only hygromycin B added: only strains in which integration of pDSM-An3 has taken place are able to grow. Excision of TIF35 from pDSM-An1 may or may not have taken place Desired strains are sensitive towards phleomycin and resistant to hygromycin B. The number and percentage of acquired desired strains is calculated from the number of colonies present on the media described above.

Example 9: Integration of Pathway Deletion Constructs pDSM-Sc3a and pDSM-An3a CenPK1137d-delTIF35 will be transformed with pDSM-Sc3a. Excision and integration will be performed as described in Example 5. The TIF35 gene from construct pDSM-Sc3a is stably maintained, since no lox recombination sites are present in this construct.

GBA-306delTIF35 is transformed with pDSM-An3a. Excision and integration will be performed as described in Example 5. The TIF35 gene from construct pDSM-An3a will be stably maintained, since no lox recombination sites are present in this construct.

Example 10: Iterative Transformation Rounds with Transformed Strains from Example 7 or 8

Transformed strains in which the TIF35 gene from construct pDSM-Sc1 is excised and the TIF35 gene from construct pDSM-Sc3 or pDSM-Sc3a is present are used for iterative transformation. These strains are cultivated in presence of doxycycline to suppress Cre-recombinase expression via the tet-off system (Meyer et al. 2011, supra; Urlinger et al. 2000, supra; Vogt et al. 2005, supra) and maintain the TIF35 marker. The subsequent pathway integration construct is targeted at a different integration site from pDSM-Sc3 in the host genome. This subsequent pathway integration construct contains, besides genes of interest, Cre-recombinase controlled by the tet-on system and the TIF35 selection marker between lox recombination sites like in construct pDSM-Sc1. Doxycycline is removed to induce excision of the TIF35 gene from construct pDSM-Sc3 or -3a. The additional antibiotic resistance markers are used to deduce the percentage successful excision of TIF35 from pDSM-Sc3 or -3a and maintenance of TIF35 from the next pathway integration construct. Iterative transformations can be performed via switching between tet-on and tet-off for induction of Cre-recombinase in each subsequent construct used for transformation. In addition, in each subsequent construct one may switch between Cre-recombinase including lox recombination sites and FLP recombinase including FRT recombination sites.

Example 11: Use of Pathway Integration Constructs Containing Only TIF35 as Selection Marker Pathway integration constructs pDSM-Sc2, pDSM-An2, pDSM-Sc3, pDSM-Sc3a, pDSM-An3 and pDSM-An3a optionally contain additional markers next to the TIF35 selection marker gene, such as genes for G418, nourseothricin, phleomycin and hygromycin B resistance and green fluorescent (GFP) and red fluorescent (RFP) protein. These genes are used only for testing purposes. Using the described principle of the TIF35 essential marker gene for transformant selection combined with recycling of the essential marker gene, the additional markers are not required. Upon transformation with pathway integration construct pDSM-Sc2, pDSM-An2, pDSM-Sc3, pDSM-Sc3a, pDSM-An3 or pDSM-An3a and induction of the Cre-recombinase for excision of the TIF35 gene from construct pDSM-Sc1, pDSM-An1 or pDSM-An1a, one can simply select for survivors. Surviving strains will be the transformed strains.

Example 12: Use of a TIF-35 Replacement Construct and Pathway Integration Construct in *S. cerevisiae*

12.1 Summary

The feasibility of using a one promoter (pGAL)/one recombinase (CRE) transformation system for the purpose of performing metabolic engineering in *S. cerevisiae* was tested.

This system consists of i) an essential gene as a marker and ii) GAL1 promoter regulated CRE recombinase embedded between two loxP sites. When transformation is coupled to CRE-mediated excision, different types of CRE-mediated excision events were observed in different yeast colonies, which is useful in the selection of diverse transformation events.

12.2 TIF-35 Replacement and Pathway Integration Constructs

Figure 8A:
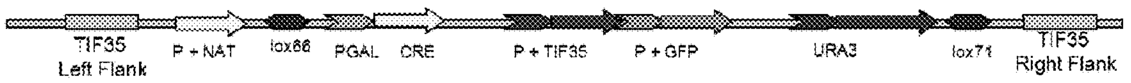

The structure of the basic TIF-35 replacement construct (referred to as the "replacement construct" hereafter) was as follows (and is set out schematically in FIG. 8*a*):

i) the essential gene, TIF35,
ii) CRE regulated by GAL promoter,
iii) URA3 and GFP as internal loxP marker, and
iv) NatR as external loxP marker.

This construct is similar to pDSM-Sc1 as described in Example 1, except that the Tet-on and TetR::SSN6 elements are replaced with the GAL1 promoter (SEQ ID NO: 80 to regulate CRE expression), the KanMX cassette is replaced by a URA3 cassette (SEQ ID NO: 78) and a NatR selectable marker cassette (SEQ ID NO: 79) is present between the 5'TIF35 flank and the lox66 site. All other elements are as described for pDSM-Sc1.

The elements of the construct were assembled as described in Example 1 for pDSM-Sc1. CENPK *S. cerevisiae* was used as the host strain and transformed using standard lithium acetate-based transformation to generate a strain comprising the replacement construct.

This strain was then transformed with seven DNA fragments in order to assemble a pathway integration construct in vivo in a *S. cerevisiae* strain comprising the replacement construct (as described in Example 2).

Figure 8B:

The pathway integration construct contains (as is set out schematically in FIG. 8*b*):

i) The essential gene, TIF35, (Note: situated external to the loxP sites), ii) LacZ as proof of principle metabolic engineered transgene, iii) kanMX4 and RFP as internal loxP marker, and iv) HygroR as external loxP marker.

This construct is the same as pDSM-Sc2 as described in Example 2, except that the Natamycin resistance cassette is replaced with a HygroR resistance cassette and the HygroR resistance cassette is replaced with a KanMX resistance cassette. The HygroR and KanMX cassettes are described in Examples 2 and 1 respectively.

When transformation is coupled to galactose induced CRE excision, several possible transformants scenarios could be envisioned, such as transformants with:

i) No CRE excision in the replacement and pathway integration constructs, ii) CRE excision in both the replacement and pathway integration constructs, iii) CRE excision only in the pathway integration, and iv) CRE excision only in the replacement.

Example 12.3

A yeast strain containing the replacement construct was grown in 2% glucose until an OD of ~1 OD/ml, followed by CRE induction in 2% galactose for 2 hour. Next, transformation was performed using the seven DNA fragments to generate the pathway integration construct. Following transformation, cells were grown in glucose without selection for 1.5 hour followed by plating onto hygromycin selective plate. 21 independent colonies were then streaked onto different selective plates for genotyping. The circled colony demonstrated the occurrence of excision of the replacement construct only, while the rectangle-shaped colony demonstrated excision of the pathway integration construct.

Example 12.4

A yeast strain containing the replacement construct was grown in 2% glucose until an OD of ~1 OD/ml. Next, transformation was performed using the seven DNA fragments to generate the bottom construct. In contrast to Example 12.3, galactose induction was performed only after transformation during the recovery period in 2% galactose for 1.5 hour followed by plating onto hygromycin selective plate. 21 independent colonies were then streaked onto different selective plates for genotyping. The rectangle-shaped colony demonstrated excision of the pathway integration constructs.

Example 12.5

A yeast strain containing the replacement construct was grown in 2% glucose until an OD of ~1 OD/ml. Next, transformation was performed using the seven DNA fragments to generate the bottom construct. As in Example 12.4, galactose induction was performed only after transformation during the recovery period in 2% galactose. In contrast to example 2, galactose induction duration was increased from 1.5 hour to overnight followed by plating onto hygromycin plates containing 2% galactose as selective plate. 21 independent colonies were then streaked onto different selective plates for genotyping. The dashed-lined rectangle, solid-lined rectangle, and oval-lined colonies demonstrated excision of the replacement construct only, pathway integration construct only, and both the replacement and pathway integration constructs, respectively.

Example 12.6 Determination of TIF35 and CRE-Dependent Lethality of Yeast Strain Containing the Replacement Construct We also characterized TIF35- and CRE-dependent lethality of a yeast strain containing the pathway integration construct. Different colonies of this strain were grown in YEP+2% glucose (as controls, should be viable) or in YEP+2% galactose (to induce CRE recombinase). About 1000 fold dilution of a 0.5 to 2 OD/ml of a 48 hr culture was plated out for independent transformation colonies. Upon GAL induction to induce CRE expression, colonies 8, 11, 15 and 23 (but not colony 12) significant loss of viability could be observed. For example, colonies 8 and 23 have good viability on glucose containing media, but no or relatively little colony forming units on galactose containing media. This experiment shows that galactose induction could cause the excision of essential gene TIF35, followed by the loss of viability of the cells. OD readings of these colonies were also monitored, and it was found that OD reading is not sufficient to determine viability, most likely because loss of cell viability depends on timing of CRE excision in the entire liquid population.

Example 12.7 Conclusion

In summary, yeast strains have been successfully created that serve as a foundation to probe both the one promoter (pGAL)/one recombinase (CRE). These yeast strains were used to test the lethality kinetics of the cells upon CRE-mediated excision of the TIF35 essential gene. Upon galactose induction, the majority of cells do indeed lose viability. It was found that upon galactose induction, either before or after yeast transformation, different types of CRE-mediated excision events were observed in different yeast colonies, which could be used to select for different types of transformants.

The invention claimed is:

1. A method for producing a biological compound of interest, which method comprises transforming a host cell with a nucleic acid encoding the biological compound of interest or a compound involved in synthesis of the biological compound of interest and culturing the resulting host cell under conditions conducive to production of the biological compound of interest, wherein the host cell is obtained by a method comprising:

providing a host cell comprising, at a first locus, at least two site-specific recombination sites and a nucleic acid having an essential function or encoding a product having an essential function;

introducing into the host cell, at a second locus, by homologous recombination, a further nucleic acid having the essential function or encoding for a product having the essential function together with the nucleic acid encoding the biological compound of interest or a compound involved in synthesis of the biological compound of interest; and carrying out recombination at the first locus via the at least two site-specific recombination sites, so that the nucleic acid having an essential function or encoding a product having an essential function, positioned at the first locus, is rendered non-functional, thereby to modify the host cell at the second locus, wherein the nucleic acid encoding the biological compound of interest or a compound involved in synthesis of the biological compound of interest is introduced at the second locus, wherein the host cell, when deficient in the nucleic acid having an essential function or encoding a product having an essential function, is non-viable under all conditions and on any medium.

2. The method according to claim 1, further comprising isolating the biological compound of interest from culture broth.

3. The method according to claim 1, wherein introduction into the host cell of the further nucleic acid having the essential function or encoding for a product having the essential function at the second locus results in replacement of nucleic acid sequence at the second locus with the further nucleic acid having the essential function or encoding for a product having the essential function.

4. The method according to claim 1, wherein at least two of the site-specific recombination sites flank the nucleic acid having an essential function or encoding a product having an essential function at the first locus.

5. The method according to claim 1, wherein at least two of the site-specific recombination sites flank a sequence encoding a recombinase, said recombinase recognizes at least two of the site-specific recombination sites.

6. The method according to claim 5, wherein the recombinase is tyrosine recombinase.

7. The method according to claim 5, wherein expression of the recombinase is under control of an inducible promoter.

8. The method according to claim 1, wherein the essential function is an essential function in fungi.

9. The method according to claim 1, wherein introducing into the host cell, at a second locus, a further nucleic acid having the essential function or encoding for a product having the essential function; and carrying out recombination at the first locus via the at least two site-specific recombination sites, so that the nucleic acid having an essential function or encoding a product having an essential function is rendered non-functional are carried out simultaneously, separately or sequentially.

10. The method according to claim 1, wherein a further copy of the essential nucleic acid is introduced at the locus together with at least two site-specific recombination sites.

11. The method according to claim 10, which further comprises:

introducing into the host cell, at a further second locus, a further copy of the nucleic acid having the essential function or encoding for a product having the essential function; and carrying out recombination at the second locus via the at least two site-specific recombination sites, so that the nucleic acid having an essential function or encoding a product having an essential function is rendered non-functional.

12. The method according to claim 11, which comprises one or more further cycles of:

introducing into the host cell, at a further second locus, a further copy of the nucleic acid having the essential function or encoding for a product having the essential function; and rendering non-functional the nucleic acid having an essential function or encoding a product having an essential function introduced in the previous introduction cycle via recombination of the at least two site-specific recombination sites flanking that essential gene.

13. The method according to claim 1, wherein the cell is a prokaryotic, archaeal or eukaryotic cell.

14. The method according to claim 1, wherein the host cell is a fungal cell.

15. The method according to claim 14, wherein the fungal cell is selected from the group consisting of an *Aspergillus* cell, a *Chrysosporium* cell, a *Penicillium* cell, a *Saccharomyces* cell, a *Rasamsonia* cell, a *Talaromyces* cell, and a *Trichoderma* cell.

16. The method according to claim 11, wherein introducing into the host cell, at a further second locus, of a further copy of the nucleic acid having the essential function or encoding for a product having the essential function occurs by introducing said sequence together with at least two site-specific recombination sites.

17. The method according to claim 12, wherein introducing into the host cell, at a further second locus, of a further copy of the nucleic acid having the essential function or encoding for a product having the essential function occurs by introducing said sequence together with at least two site-specific recombination sites.

18. A method for transformation of a host cell with a nucleic acid of interest, which method comprises:

providing a host cell comprising, at a first locus, at least two site-specific recombination sites flanking a nucleic acid having an essential function or encoding a product having an essential function;

introducing into the host cell, at a second locus, a nucleic acid of interest and a further nucleic acid having the essential function or encoding for a product having the essential function; and removing the nucleic acid having the essential function or encoding for a product having the essential function at the first locus via recombination of the at least two site-specific recombination sites, thereby to transform the host cell with a nucleic acid of interest, wherein the host cell, when deficient in the nucleic acid having an essential function or encoding a product having an essential function, is non-viable under all conditions and on any medium.

* * * * *

SEQUENCE LISTING

```
<160> NUMBER OF SEQ ID NOS: 80

<210> SEQ ID NO 1
<211> LENGTH: 23
<212> TYPE: DNA
<213> ORGANISM: Artificial Sequence
<220> FEATURE:
<223> OTHER INFORMATION: Primer 1 for amplification 5 YPRC/TAU3 region
      from Saccharomyces cerevisiae CenPK1137d
```

-continued

<400> SEQUENCE: 1
taaaggaggt gcacgcatta tgg 23

<210> SEQ ID NO 2
<211> LENGTH: 72
<212> TYPE: DNA
<213> ORGANISM: Artificial Sequence
<220> FEATURE:
<223> OTHER INFORMATION: Primer 2 for amplification 5 YPRC/TAU3 region from Saccharomyces cerevisiae CenPK1137d

<400> SEQUENCE: 2
aaacgcctgt gggtgtggta ctggatatgc aaagcgattg gaagtcgctt ttccaaggag 60
gtgaagaacg tc 72

<210> SEQ ID NO 3
<211> LENGTH: 71
<212> TYPE: DNA
<213> ORGANISM: Artificial Sequence
<220> FEATURE:
<223> OTHER INFORMATION: Primer1 for amplification 3 YPRC/TAU3 region from Saccharomyces cerevisiae CenPK1137d [ref]:

<400> SEQUENCE: 3
agaaagcctg tatgcgaagc cacaatcctt tccaacagac catactaagt gatgggacgt 60
cagcactgta c 71

<210> SEQ ID NO 4
<211> LENGTH: 20
<212> TYPE: DNA
<213> ORGANISM: Artificial Sequence
<220> FEATURE:
<223> OTHER INFORMATION: Primer2 for amplification 3 YPRC/TAU3 region from Saccharomyces cerevisiae CenPK1137d [ref]:

<400> SEQUENCE: 4
cccgtaatac aacagtgagc 20

<210> SEQ ID NO 5
<211> LENGTH: 650
<212> TYPE: DNA
<213> ORGANISM: Saccharomyces cerevisiae

<400> SEQUENCE: 5
gtggtggtgc ttcttatagc gccttagcgg gtattttcag tttctattcc tatagggatc 60
ctcagccttt gaagagttta gaaaccttca agaatagcgg gcgttatata ctgaacgatg 120
ccaagtgggg cgtcacagac cttgatgaag ctaaattgac aatatttcaa caagtagacg 180
cacctaaaag tcccaaagga gaaggcgtga cgtatttcat gagcggtgtt acagacgata 240
tgaaacaagc aagaagggaa caactcttag acgtatctct cctggacgtt catagagtcg 300
ccgaaaaata tctactaaac aaagaagggg tgagtacggt cattggacct ggaatcgagg 360
ggaagactgt ttcaccaaat tgggaggtga aggaactgta gatatataat ttaatcctgt 420
aaatatactg cttcaaagtt tcttgccgat ctatactcat cgcttgtaac gaagttaaaa 480
tttttttctt tcactgagtg tggaaagtga aaaattatca cgatggcaaa agagagggaa 540
gagaagccct agttactcgc tgtattgaaa ggatcaaaag accaaagacc accaggaata 600
aagcgacttc caatcgcttt gcatatccag taccacaccc acaggcgttt 650

<210> SEQ ID NO 6
<211> LENGTH: 650
<212> TYPE: DNA
<213> ORGANISM: Saccharomyces cerevisiae

<400> SEQUENCE: 6
agaaagcctg tatgcgaagc cacaatcctt tccaacagac catactaagt atgcacagaa 60
tatgctctgc acttgttttc taatgttact cttctcatat aaaaattgta gatattaaga 120
aagaaagtat gtaaactaat caatctatac ctaaaagaat attgttcaat attctataaa 180
gcacgcacgg catggtaaaa tttttaacga ttgtaagatt acaacaagtt gcaatccatt 240
caagctaaaa aatcaaagca aggaaaagct cagaggctgt cgtgaatatg tcaaataccg 300
taagagccat ttcaccagat ataacactat tcaacaagac attgacattc caagaaatct 360
cacaaaacac tagagaggct gtcatataca ttcatggagg tgcatggaac gatcctgaga 420
atacgcccaa tgattttaat caattagcca ataccatcaa atcaatggat actgagtcaa 480
cggtttgtca atactctata gaatacaggt tatcaccaga gatcacaaat ccaagaaact 540
tatatgatgc tgtgtcaaat ataacaaggc ttgttaaaga aaagggatta acgaacatta 600
atatggtggg acattccgtt ggagctacct ttatttggca gatattagct 650

<210> SEQ ID NO 7
<211> LENGTH: 390
<212> TYPE: DNA
<213> ORGANISM: Eremothecium gossypii

<400> SEQUENCE: 7
ggtctcggtg cgtccccgcc gggtcacccg gccagcgaca tggaggccca gaataccctc 60
cttgacagtc ttgacgtgcg cagctcaggg gcatgatgtg actgtcgccc gtacatttag 120
cccatacatc cccatgtata atcatttgca tccatacatt ttgatggccg cacggcgcga 180
agcaaaaatt acggctcctc gctgcagacc tgcgagcagg gaaacgctcc cctcacagac 240
gcgttgaatt gtccccacgc cgcgcccctg tagagaaata taaaaggtta ggatttgcca 300
ctgaggttct tctttcatat acttcctttt aaaatcttgc taggatacag ttctcacatc 360
acatccgaac ataaacaaca atgggagacc 390

<210> SEQ ID NO 8
<211> LENGTH: 728
<212> TYPE: DNA
<213> ORGANISM: Artificial Sequence
<220> FEATURE:
<223> OTHER INFORMATION: Tet-promoter for yeast

<400> SEQUENCE: 8
ggtctcggtg ccgcgccact tctaaataag cgaatttctt atgatttatg atttttatta 60
ttaaataagt tataaaaaaa ataagtgtat acaaatttta aagtgactct taggttttaa 120
aacgaaaatt cttattcttg agtaactctt tcctgtaggt caggttgctt tctcaggtat 180
agtatgaggt cgctcttatt gaccacacct ctaccggcag atccgctagg gataacaggg 240
taatatagat caattcctcg atcgagttta ccactcccta tcagtgatag agaaaagtga 300
aagtcgagtt taccactccc tatcagtgat agagaaaagt gaaagtcgag tttaccactc 360
cctatcagtg atagagaaaa gtgaaagtcg agtttaccac tccctatcag tgatagagaa 420
aagtgaaagt cgagtttacc actccctatc agtgatagag aaaagtgaaa gtcgagttta 480
ccactcccta tcagtgatag agaaaagtga aagtcgagtt taccactccc tatcagtgat 540

-continued agagaaaagt gaaagtcgag ctcggtaccc tatggcatgc atgtgctctg tatgtatata 600
aaactcttgt tttcttcttt tctctaaata ttctttcctt atacattagg tcctttgtag 660
cataaattac tatacttcta tagacacgca aacacaaata cacacactaa attaataaat 720
gggagacc 728

<210> SEQ ID NO 9
<211> LENGTH: 1021
<212> TYPE: DNA
<213> ORGANISM: Kluyveromyces lactis

<400> SEQUENCE: 9
ggtctcggtg ccgtatccct atctggatta acatcactgc cacagatcga attgcaagaa 60
gccacacttc acgtgatcca ctcgttcatc aggtttgtag cttcatggcg caggacttct 120
gatgatgaac tatctggctc atccggatgg atcacaagga tggataccct cagacagtac 180
gtttccgtat ggagcgatct tacaagaacc aacagttgat cctattactt tttttttatt 240
ttttgtccct ccgggatggc aagagggaca aagaagaatc ttcgttcttc tttcttgttc 300
tcaacttccc agcttccgtg tgattaccct ccgggacaac agaaaaactg gcattcggta 360
tcccgggaat ctgctgagaa ggaaagaaaa cgaaaaaaaa attgtacatt tgtgtcacat 420
tatgaattac aggaagtcag aaaacaggca gcacatgtct cgcacatgca tgtccatcag 480
acgagacatt atgagacatg cacgcgtgtg agagacatag caaaagtctc tccagtacac 540
acagaaagac acgttcacaa tccaggcacc ccacagagaa aaaaaaaaga agaagcccgg 600
aagctggcac gccatcatca accaccgctc ggtttacacg catcccaact gtcttttttt 660
tctggaatcc tataataact ggcatctgga aatcacgttg tatgttgcac catagtgact 720
ggctgtctga ctagcaaaca ttgattccct gattcccatt tggctcaatt ttgatgagaa 780
acagttgatt gattcttgtc aatttttttt tctttggacc accaccaacc aattgacatt 840
gaagtacttt cccatgattt gaggttatat aaaaggacgt tcaaatcact ttcaaggtta 900
attcagtttt gtcaattgat ttaagttcaa ttgttaacaa atttaattta attcgaaaca 960
aaccaaacca attcatttga attaacaaac caacccacaa aacaaaaaaa aatgggagac 1020
c 1021

<210> SEQ ID NO 10
<211> LENGTH: 1021
<212> TYPE: DNA
<213> ORGANISM: Kluyveromyces lactis

<400> SEQUENCE: 10
ggtctcggtg cgttcctcat cactagaagc cgaactgttg tcttcagtgg ggattggttc 60
gacattttgc caattgctgt cgatgtaccc tttcaaagcc atgtacctta aatcttcatc 120
cttggcaagt agattcatcg ggtgtgtttg aagtaagaat atttgcttgt ttttatggta 180
tcaaaggtat atgttgtaga agacaatttc cggtaatcca attgtctgtc tgctcagttt 240
agcacatgta tagtacgttg cacatagtct acaatattca gcattcagca ttcagtatac 300
agcatatggc taaatgatca caaatgtgat tgatgatttg acacgactag aaaagagaac 360
gaaaaaggga aattccatgt cacgtgcgtt ggcacgtgac atggaatatc gaagaaagaa 420
aaaaaaaacg atctcgtcct agtggaagcc cagagtctgg tccccccgga gtcttcccaa 480
aacaagaagc tgacacatgt tgacacagaa caccccacag caaatgcacc acgctacgta 540
gatcaggaag cttaactcta gcgacctgtc gctcgcccca cagaacctca cccgagaacc 600

-continued

```
acacattaca cgccgccagc tcccactata ctcatcttgc ttcccttaag cgttctcacg    660

attcgttcgc tgcccttctt caagagtctt ctgattctaa ttctcattcg aaatcctcta    720

cagttaatga attgcttgac atgacattca ttgtctcatg gttttggctt tttggctttt    780

gtcttttaaa gctatatcaa ctttacatat aaatatacgt caaaagggga ttcattaatt    840

agaaaattct ctttttcaat agttgctatt cattatcaat ctattcaact caattggtta    900

ttattttcat ctttttgtca tcctaaacca tcaacaatat ttaaatatat ctgttgctac    960

attaagagtt acttcagaaa taacaaaaaa atcgatcaag aattaataaa aatgggagac   1020

c                                                                   1021
```

<210> SEQ ID NO 11
<211> LENGTH: 1021
<212> TYPE: DNA
<213> ORGANISM: Kluyveromyces lactis

<400> SEQUENCE: 11

```
ggtctcggtg ctaggcaatt ggcatttttt cctccataca agttttttct aggcttttct     60

tctgccccac tgaaaaagat ccgcagctgc ctgtcttctt cacttttctc cgagtgatat    120

gcttcatcca ggctgccact tttctgttca tatcttcttc aaaatgatag gaatccagat    180

actctcttgt ggggtgcctt ttacctgtga tattcgatag caaaaaatgg gaagctcaca    240

gagtcaggct atttccacgt tagtggatgt cgcagccagt gggtccttct ttcacttgaa    300

ggctaccaat aatagacctt caatagtcac tatacggtct gtatggtctg tacgggtgta    360

tatggcacga tcaatatcgt accatattct gtcctgctct gttctggtag tctgcgtaaa    420

ctctgccaat tatgttcttc tatatccagt tctgtcgcat gtcggctaga ttatttgtcc    480

taagtttcga atggctggct gttccttggc ttctaatccc catatagaat ttaatcggtc    540

aagatggaac cgagcagttc cgattgatca gaccgtatcg atgcaacaac aggtgatgtt    600

gaattctgaa ttctgtcaaa gaatcacaat ctatctcgat ttcccttctt tctttttttt    660

cagcttagtt tagatatggg catcgaggtt cccctaaatt ttgtttgcca gctagacata    720

gcactggatt cttatactgt ctaaagctca ccacgggcct ggagaaaccg ttaaaggatg    780

cccccacaaa gttatagggt agaactatga aagtgatggg gttaggtttt tgaaaagaaa    840

tgaaattaga acttatataa ggggatggat tttagtatat tttccaattc tcttgttgag    900

atcgtaataa ttgtcgttct tccaatcaca tttagttaca taaatcacca tcagctatca    960

tactgaataa caagcaatca agctaaaaag aatatcaata ttaattaaaa aatgggagac   1020

c                                                                   1021
```

<210> SEQ ID NO 12
<211> LENGTH: 621
<212> TYPE: DNA
<213> ORGANISM: Saccharomyces cerevisiae

<400> SEQUENCE: 12

```
ggtctcggtg cccgcggaac cgccagatat tcattacttg acgcaaaagc gtttgaaata     60

atgacgaaaa agaaggaaga aaaaaaaaga aaaataccgc ttctaggcgg gttatctact    120

gatccgagct tccactagga tagcacccaa acacctgcat atttggacga cctttactta    180

caccaccaaa aaccactttc gcctctcccg cccctgataa cgtccactaa ttgagcgatt    240

acctgagcgg tcctcttttg tttgcagcat gagacttgca tactgcaaat cgtaagtagc    300

aacgtgtcaa ggtcaaaact gtatggaaac cttgtcacct cacttaattc tagctagcct    360
```

accctgcaag tcaagaggtg tccgtgattc ctagccacct caaggtatgc ctctccccgg 420
aaactgtggc cttttctggc acacatgatc tccacgattt caacatataa atagcttttg 480
ataatggcaa tattaatcaa atttatttta cttctttctt gtaacatctc tcttgtaatc 540
ccttattcct tctagctatt tttcataaaa aaccaagcaa ctgcttatca acacacaaac 600
actaaatcaa aatgggagac c 621

<210> SEQ ID NO 13
<211> LENGTH: 826
<212> TYPE: DNA
<213> ORGANISM: Artificial Sequence
<220> FEATURE:
<223> OTHER INFORMATION: CMV promoter fused to lox66 recombination site

<400> SEQUENCE: 13
ggtctcggtg ctaccgttcg tataatgtat gctatacgaa gttatgagct tggcccattg 60
catacgttgt atccatatca taatatgtac atttatattg gctcatgtcc aacattaccg 120
ccatgttgac attgattatt gactagttat taatagtaat caattacggg gtcattagtt 180
catagcccat atatggagtt ccgcgttaca taacttacgg taaatggccc gcctggctga 240
ccgcccaacg acccccgccc attgacgtca ataatgacgt atgttcccat agtaacgcca 300
atagggactt tccattgacg tcaatgggtg gagtatttac gctaaactgc ccacttggca 360
gtacatcaag tgtatcatat gccaagtacg ccccctattg acgtcaatga cggtaaatgg 420
cccgcctggc attatgccca gtacatgacc ttatgggact ttcctacttg gcagtacatc 480
tacgtattag tcatcgctat taccatggtg atgcggtttt ggcagtacat caatgggcgt 540
ggatagcggt ttgactcacg gggatttcca agtctccacc ccattgacgt caatgggagt 600
ttgttttggc accaaaatca acgggacttt ccaaaatgtc gtaacaactc cgccccattg 660
acgcaaatgg gcggtaggcg tgtacggtgg gaggtctata taagcagagc tcgtttagtg 720
aaccgtcaga tcgcctggac acgccatcca cgctgttttg acctccatag aagacaccgg 780
gaccgatcca gcctccgcgg cccgaattaa ttataaatgg gagacc 826

<210> SEQ ID NO 14
<211> LENGTH: 826
<212> TYPE: DNA
<213> ORGANISM: Artificial Sequence
<220> FEATURE:
<223> OTHER INFORMATION: CMV promoter fused to FRT recombination site

<400> SEQUENCE: 14
ggtctcggtg cgaagttcct attctctaga aagtatagga acttcgagct tggcccattg 60
catacgttgt atccatatca taatatgtac atttatattg gctcatgtcc aacattaccg 120
ccatgttgac attgattatt gactagttat taatagtaat caattacggg gtcattagtt 180
catagcccat atatggagtt ccgcgttaca taacttacgg taaatggccc gcctggctga 240
ccgcccaacg acccccgccc attgacgtca ataatgacgt atgttcccat agtaacgcca 300
atagggactt tccattgacg tcaatgggtg gagtatttac gctaaactgc ccacttggca 360
gtacatcaag tgtatcatat gccaagtacg ccccctattg acgtcaatga cggtaaatgg 420
cccgcctggc attatgccca gtacatgacc ttatgggact ttcctacttg gcagtacatc 480
tacgtattag tcatcgctat taccatggtg atgcggtttt ggcagtacat caatgggcgt 540
ggatagcggt ttgactcacg gggatttcca agtctccacc ccattgacgt caatgggagt 600
ttgttttggc accaaaatca acgggacttt ccaaaatgtc gtaacaactc cgccccattg 660

-continued

```
acgcaaatgg gcggtaggcg tgtacggtgg gaggtctata taagcagagc tcgtttagtg    720

aaccgtcaga tcgcctggac acgccatcca cgctgttttg acctccatag aagacaccgg    780

gaccgatcca gcctccgcgg cccgaattaa ttataaatgg gagacc                   826


<210> SEQ ID NO 15
<211> LENGTH: 841
<212> TYPE: DNA
<213> ORGANISM: Saccharomyces cerevisiae

<400> SEQUENCE: 15

ggtctcgaat gagtgaagtt gcaccagagg agatcataga gaatgcagat ggatctagat     60

ctatcattac atacaagatt gaagacggtg tcaagtataa gattactcag aaagtaaaag    120

aggttaaagt attggaaaaa gtccataaat ctgttgcaga aagaaaaaac tggcataaat    180

atggctctga aaaaggctct ccagcaggtc caagtgctgt tacagcaaga ttgggtgaag    240

aagtagaatt aagattgagt aggaactgga aacaagctga agaagaaaga atacaaaaag    300

aaaaggcaag tctcacaaag accggtctac aatgtagatt atgtggtaac gaccatatga    360

ccatgaactg tccattcaag acaattttaa gtgaactttc agcattagaa gacccagcca    420

ctaatgaagg cggtgtcgag gccgccagtg aagagaaggc aggccaagtt ggcggagctg    480

gttccatccc agggcagtat gttccacctt ctcgtcgtgc tggtgcaaga gatccttcat    540

ccgatgctta cagagactct agagaacgtg atgatatgtg tactttgaag attatgcaag    600

ttaatgaaaa tgccgatgaa aatagtttga gagaagagtt attgttccca ttcgcaccca    660

ttccaagagt ttctgtcgtt agaaacaaag aaacaggtaa atcaagagga ctcgcctttg    720

ttacctttc gagcgaagaa gttgccgaac aagctttacg tttcttggat ggtaggggtt     780

atatgaattt aattttacgt gttgaatggt ccaaacctaa ggttaaggaa taaaggagac    840

c                                                                    841


<210> SEQ ID NO 16
<211> LENGTH: 841
<212> TYPE: DNA
<213> ORGANISM: Saccharomyces cerevisiae

<400> SEQUENCE: 16

ggtctcgaat gtctgaggtt gctcctgagg agatcattga gaacgccgat ggcagccgct     60

ccatcatcac ctacaagatt gaggatggtg tcaagtacaa gatcacccag aaggtcaagg    120

aggtcaaggt cctcgagaag gtccacaagt ccgttgctga gcgcaagaac tggcacaagt    180

acggctccga gaagggctct cctgctggtc cttctgccgt cactgctcgt ctgggtgaag    240

aagttgagct tcgtctgtcc cgcaactgga agcaggctga ggaggagcgt atccagaagg    300

agaaggcctc cctgaccaag actggtctgc agtgccgtct gtgcggtaac gaccacatga    360

ccatgaactg ccccttcaag accatcctgt ctgagctttc tgccctcgaa gaccccgcca    420

ccaacgaggg tggtgttgag gctgcctccg aggagaaggc cggtcaggtt ggtggtgccg    480

gttccatccc cggccagtac gtgcctcctt cccgccgtgc tggtgctcgt gaccccagca    540

gcgatgccta ccgtgactcc cgcgagcgtg atgacatgtg caccctcaag atcatgcagg    600

tcaacgagaa cgccgacgag aactccctcc gcgaagaatt gctcttcccc ttcgctccca    660

tcccccgtgt ctccgttgtc cgcaacaagg agactggcaa gtcccgcggt cttgctttcg    720

tcaccttctc cagcgaagaa gtcgctgagc aggccctccg cttccttgac ggccgtggct    780
```

acatgaactt gattctccgt gttgaatgga gcaagcccaa ggtcaaggag taaaggagac 840
c 841

<210> SEQ ID NO 17
<211> LENGTH: 1024
<212> TYPE: DNA
<213> ORGANISM: Artificial Sequence
<220> FEATURE:
<223> OTHER INFORMATION: Tet-on gene yeast

<400> SEQUENCE: 17
ggtctcgaat gtctagatta gataaaagta aagtgattaa cagcgcatta gagctgctta 60
atgaggtcgg aatcgaaggt ttaacaaccc gtaaactcgc ccagaagctt ggtgtagagc 120
agcctacact gtattggcat gtaaaaaata agcgggcttt gctcgacgcc ttagccattg 180
agatgttaga taggcaccat actcactttt gccctttaaa aggggaaagc tggcaagatt 240
ttttacgcaa taacgctaaa agttttagat gtgctttact aagtcatcgc aatggagcaa 300
aagtacattc agatacacgg cctacagaaa aacagtatga aactctcgaa aatcaattag 360
cctttttatg ccaacaaggt tttcactag agaacgcgtt atatgcactc agcgctgtgg 420
ggcattttac tttaggttgc gtattggaag atcaagagca tcaagtcgct aaagaagaaa 480
gggaaacacc tactactgat agtatgccgc cattattacg acaagctatc gaattatttg 540
atcaccaagg tgcagagcca gccttcttat tcggccttga attgatcata tgcggattag 600
aaaaacaact taaatgtgaa agtgggtccg cgtacagccg cgcgcgtacg aaaaacaatt 660
acgggtctac catcgagggc ctgctcgatc tcccggacga cgacgccccc gaagaggcgg 720
ggctggcggc tccgcgcctg tcctttctcc ccgcgggaca cacgcgcaga ctgtcgacgg 780 ccccccccgac cgatgtcagc ctgggggacg agctccactt agacggcgag gacgtggcga 840
tggcgcatgc cgacgcgcta gacgatttcg atctggacat gttgggggac ggggattccc 900
cgggtccggg atttaccccc cacgactccg ccccctacgg cgctctggat atggccgact 960
tcgagtttga gcagatgttt accgatgccc ttggaattga cgagtacggt gggtaaagga 1020
gacc 1024

<210> SEQ ID NO 18
<211> LENGTH: 1024
<212> TYPE: DNA
<213> ORGANISM: Artificial Sequence
<220> FEATURE:
<223> OTHER INFORMATION: Tet-off gene yeast

<400> SEQUENCE: 18
ggtctcgaat gtctagatta gataaaagta aagtgattaa cagcgcatta gagctgctta 60
atgaggtcgg aatcgaaggt ttaacaaccc gtaaactcgc ccagaagcta ggtgtagagc 120
agcctacatt gtattggcat gtaaaaaata agcgggcttt gctcgacgcc ttagccattg 180
agatgttaga taggcaccat actcactttt gccctttaga aggggaaagc tggcaagatt 240
ttttacgtaa taacgctaaa agttttagat gtgctttact aagtcatcgc gatggagcaa 300
aagtacattt aggtacacgg cctacagaaa aacagtatga aactctcgaa aatcaattag 360
cctttttatg ccaacaaggt tttcactag agaatgcatt atatgcactc agcgctgtgg 420
ggcattttac tttaggttgc gtattggaag atcaagagca tcaagtcgct aaagaagaaa 480
gggaaacacc tactactgat agtatgccgc cattattacg acaagctatc gaattatttg 540
atcaccaagg tgcagagcca gccttcttat tcggccttga attgatcata tgcggattag 600
aaaaacaact taaatgtgaa agtgggtccg cgtacagccg cgcgcgtacg aaaaacaatt 660
acgggtctac catcgagggc ctgctcgatc tcccggacga cgacgccccc gaagaggcgg 720
ggctggcggc tccgcgcctg tcctttctcc ccgcgggaca cacgcgcaga ctgtcgacgg 780 ccccccgac cgatgtcagc ctgggggacg agctccactt agacggcgag gacgtggcga 840
tggcgcatgc cgacgcgcta gacgatttcg atctggacat gttgggggac ggggattccc 900
cgggtccggg atttaccccc cacgactccg ccccctacgg cgctctggat atggccgact 960
tcgagtttga gcagatgttt accgatgccc ttggaattga cgagtacggt gggtaaagga 1020
gacc 1024

<210> SEQ ID NO 19
<211> LENGTH: 1288
<212> TYPE: DNA
<213> ORGANISM: Saccharomyces cerevisiae

<400> SEQUENCE: 19
ggtctcgaat gccacaattt ggtatattat gtaaaacacc acctaaggtg cttgttcgtc 60
agtttgtgga aaggtttgaa agaccttcag gtgagaaaat agcattatgt gctgctgaac 120
taacctattt atgttggatg attacacata acggaacagc aatcaagaga gccacattca 180
tgagctataa tactatcata agcaattcgc tgagtttcga tattgtcaat aaatcactcc 240
agtttaaata caagacgcaa aaagcaacaa ttctggaagc ctcattaaag aaattgattc 300
ctgcttggga atttacaatt attccttact atggacaaaa acatcaatct gatatcactg 360
atattgtaag tagtttgcaa ttacagttcg aatcatcgga agaagcagat aagggaaata 420
gccacagtaa aaaaatgctt aaagcacttc taagtgaggg tgaaagcatc tgggagatca 480
ctgagaaaat actaaattcg tttgagtata cttcgagatt tacaaaaaca aaaactttat 540
accaattcct cttcctagct actttcatca attgtggaag attcagcgat attaagaacg 600
ttgatccgaa atcatttaaa ttagtccaaa ataagtatct gggagtaata atccagtgtt 660
tagtgacaga gacaaagaca agcgttagta ggcacatata cttctttagc gcaaggggta 720
ggatcgatcc acttgtatat ttggatgaat ttttgaggaa ttctgaacca gtcctaaaac 780
gagtaaatag gaccggcaat tcttcaagca ataaacagga ataccaatta ttaaaagata 840
acttagtcag atcgtacaat aaagctttga agaaaaatgc gccttattca atctttgcta 900
taaaaaatgg cccaaaatct cacattggaa gacatttgat gacctcattt ctttcaatga 960
agggcctaac ggagttgact aatgttgtgg gaaattggag cgataagcgt gcttctgccg 1020
tggccaggac aacgtatact catcagataa cagcaatacc tgatcactac ttcgcactag 1080
tttctcggta ctatgcatat gatccaatat caaaggaaat gatagcattg aaggatgaga 1140
ctaatccaat tgaggagtgg cagcatatag aacagctaaa gggtagtgct gaaggaagca 1200
tacgataccc cgcatggaat gggataatat cacaggaggt actagactac ctttcatcct 1260
acataaatag acgcatataa aggagacc 1288

<210> SEQ ID NO 20
<211> LENGTH: 733
<212> TYPE: DNA
<213> ORGANISM: Artificial Sequence
<220> FEATURE:
<223> OTHER INFORMATION: Sc Venus GFP -continued

<400> SEQUENCE: 20
ggtctcgaat gtctaaaggt gaagaattat tcactggtgt tgtcccaatt ttggttgaat 60
tagatggtga tgttaatggt cacaaatttt ctgtctccgg tgaaggtgaa ggtgatgcta 120
cttacggtaa attgacctta aaattgattt gtactactgg taaattgcca gttccatggc 180
caaccttagt cactacttta ggttatggtt tgcaatgttt tgctagatac ccagatcata 240
tgaaacaaca tgactttttc aagtctgcca tgccagaagg ttatgttcaa gaaagaacta 300
tttttttcaa agatgacggt aactacaaga ccagagctga agtcaagttt gaaggtgata 360
ccttagttaa tagaatcgaa ttaaaaggta ttgattttaa agaagatggt aacattttag 420
gtcacaaatt ggaatacaac tataactctc acaatgttta catcactgct gacaaacaaa 480
agaatggtat caaagctaac ttcaaaatta gacacaacat tgaagatggt ggtgttcaat 540
tagctgacca ttatcaacaa aatactccaa ttggtgatgg tccagtcttg ttaccagaca 600
accattactt atcctatcaa tctgccttat ccaaagatcc aaacgaaaag agagatcaca 660
tggtcttgtt agaatttgtt actgctgctg gtattaccca tggtatggat gaattgtaca 720
aataaaggag acc 733

<210> SEQ ID NO 21
<211> LENGTH: 727
<212> TYPE: DNA
<213> ORGANISM: Artificial Sequence
<220> FEATURE:
<223> OTHER INFORMATION: RFP

<400> SEQUENCE: 21
ggtctcgaat ggtaagtaag ggtgaagaag acaatatggc gatcattaag gaattcatgc 60
gtttcaaagt acacatggag ggaagcgtga acggacatga atttgaaatc gaaggggaag 120
gcgaaggtag accatacgaa ggaacccaga ccgcaaagct taaagttacc aaaggcgggc 180
cactaccatt tgcatgggat atcttgagcc ctcagtttat gtatggcagt aaggcctacg 240
ttaaacaccc agctgatatt cccgactatt tgaaattgtc ttttccagaa ggattcaaat 300
gggaaagagt aatgaatttc gaggacggcg gagttgttac tgttactcaa gattcaagtt 360
tgcaagacgg tgaatttatt tacaaggtca aattaagagg gactaatttc cctagtgatg 420
gtcccgtcat gcaaaagaag actatgggtt gggaagcctc atctgaacgt atgtatccag 480
aagatggcgc gcttaagggg gaaattaaac aaagattgaa gttaaaagac ggtggtcact 540
acgacgcgga agttaagacc acttataaag ctaaaaagcc cgttcagtta cctggtgcat 600
ataacgtaaa cattaaattg gatatcactt cacataatga agattacact attgtggaac 660
aatatgaaag agctgaaggt aggcactcaa cgggtggaat ggacgaattg tacaaataaa 720
ggagacc 727

<210> SEQ ID NO 22
<211> LENGTH: 826
<212> TYPE: DNA
<213> ORGANISM: Artificial Sequence
<220> FEATURE:
<223> OTHER INFORMATION: KanMX orf

<400> SEQUENCE: 22
ggtctcgaat gggtaaggaa aagactcacg tttcgaggcc gcgattaaat tccaacatgg 60
atgctgattt atatgggtat aaatgggctc gcgataatgt cgggcaatca ggtgcgacaa 120
tctatcgatt gtatgggaag cccgatgcgc cagagttgtt tctgaaacat ggcaaaggta 180

-continued

```
gcgttgccaa tgatgttaca gatgagatgg tcagactaaa ctggctgacg gaatttatgc    240

ctcttccgac catcaagcat tttatccgta ctcctgatga tgcatggtta ctcaccactg    300

cgatccccgg caaaacagca ttccaggtat tagaagaata tcctgattca ggtgaaaata    360

ttgttgatgc gctggcagtg ttcctgcgcc ggttgcattc gattcctgtt tgtaattgtc    420

cttttaacag cgatcgcgta tttcgtttgg ctcaggcgca atcacgaatg aataacggtt    480

tggttgatgc gagtgatttt gatgacgagc gtaatggctg gcctgttgaa caagtctgga    540

aagaaatgca taagcttttg ccattctcac cggattcagt cgtcactcat ggtgatttct    600

cacttgataa ccttattttt gacgagggga aattaatagg ttgtattgat gttggacgag    660

tcggaatcgc agaccgatac caggatcttg ccatcctatg gaactgcctc ggtgagtttt    720

ctccttcatt acagaaacgg ctttttcaaa aatatggtat tgataatcct gatatgaata    780

aattgcagtt tcatttgatg ctcgatgagt ttttctaaag gagacc                   826
```

<210> SEQ ID NO 23
<211> LENGTH: 589
<212> TYPE: DNA
<213> ORGANISM: Artificial Sequence
<220> FEATURE:
<223> OTHER INFORMATION: Sn nourseothricin acetyltransferase

<400> SEQUENCE: 23

```
ggtctcgaat gggtaccact cttgacgaca cggcttaccg gtaccgcacc agtgtcccgg     60

gggacgccga ggccatcgag gcactggatg ggtccttcac caccgacacc gtcttccgcg    120

tcaccgccac cggggacggc ttcaccctgc gggaggtgcc ggtggacccg cccctgacca    180

aggtgttccc cgacgacgaa tcggacgacg aatcggacga cggggaggac ggcgacccgg    240

actcccggac gttcgtcgcg tacggggacg acggcgacct ggcgggcttc gtggtcgtct    300

cgtactccgg ctggaaccgc cggctgaccg tcgaggacat cgaggtcgcc ccggagcacc    360

gggggcacgg ggtcgggcgc gcgttgatgg ggctcgcgac ggagttcgcc cgcgagcggg    420

gcgccgggca cctctggctg gaggtcacca acgtcaacgc accggcgatc cacgcgtacc    480

ggcggatggg gttcaccctc tgcggcctgg acaccgccct gtacgacggc accgcctcgg    540

acggcgagca ggcgctctac atgagcatgc cctgccccta aaggagacc                589
```

<210> SEQ ID NO 24
<211> LENGTH: 3091
<212> TYPE: DNA
<213> ORGANISM: Escherichia coli

<400> SEQUENCE: 24

```
ggtctcgaat gaccatgatt acggattcac tggccgtcgt tttacaacgt cgtgactggg     60

aaaaccctgg cgttacccaa cttaatcgcc ttgcagcaca tccccctttc gccagctggc    120

gtaatagcga agaggcccgc accgatcgcc cttcccaaca gttgcgcagc ctgaatggcg    180

aatggcgctt tgcctggttt ccggcaccag aagcggtgcc ggaaagctgg ctggagtgcg    240

atcttcctga ggccgatact gtcgtcgtcc cctcaaactg gcagatgcac ggttacgatg    300

cgcccatcta caccaacgtg acctatccca ttacggtcaa tccgccgttt gttcccacgg    360

agaatccgac gggttgttac tcgctcacat ttaatgttga tgaaagctgg ctacaggaag    420

gccagacgcg aattattttt gatggcgtta actcggcgtt tcatctgtgg tgcaacgggc    480

gctgggtcgg ttacggccag gacagtcgtt tgccgtctga atttgacctg agcgcatttt    540

tacgcgccgg agaaaaccgc ctcgcggtga tggtgctgcg ctggagtgac ggcagttatc    600
```

-continued

```
tggaagatca ggatatgtgg cggatgagcg gcattttccg tgacgtctcg ttgctgcata    660
aaccgactac acaaatcagc gatttccatg ttgccactcg ctttaatgat gatttcagcc    720
gcgctgtact ggaggctgaa gttcagatgt gcggcgagtt gcgtgactac ctacgggtaa    780
cagtttcttt atggcagggt gaaacgcagg tcgccagcgg caccgcgcct ttcggcggtg    840
aaattatcga tgagcgtggt ggttatgccg atcgcgtcac actacgtctg aacgtcgaaa    900
acccgaaact gtggagcgcc gaaatcccga atctctatcg tgcggtggtt gaactgcaca    960
ccgccgacgg cacgctgatt gaagcagaag cctgcgatgt cggtttccgc gaggtgcgga   1020
ttgaaaatgg tctgctgctg ctgaacggca agccgttgct gattcgaggc gttaaccgtc   1080
acgagcatca tcctctgcat ggtcaggtca tggatgagca gacgatggtg caggatatcc   1140
tgctgatgaa gcagaacaac tttaacgccg tgcgctgttc gcattatccg aaccatccgc   1200
tgtggtacac gctgtgcgac cgctacggcc tgtatgtggt ggatgaagcc aatattgaaa   1260
cccacggcat ggtgccaatg aatcgtctga ccgatgatcc gcgctggcta ccggcgatga   1320
gcgaacgcgt aacgcgaatg gtgcagcgcg atcgtaatca cccgagtgtg atcatctggt   1380
cgctggggaa tgaatcaggc cacggcgcta atcacgacgc gctgtatcgc tggatcaaat   1440
ctgtcgatcc ttcccgcccg gtgcagtatg aaggcggcgg agccgacacc acggccaccg   1500
atattatttg cccgatgtac gcgcgcgtgg atgaagacca gcccttcccg gctgtgccga   1560
aatggtccat caaaaaatgg ctttcgctac ctggagagac gcgcccgctg atcctttgcg   1620
aatacgccca cgcgatgggt aacagtcttg gcggtttcgc taaatactgg caggcgtttc   1680
gtcagtatcc ccgtttacag ggcggcttcg tctgggactg ggtggatcag tcgctgatta   1740
aatatgatga aaacggcaac ccgtggtcgg cttacggcgg tgattttggc gatacgccga   1800
acgatcgcca gttctgtatg aacggtctgg tctttgccga ccgcacgccg catccagcgc   1860
tgacggaagc aaaacaccag cagcagtttt tccagttccg tttatccggg caaaccatcg   1920
aagtgaccag cgaatacctg ttccgtcata gcgataacga gctcctgcac tggatggtgg   1980
cgctggatgg taagccgctg gcaagcggtg aagtgcctct ggatgtcgct ccacaaggta   2040
aacagttgat tgaactgcct gaactaccgc agccggagag cgccgggcaa ctctggctca   2100
cagtacgcgt agtgcaaccg aacgcgaccg catggtcaga agccggacac atcagcgcct   2160
ggcagcagtg gcgtctggct gaaaacctca gcgtgacact ccccgccgcg tcccacgcca   2220
tcccgcatct gaccaccagc gaaatggatt tttgcatcga gctgggtaat aagcgttggc   2280
aatttaaccg ccagtcaggc tttctttcac agatgtggat tggcgataaa aaacaactgc   2340
tgacgccgct gcgcgatcag ttcacccgtg caccgctgga taacgacatt ggcgtaagtg   2400
aagcgacccg cattgaccct aacgcctggg tcgaacgctg gaaggcggcg ggccattacc   2460
aggccgaagc agcgttgttg cagtgcacgg cagatacact tgctgatgcg gtgctgatta   2520
cgaccgctca cgcgtggcag catcagggga aaaccttatt tatcagccgg aaaacctacc   2580
ggattgatgg tagtggtcaa atggcgatta ccgttgatgt tgaagtggcg agcgatacac   2640
cgcatccggc gcggattggc ctgaactgcc agctggcgca ggtagcagag cgggtaaact   2700
ggctcggatt agggccgcaa gaaaactatc ccgaccgcct tactgccgcc tgttttgacc   2760
gctgggatct gccattgtca gacatgtata ccccgtacgt cttcccgagc gaaaacggtc   2820
tgcgctgcgg gacgcgcgaa ttgaattatg gcccacacca gtggcgcggc gacttccagt   2880
tcaacatcag ccgctacagt caacagcaac tgatggaaac cagccatcgc catctgctgc   2940
acgcggaaga aggcacatgg ctgaatatcg acggtttcca tatggggatt ggtggcgacg   3000
```

-continued actcctggag cccgtcagta tcggcggaat tccagctgag cgccggtcgc taccattacc 3060
agttggtctg gtgtcaaaaa taaaggagac c 3091

<210> SEQ ID NO 25
<211> LENGTH: 322
<212> TYPE: DNA
<213> ORGANISM: Saccharomyces cerevisiae

<400> SEQUENCE: 25
ggtctcgtaa aacaaatcgc tcttaaatat atacctaaag aacattaaag ctatattata 60
agcaaagata cgtaaatttt gcttatatta ttatacacat atcatatttc tatattttta 120
agatttggtt atataatgta cgtaatgcaa aggaaataaa ttttatacat tattgaacag 180
cgtccaagta actacattat gtgcactaat agtttagcgt cgtgaagact ttattgtgtc 240
gcgaaaagta aaaattttaa aaattagagc accttgaact tgcgaaaaag gttctcatca 300
actgtttaaa acctcggaga cc 322

<210> SEQ ID NO 26
<211> LENGTH: 322
<212> TYPE: DNA
<213> ORGANISM: Saccharomyces cerevisiae

<400> SEQUENCE: 26
ggtctcgtaa agcggatctc ttatgtcttt acgatttata gttttcatta tcaagtatgc 60
ctatattagt atatagcatc tttagatgac agtgttcgaa gtttcacgaa taaaagataa 120
tattctactt tttgctccca ccgcgtttgc tagcacgagt gaacaccatc cctcgcctgt 180
gagttgtacc cattcctcta aactgtagac atggtagctt cagcagtgtt cgttatgtac 240
ggcatcctcc aacaaacagt cggttatagt ttgtcctgct cctctgaatc gtgtccctcg 300
atatttctca tcctcggaga cc 322

<210> SEQ ID NO 27
<211> LENGTH: 322
<212> TYPE: DNA
<213> ORGANISM: Saccharomyces cerevisiae

<400> SEQUENCE: 27
ggtctcgtaa agtctgaaga atgaatgatt tgatgatttc tttttccctc catttttctt 60
actgaatata tcaatgatat agacttgtat agtttattat ttcaaattaa gtagctatat 120
atagtcaaga taacgtttgt ttgacacgat tacattattc gtcgacatct tttttcagcc 180
tgtcgtggta gcaatttgag gagtattatt aattgaatag gttcattttg cgctcgcata 240
aacagttttc gtcagggaca gtatgttgga atgagtggta attaatggtg acatgacatg 300
ttatagcaat acctcggaga cc 322

<210> SEQ ID NO 28
<211> LENGTH: 322
<212> TYPE: DNA
<213> ORGANISM: Saccharomyces cerevisiae

<400> SEQUENCE: 28
ggtctcgtaa agcgatttaa tctctaatta ttagttaaag ttttataagc atttttatgt 60
aacgaaaaat aaattggttc atattattac tgcactgtca cttaccatgg aaagaccaga 120
caagaagttg ccgacagtct gttgaattgg cctggttagg cttaagtctg ggtccgcttc 180
tttacaaatt tggagaattt ctcttaaacg atatgtatat tcttttcgtt ggaaaagatg 240

```
tcttccaaaa aaaaaaccga tgaattagtg gaaccaagga aaaaaaaaga ggtatccttg    300

attaaggaac acctcggaga cc                                             322


<210> SEQ ID NO 29
<211> LENGTH: 322
<212> TYPE: DNA
<213> ORGANISM: Saccharomyces cerevisiae

<400> SEQUENCE: 29

ggtctcgtaa aattgaattg aattgaaatc gatagatcaa tttttttctt ttctctttcc     60

ccatcccttta cgctaaaata atagtttatt ttatttttg aatatttttt atttatatac    120

gtatatatag actattattt atcttttaat gattattaag atttttatta aaaaaaaatt    180

cgctcctctt ttaatgcctt tatgcagttt ttttttccca ttcgatattt ctatgttcgg    240

gttcagcgta ttttaagttt aataactcga aaattctgcg ttcgttaaag ctttcgagaa    300

ggatattatt tcctcggaga cc                                             322


<210> SEQ ID NO 30
<211> LENGTH: 322
<212> TYPE: DNA
<213> ORGANISM: Saccharomyces cerevisiae

<400> SEQUENCE: 30

ggtctcgtaa atcctgttga agtagcattt aatcataatt tttgtcacat tttaatcaac     60

ttgatttttc tggtttaatt tttctaattt taattttaat ttttttatca atgggaactg    120

atacactaaa aagaattagg agccaacaag aataagccgc ttatttccta ctagagtttg    180

cttaaaattt catctcgaat tgtcattcta atattttatc cacacacaca ccttaaaatt    240

tttagattaa atggcatcaa ctcttagctt cacacacaca cacacaccga agctggttgt    300

tttatttgat tcctcggaga cc                                             322


<210> SEQ ID NO 31
<211> LENGTH: 322
<212> TYPE: DNA
<213> ORGANISM: Saccharomyces cerevisiae

<400> SEQUENCE: 31

ggtctcgtaa aggaagtatc tcggaaatat taatttaggc catgtcctta tgcacgtttc     60

ttttgatact tacgggtaca tgtacacaag tatatctata tatataaatt aatgaaaatc    120

ccctatttat atatatgact ttaacgagac agaacagttt tttatttttt atcctatttg    180

atgaatgata cagtttctta ttcacgtgtt atacccacac caaatccaat agcaataccg    240

gccatcacaa tcactgtttc ggcagcccct aagatcagac aaaacatccg gaaccacctt    300

aaatcaacgt ccctcggaga cc                                             322


<210> SEQ ID NO 32
<211> LENGTH: 322
<212> TYPE: DNA
<213> ORGANISM: Saccharomyces cerevisiae

<400> SEQUENCE: 32

ggtctcgtaa agagtaataa ttattgcttc catataatat ttttatatac ctcttatttt     60

tatgtattag ttaattaagt atttttatct atctgcttat cattttcttt tcatataggg    120

ggggttggtg ttttcttgcc catcagattg atgtcctcca actcggcact attttacaaa    180

gggttttttt gtaagagaag gagaagacag atactaaacc atacgttact cgaaacaaaa    240
```

```
aaaaaaaaaa tggaaaaagc tgctatcaac aaaagacggc ctcatcaaac ctaaagaaac    300

catgtcagcg tcctcggaga cc                                             322


<210> SEQ ID NO 33
<211> LENGTH: 322
<212> TYPE: DNA
<213> ORGANISM: Saccharomyces cerevisiae

<400> SEQUENCE: 33

ggtctcgtaa agattaatat aattatataa aaatattatc ttcttttctt tatatctagt     60

gttatgtaaa ataaattgat gactacggaa agctttttta tattgtttct ttttcattct    120

gagccactta aatttcgtga atgttcttgt aagggacggt agatttacaa gtgatacaac    180

aaaaagcaag gcgctttttc taataaaaag aagaaaagca tttaacaatt gaacacctct    240

atatcaacga agaatattac tttgtctcta aatccttgta aaatgtgtac gatctctata    300

tgggttactc acctcggaga cc                                             322


<210> SEQ ID NO 34
<211> LENGTH: 306
<212> TYPE: DNA
<213> ORGANISM: Artificial Sequence
<220> FEATURE:
<223> OTHER INFORMATION: TEF1 terminator fused to lox71 recombination
      site

<400> SEQUENCE: 34

ggtctcgtaa atcagtactg acaataaaaa gattcttgtt ttcaagaact tgtcatttgt     60

atagtttttt tatattgtag ttgttctatt ttaatcaaat gttagcgtga tttatatttt    120

ttttcgcctc gacatcatct gcccagatgc gaagttaagt gcgcagaaag taatatcatg    180

cgtcaatcgt atgtgaatgc tggtcgctat actgctgtcg attcgatact aacgccgcca    240

tccagtgtcg aaaacgagct cataacttcg tataatgtat gctatacgaa cggtacctcg    300

gagacc                                                               306


<210> SEQ ID NO 35
<211> LENGTH: 356
<212> TYPE: DNA
<213> ORGANISM: Artificial Sequence
<220> FEATURE:
<223> OTHER INFORMATION: Sc TEF2 terminator fused to lox71 recombination
      site

<400> SEQUENCE: 35

ggtctcgtaa agagtaataa ttattgcttc catataatat ttttatatac ctcttatttt     60

tatgtattag ttaattaagt atttttatct atctgcttat cattttcttt tcatataggg    120

ggggttggtg ttttcttgcc catcagattg atgtcctcca actcggcact attttacaaa    180

gggttttttt gtaagagaag gagaagacag atactaaacc atacgttact cgaaacaaaa    240

aaaaaaaaaa tggaaaaagc tgctatcaac aaaagacggc ctcatcaaac ctaaagaaac    300

catgtcagcg tataacttcg tataatgtat gctatacgaa cggtacctcg gagacc        356


<210> SEQ ID NO 36
<211> LENGTH: 356
<212> TYPE: DNA
<213> ORGANISM: Artificial Sequence
<220> FEATURE:
<223> OTHER INFORMATION: Sc TEF2 terminator fused to FRT recombination
      site
```

<400> SEQUENCE: 36
ggtctcgtaa agagtaataa ttattgcttc catataatat ttttatatac ctcttatttt 60
tatgtattag ttaattaagt atttttatct atctgcttat cattttcttt tcatataggg 120
ggggttggtg ttttcttgcc catcagattg atgtcctcca actcggcact attttacaaa 180
gggttttttt gtaagagaag gagaagacag atactaaacc atacgttact cgaaacaaaa 240
aaaaaaaaaa tggaaaaagc tgctatcaac aaaagacggc ctcatcaaac ctaaagaaac 300
catgtcagcg tgaagttcct attctctaga aagtatagga acttccctcg gagacc 356

<210> SEQ ID NO 37
<211> LENGTH: 1101
<212> TYPE: DNA
<213> ORGANISM: Aspergillus niger

<400> SEQUENCE: 37
aagcgacttc caatcgcttt gcatatccag taccacaccc acaggcgttt ctgttccagg 60
tatagcagac agccaggaag tcggggttcg tcgcggccga ttccgagtta ctggccaaga 120
gatgcagcaa ctgtttttgc ctatcctacg agacattgag gaccttgtcc gagagcagat 180
cgagacctct gacgctcagg taaaagcaat tttcctggtt ggagggtttg gacagagccc 240
ataccttcgc acatatcttc gcgactgctt ctctcctgaa gtcgaagtga tagcaccagt 300
tgacggctgg actgctgttg tcagaggcgc gttgacgaag actcttgggg aggtttccga 360
cacagagata aaaacatacg tcgattcccg aaaggcaagg gaaaactatg gaatgatttg 420
ttcgactaga ttcattgata aagtgcatga tgcaaagaag aagtaagtgg cgactgcctg 480
ctcaatgtgt tccagcatcc gtcttccatt tcttcgtccc agtggcctaa taattccagg 540
tactggaatg ccaaagaagg aaagttctat attgatgtta tgcattggtt tgtttccaag 600
gtatggaccg atattcgaac acacttctgg tctttgataa caagttcagg gggacgatat 660
cgaagaagcg aaggccatta agacgaactg gtctcagcat aagcttgcca aggacggcac 720
attcgactca atccgcgtca atctctacag gctcgatact cctatgggtg agaagccacc 780
gttgtacttc aatcgccgtg agtactctcg tgtagctgat tatggatgat gattatgagt 840
tattgacatt tcgttcttag acgtgaagca acatgccaag ttgaatccaa tccttaatca 900
gattgaaaag aatcgcatcc caatctgcca tggtgcagat aacgagctct actacacgat 960
cggatttcaa atccatgcgg tgtactattc cgctcactgt gaatacatgt tctggtatga 1020
aggctgcaat catggaagcg tcaaagccga attgcccatc gaacgtacaa gtactcctct 1080
gttctctcct tcctttgctt t 1101

<210> SEQ ID NO 38
<211> LENGTH: 1150
<212> TYPE: DNA
<213> ORGANISM: Aspergillus niger

<400> SEQUENCE: 38
gaaaccttcg aatccagcca gcatgtcgac acccacaaga tgtagtgcac tgacaccctt 60
gggtctcttt tcgtctggca ggcgggttct ccatccatcc acactttcca tggctgaaga 120
agatcttcat ctcatctatt gactactttt ctttgtactg tatgatccga tcgataatga 180
tgattactga agaaaaaaaa tgggggagga catcccaatg tgtgtgcgtg tgtcgtcttc 240
tctttgcttt ttgggtcgat ttgatacgaa gaaaagcagc gtggtctatt tgtcttattc 300

-continued

```
acgcactact cttttccggt tctatgtgtc tatttatcat gctgagttgc aagtcaaggc    360

aaggcaaggc aagcttgctt gcaagccctc ttttccttgt ttacttttcc gtgcattgat    420

cgatcgcggg tggaagtata cttagatcga gggagaaggt tcaaccccaa aaaacaaaag    480

tatttcaatt tgctcgttcg agtcacacta catggagtag agtagttagg taaaggttcg    540

gtcctgctta cttgggaacc tagtagtgct gtccaggttc taggacgggg aggaacaggt    600

tttattggct attggggtaa tgctccgtat tatcgtccgt tcagtactga cagcctggct    660

ggggtctact tttcaatcat atggtggatg ttgtagagcc tcttgcttgg tatatctcgg    720

gtaattggtt attagatcct tgctaagatg actcgatgcg tattagctga caagctcctc    780

tgatttggcg gcatgtgtca ggaaggcctg gatttgagcc acccgggacg cgacaaggca    840

gcattgactg tgctgatcag gctttgcaga gacgagatgc atggtggata atgaccatgg    900

gtctccagag tgcggaccaa cgagccaaga tcacggtcag tgtgtaggtg gttcgggggt    960

caacagctag ctgtctaggg acgtcaggga tgccgggaca ctgatcatga caataccgaa   1020

gggtgcctgt gtagtcgttt ggtaaagatg gaaggctggc tagtagcgtt tttgtatgag   1080

cttcgtcatg agtgtcatcg agaaagcctg tatgcgaagc cacaatcctt tccaacagac   1140

catactaagt                                                          1150


<210> SEQ ID NO 39
<211> LENGTH: 1162
<212> TYPE: DNA
<213> ORGANISM: Aspergillus niger

<400> SEQUENCE: 39

aagcgacttc caatcgcttt gcatatccag taccacaccc acaggcgttt atcttcgccc     60

agtgtgaact gggtgctaca gccaagtcct gttcagtgtc ctttgacaca gttcggttgt    120

tcagagttac cttccactca atagtataat gaatacaagg ctttcctcta tgttgcctcg    180

tagtcctttc ttcgggctcc tggaagaaac ccagatgatt gggctgggat tgatgcaagg    240

gagtataagg ttcatcaagt acatgttcag gtgatgggca aaatacggat ggcgtacgat    300

ctctaccgaa gtcaccaggg gtgggggcat acgatggagt ttgtatccac ggatcaggtg    360

gctgaagctg agaggcatcg tcatcgtagt aaggactaaa cgtcatcccc tcaaggcagt    420

agatgccact gagaagccta gtgttgggat catcatatgt tagcctacac catatgggtg    480

tcccagcaag agtgtccgtg agggaagagg tgcagctaac aaaaccagta aaatgatcag    540

gttcatggac aatgaactaa gacaggtaca gtattgtagc cctacccgtc ttggttaacc    600

tggtaaggtc aaaaaggatc gaaccgtggc tcagtacaaa caaaaggaat gttaacagtt    660

tgcgggagat gcaaggcaca tgctttgtca tgtttgacgc gtttgcagtg tagaagcttc    720

cagctaccgt agattactga tacaaactca atacactatt tctataacct tactgttcaa    780

tacagtacga tcaaaatttc cggaatatta atgttacggt taccttccat atgtagacta    840

gcgcacttgg cattagggtt cgaaatacga tcaaagagta ttgggggggg tgacagcagt    900

aatgactcca actgtaaatc ggcttctagg cgcgctccat ctaaatgttc tggctgtggt    960

gtacaggggc ataaaattac gcactacccg aatcgataga actactcatt tttatataga   1020

agtcagaatt catggtgttt tgatcatttt aaatttttat atggcgggtg gtgggcaact   1080

cgcttgcgcg ggcaactcgc ttaccgatta cgttgcccat cgaacgtaca agtactcctc   1140

tgttctctcc ttcctttgct tt                                            1162
```

<210> SEQ ID NO 40
<211> LENGTH: 1111
<212> TYPE: DNA
<213> ORGANISM: Aspergillus niger

<400> SEQUENCE: 40
aaataaccac aaacatcctt cccatatgct cggtcgtgct tgttgtacct tttggtgtcg 60
tcaagctcca gcagtgctgg ggcctcggct atgatatggt tagaatgctc ggggtgggtc 120
acggcaggac acccgacact gcaacgtcta ccacatttga gcgttattgg cagacttgcg 180
gcgagataac gaccgctagc ttgtatcaac caaatccaac tgaaattatt gctttgccat 240
cccaacagtg gatttcggag gagggagggg ggaagatata cgatgaacgg aagactggac 300
aagatacgtt acataaagca gtactacttg tttcaaactg tgtacacacc agggctctcg 360
cttcagcgga gagtgtcgaa agattcagta aaacatcgcc aggggtgatg gaaaggggtt 420
aagctagaca cagaaacata gaggaatcaa gaatgagaga agacgttgtg aagctttgtt 480
cgacgtattt cgcagagcat atttctgagc agcggacacg atttgtaacg tagccgtaga 540
ctcttgggac tgaagcttca cgaagggcag aagaaagtga agtgcagcgt ctgaatcgat 600
attctgccta tacagccgat agttttcccc tgaatctatc aaatggccaa gtgttcgcag 660
cacttctggg cgccttccgc ttaaacgtat gccctgaagg agcccagtga acgagtaaaa 720
atcgcgcagg cgataaaatt tctgcggtcg gtttagtatg aaccaaggca agggaaggag 780
ataattacca gcgccaattg atccaacttt agatacaaag ccggttcagt agctgagcat 840
tcctctgctg ctcggcaaat actgttccac cacctattca gagctgtcaa agggtcgccg 900
ctacccttct tcaccatttc gacggtgagc tcctgaaaga gggaaagagc tgctgccgta 960
agctctgctg ccagtgcctc cagttcctcc agctccgtgt ggtagagttt gtcaagaaat 1020
gcagtttgag tattgaagtc ttgcgaacag acaacttctg gagaaagcct gtatgcgaag 1080
ccacaatcct ttccaacaga ccatactaag t 1111

<210> SEQ ID NO 41
<211> LENGTH: 1111
<212> TYPE: DNA
<213> ORGANISM: Aspergillus niger

<400> SEQUENCE: 41
caacacacaa gttccgcaac gatcgaagca gagtcgagta catccagatg tttggtgtcg 60
tcaagctcca gcagtgctgg ggcctcggct atgatatggt tagaatgctc ggggtgggtc 120
acggcaggac acccgacact gcaacgtcta ccacatttga gcgttattgg cagacttgcg 180
gcgagataac gaccgctagc ttgtatcaac caaatccaac tgaaattatt gctttgccat 240
cccaacagtg gatttcggag gagggagggg ggaagatata cgatgaacgg aagactggac 300
aagatacgtt acataaagca gtactacttg tttcaaactg tgtacacacc agggctctcg 360
cttcagcgga gagtgtcgaa agattcagta aaacatcgcc aggggtgatg gaaaggggtt 420
aagctagaca cagaaacata gaggaatcaa gaatgagaga agacgttgtg aagctttgtt 480
cgacgtattt cgcagagcat atttctgagc agcggacacg atttgtaacg tagccgtaga 540
ctcttgggac tgaagcttca cgaagggcag aagaaagtga agtgcagcgt ctgaatcgat 600
attctgccta tacagccgat agttttcccc tgaatctatc aaatggccaa gtgttcgcag 660
cacttctggg cgccttccgc ttaaacgtat gccctgaagg agcccagtga acgagtaaaa 720
atcgcgcagg cgataaaatt tctgcggtcg gtttagtatg aaccaaggca agggaaggag 780

```
ataattacca gcgccaattg atccaacttt agatacaaag ccggttcagt agctgagcat    840
tcctctgctg ctcggcaaat actgttccac cacctattca gagctgtcaa agggtcgccg    900
ctacccttct tcaccatttc gacggtgagc tcctgaaaga gggaaagagc tgctgccgta    960
agctctgctg ccagtgcctc cagttcctcc agctccgtgt ggtagagttt gtcaagaaat   1020
gcagtttgag tattgaagtc ttgcgaacag acaacttctg gagaaagcct gtatgcgaag   1080
ccacaatcct ttccaacaga ccatactaag t                                  1111
```

```
<210> SEQ ID NO 42
<211> LENGTH: 1595
<212> TYPE: DNA
<213> ORGANISM: Penicillium chrysogenum

<400> SEQUENCE: 42

ggtctcggtg cgaggaagac gtgatcagag taagccctat gccaacagaa ggggaggatg     60
ggatcagagt aagacccatg tcagattctg caaacgaagg acggccgaaa ttacttgccg    120
cccccccccg gtgtatgtgg cctaagagaa gacacagtgt cttagacaat catattccca    180
gctcgtccat catctcatcg acatccttga ttggagcata cataccggaa tccaatcagt    240
gaattatgaa tgacacaacc actcagtttc ccacgattca tggtgtcggc aatcatctcc    300
cgggcgcaat ctcgccatgg gatactggat ggagagataa ccgagattcg gccggcttca    360
cttcaacttg catggctctg atgcaagatg tgtgcggatc agatctccta gccaaaggcc    420
cgcacattca acgtcgtgac tggcgtggcg cgaaggctat caaccttgtt gaccagatcc    480
cctcttgtca tcgagagcgg cagagaaggg aggctctctt gtcgaacaat ccggtcatgg    540
cattgagagc cagaagacat aggggttgaa tggcccctaa gttgaccaaa aatgtgagtg    600
tatcgatgtt tcagacagca atgccgattc gtcaagctga agaacccttg gaagcttcaa    660
ggacctgtca ggttgcatct ctctcggacg tgacccagtc tcagtcatcg ttagaatagg    720
aagaagttca gccctcaggt caaggatggt taatgcagtc agctctcgtt ggcctaaatg    780
atagttatgt acgccacggt attcttgtag ctggccttga agcttcagaa gactgcccac    840
gaaattagca gtatcaagtt cggcgcccgg acttcccatt tgggttctgt gataatttct    900
ttgatacgac agtcgttagg agccgatttt ttcttcctat tctttttccc ctgctgtgta    960
ggttggatgt tttcgtgagg gatgttggcc tgaaagagtt gaatgtcaaa tcaatcacta   1020
tcgttcgact gttcacccat gatgtcctcc agctcgccca tccggcgcgt cttcgaaacg   1080
gtgtgcttct gagcggccct ctgagaggcc gatgtactta gaaacatctc ccaataatct   1140
ggacctttaa ccgtgaatgt ttcacaacct tgatcagttt aaatgataaa tagtgacaca   1200
aggtgaagta cgagcccgga gatcagggcg aatgactact ctgcccgcta taagtattgg   1260
gtttggtccg aaggaactgt gttcggggcc tttaaagtta aatatttttg aaagcagcgc   1320
ttgcagagag tgttaatatt cggaccccgt tgaatgtcat gtttatcatt gggcaaacag   1380
tggagtggtg tcaatcttgt atcagtctag tagaaacgag gttaaagaac cttggaacta   1440
ctttagatgg ggctatacac accgcgccac gtgattcccg ccaccagcca caactgtgcc   1500
acagtaaatt attaaatcca caacggattc gcctttgaaa gaaatccaga aattcagcag   1560
ccgtaataac accatcactt acacaatggg agacc                              1595
```

```
<210> SEQ ID NO 43
<211> LENGTH: 854
<212> TYPE: DNA
<213> ORGANISM: Artificial Sequence
```

<220> FEATURE:
<223> OTHER INFORMATION: A. nidulans gpdA promoter fused to lox66
      recombination site

<400> SEQUENCE: 43
ggtctcggtg ctaccgttcg tataatgtat gctatacgaa gttatcagac agctctggcg     60
gctctgaggt gcagtggatg attattaatc cgggaccggc cgcccctccg ccccgaagtg    120
gaaaggctgg tgtgcccctc gttgaccaag aatctattgc atcatcggag aatatggagc    180
ttcatcgaat caccggcagt aagcgaagga gaatgtgaag ccaggggtgt atagccgtcg    240
gcgaaatagc atgccattaa cctaggtaca gaagtccaat tgcttccgat ctggtaaaag    300
attcacgaga tagtaccttc tccgaagtag gtagagcgag tacccggcgc gtaagctccc    360
taattggccc atccggcatc tgtagggcgt ccaaatatcg tgcctctcct gctttgcccg    420
gtgtatgaaa ccggaaaggc cgctcaggag ctggccagcg gcgcagaccg ggaacacaag    480
ctggcagtcg acccatccgg tgctctgcac tcgacctgct gaggtccctc agtccctggt    540
aggcagcttt gccccgtctg tccgcccggt gtgtcggcgg ggttgacaag gtcgttgcgt    600
cagtccaaca tttgttgcca tattttcctg ctctccccac cagctgctct tttcttttct    660
ctttcttttc ccatcttcag tatattcatc ttcccatcca agaaccttta tttcccctaa    720
gtaagtactt tgctacatcc atactccatc cttcccatcc cttattcctt tgaacctttc    780
agttcgagct ttcccacttc atcgcagctt gactaacagc taccccgctt gagccaccgt    840
caaaatggga gacc                                                       854

<210> SEQ ID NO 44
<211> LENGTH: 854
<212> TYPE: DNA
<213> ORGANISM: Artificial Sequence
<220> FEATURE:
<223> OTHER INFORMATION: A. nidulans gpdA promoter fused FRT
      recombination site

<400> SEQUENCE: 44
ggtctcggtg cgaagttcct attctctaga aagtatagga acttccagac agctctggcg     60
gctctgaggt gcagtggatg attattaatc cgggaccggc cgcccctccg ccccgaagtg    120
gaaaggctgg tgtgcccctc gttgaccaag aatctattgc atcatcggag aatatggagc    180
ttcatcgaat caccggcagt aagcgaagga gaatgtgaag ccaggggtgt atagccgtcg    240
gcgaaatagc atgccattaa cctaggtaca gaagtccaat tgcttccgat ctggtaaaag    300
attcacgaga tagtaccttc tccgaagtag gtagagcgag tacccggcgc gtaagctccc    360
taattggccc atccggcatc tgtagggcgt ccaaatatcg tgcctctcct gctttgcccg    420
gtgtatgaaa ccggaaaggc cgctcaggag ctggccagcg gcgcagaccg ggaacacaag    480
ctggcagtcg acccatccgg tgctctgcac tcgacctgct gaggtccctc agtccctggt    540
aggcagcttt gccccgtctg tccgcccggt gtgtcggcgg ggttgacaag gtcgttgcgt    600
cagtccaaca tttgttgcca tattttcctg ctctccccac cagctgctct tttcttttct    660
ctttcttttc ccatcttcag tatattcatc ttcccatcca agaaccttta tttcccctaa    720
gtaagtactt tgctacatcc atactccatc cttcccatcc cttattcctt tgaacctttc    780
agttcgagct ttcccacttc atcgcagctt gactaacagc taccccgctt gagccaccgt    840
caaaatggga gacc                                                       854

<210> SEQ ID NO 45
<211> LENGTH: 848
<212> TYPE: DNA
<213> ORGANISM: Aspergillus nidulans

<400> SEQUENCE: 45
ggtctcggtg ctactaatca tgactctgcg ggaacagacc gtgatttttg gaacacctca 60
ggcttcaagt tacaaggtat tgtttgtagg cagtacctac tgaaattgct tgttaccgta 120
tactacctgc acatagtact agatgacttt aatgtaggta ggagagttaa gcagtttcct 180
ggaagtggcg ttgatcatta ttccccgaaa atgtagtacc cagtaagtgg tctagcggtg 240
gctatggtag gacatctatg cctaagctgg agttctcatt gaacgtgtac cggccgattg 300
ccctaaactc tgattgagag ccggaaacct catctacctg atgctcaggg gccatccaat 360
agcttccgat agcattacag acagatggac tcgtcttggc ccacgggtct agaacagtcg 420
ccggaactgc ctctatttga aacggagctg aaccatgata cttaagcgtg ccaagcggcg 480
ccgtttccca ctggaacaag gagcaataga attctgcaga gattcttcat tcaggctatt 540
cagcaattcg gtttgtggag cggatcgggg tccactgggt ttagtctggg gtttttcttt 600
gcccgcatgg gctctagcac atgcacagct tgcagttgct gctacgctat ctgggaaaac 660
gaatggctat tcaggagttt ataaccaaaa gagccggaaa caggctgatt gccctctcac 720
ggggacacgt tgtacttctg atccagaggc tattaaccgg acactaccta taaaggaggt 780
agcattcctt tctgtccggc tcccagattc caacaaccca actgacagga tcagcacaat 840
gggagacc 848

<210> SEQ ID NO 46
<211> LENGTH: 538
<212> TYPE: DNA
<213> ORGANISM: Artificial Sequence
<220> FEATURE:
<223> OTHER INFORMATION: Tet-promoter fungal

<400> SEQUENCE: 46
ggtctcggtg cgcgtatcac gaggcccttt cgtcctcgag tttaccactc cctatcagtg 60
atagagaaaa gtgaaagtcg agtttaccac tccctatcag tgatagagaa aagtgaaagt 120
cgagtttacc actccctatc agtgatagag aaaagtgaaa gtcgagttta ccactcccta 180
tcagtgatag agaaaagtga aagtcgagtt taccactccc tatcagtgat agagaaaagt 240
gaaagtcgag tttaccactc cctatcagtg atagagaaaa gtgaaagtcg agtttaccac 300
tccctatcag tgatagagaa aagtgaaagt cgaggtcggt tcccgggtcg agcccatctt 360
cagtatattc atcttcccat ccaagaacct ttatttcccc taagtaagta ctttgctaca 420
tccatactcc atccttccca tcccttattc ctttgaacct ttcagttcga gctttcccac 480
ttcatcgcag cttgactaac agctaccccg cttgagcaga catcaccaat gggagacc 538

<210> SEQ ID NO 47
<211> LENGTH: 822
<212> TYPE: DNA
<213> ORGANISM: Aspergillus niger

<400> SEQUENCE: 47
ggtctcggtg caaccggggg gagtacattg agtggccgca gtggaaggaa tcgcggcagt 60
tgatgaattt cggagcgaac gacgccagtc tccttacgga tgatttccgc aacgggacat 120
atgagttcat cctgcagaat accgcggcgt tccacatctg atgccattgg cggaggggtc 180

-continued

```
cggacggtca ggaacttagc cttatgagat gaatgatgga cgtgtctggc ctcggaaaag    240
gatatatggg gatcatgata gtactagcca tattaatgaa gggcatatac cacgcgttgg    300
acctgcgtta tagcttcccg ttagttatag taccatcgtt ataccagcca atcaagtcac    360
cacgcacgac cggggacggc gaatccccgg gaattgaaag aaattgcatc ccaggccagt    420
gaggccagcg attggccacc tctccaaggc acagggccat tctgcagcgc tggtggattc    480
atcgcaattt cccccggccc ggcccgacac cgctataggc tggttctccc acaccatcgg    540
agattcgtcg cctaatgtct cgtccgttca caagctgaag agcttgaagt ggcgagatgt    600
ctctgcagga attcaagcta gatgctaagc gatattgcat ggcaatatgt gttgatgcat    660
gtgcttcttc cttcagcttc ccctcgtgca gatgaggttt ggctataaat tgaagtggtt    720
ggtcggggtt ccgtgagggg ctgaagtgct tcctcccttt tagacgcaac tgagagcctg    780
agcttcatcc ccagcatcat tacaccgtca aaatgggaga cc                       822
```

```
<210> SEQ ID NO 48
<211> LENGTH: 1518
<212> TYPE: DNA
<213> ORGANISM: Aspergillus niger

<400> SEQUENCE: 48

ggtctcggtg cagtcggaag ctggaggcgg acatcaacaa cggcgggtgg gagtcgatct     60
agacattggt ccctgggagt tattgtgttc cgtgtttcag cattgttgtg tatcctgatt    120
tggcttgatg acccgtgcca aaagctcatg atgactttgc atgcatttta tcgaactgtt    180
tgttcttgaa aataatttac atatatgtat ctacgatgca gagggccctt gttcttgttg    240
atggcggttg atactatata gtactctatg cgttgtgctt ggcgagattc actgatgctg    300
tcggtaatgg ttgtttgaca gtgtgaatct tgatctgaat cgtgatttat cctatcctgc    360
acactgaact aggtattgat ctacatgtag acctcgattc gaaaccagat cagccgtgtg    420
actcacatgg agcgggtgtc tcgcaaggat aactttagcc ctggtactag cccccatacg    480
cactgtcatt agtgaggtgc tgagacaatt taagctttcg cttcagccat agcttataaa    540
cagtaagatt atgagagggg gaaaagcttc aaccaagact attttcaccc gtctttaggt    600
tgttcataat gggctacggc ttcatggctc tcatgcctcc atcgtataat cgtcccttgt    660
agacagtagc cagctactta ctagttagca cagtggacac aagccagcga atcggggtga    720
agccaattag cattggatat ccacgaagta tgatcgtcac cctccatgac ttcacacggt    780
tgctgcatcg gttcaccggg ttgaacctag ccgggcagga tcggagcaag tcgctggatc    840
cctcacggat cacagagctc cagctccacg aagaaaagca ggatgcgatc cccgcacatc    900
ggagaattgc ataccgttga agcaatccaa gcaattggca ggtgtcatct ccattacgta    960
ccgtgacctt catacctcc gtatttatac ctgcccctcc ctcccccgct tctcctgctt    1020
tcttcctctc tctttctctc ttccatcaac tcaacttcca tctacttcac tacttcctgt   1080
caagacttcc atcgactttc atcacaagtc atcctctccc atgtttgtat tccctgtata   1140
gaccgtactg acctcttccc tagaaaccct cgtgcaatgt aattccacct gcgtcggccc   1200
ctccccgggg tcttgtctca atacttcatt acacacgatg gaagtcatgc aatgcctttg   1260
gctggactct ctcaatgatc aggtatctca ggtaaatctt gggcgtggac cggtgttcgt   1320
tcctatccgt tggttgtgca gcattgctag cattgctgcc tgccatcggc tctgggttcg   1380
ttctgagatt atacggttaa acttgatctg gataatacca gcgaaaggat catgccttcc   1440
```

-continued ctcgtttccc cccacttgat ggaatggcta acaattccca gtcccaccta ccacacccca 1500
ccgtcaaaat gggagacc 1518

<210> SEQ ID NO 49
<211> LENGTH: 1021
<212> TYPE: DNA
<213> ORGANISM: Aspergillus niger

<400> SEQUENCE: 49
ggtctcggtg catttaagta actgagtttt gtgagttgtc ttgaaacaat ttctacacag 60
gaggccgatg caaatttaca atttcggtct tgcaattgtc gttgtgcacg agtaagtcaa 120
gtacacagta ggaggctgag aggcaagcgt tttgccatcg gatatccggg accagatgga 180
aagaaggggc ggttccccat ggatggagcg cgaaggtgtg gactccaaga aaacgctttg 240
gttcggtcaa gacggggaaa tgggagagga atggatatct tacgaagccg aattacggag 300
aaagggccca aacatgtaaa ttatggcctg taggtcaatc agcaaagggc cgagcggtga 360
ttgcgagtac accgatcggt agactacgga agggatgaaa aagacaggaa aatagcgaga 420
gctacatgcc gtttcagagg ctatcgaaat gatattccaa agtatcacca gtagccataa 480
ccactataat aaaggacgaa gatgagagtg ccttcgttct ctttgaccag aaattcactc 540
atagtatcaa agggtatttc ccaataatgt cagcggtcgg agttggttac tggcgcgatc 600
gggagatatc ggctcttcgt tgcctgggcc agcattagcg ccgggtccag gttttttttt 660
tgcaaatttt tttttctttt cctggctatg tttttttttcg ttccccctaa caatgggaag 720
gacctcccta ctccgtaccg ggccaaccaa tccggccaat ggaaactggg ccgggacgcc 780
catcgccgcc gctgccactg caaattcagg ccagcgaaaa acccaagagc gtcctagcct 840
ctccgctcgc ttcttcccgc ttacaagagc ccttcgctcg ctattttttc ttccctccct 900
tcccttctct cttcttttct ttccatcccc tttgaagtgt cctgtttgac tggcactatc 960
atccatctcc tctctttctt tccttagttt tcgttcatca ccaccgtcaa aatgggagac 1020
c 1021

<210> SEQ ID NO 50
<211> LENGTH: 779
<212> TYPE: DNA
<213> ORGANISM: Penicillium chrysogenum

<400> SEQUENCE: 50
ggtctcggtg cgtcgactac atgtatctgc atgttgcatc gggaaatccc accacaggga 60
cagccaagcg gccccgcgac ttggcagtgg gcaaactacg cccgattctg gtgccaagaa 120
ccgagaagaa tgagacagac ccacgttgca ctctaaccgg atgctatcga cttacggtgg 180
ctgaagattc aacacgctgc aacgagagcc aaggtggtcc ggacattttc tacgtgccgg 240
tttaccttgg aacatcgccg tcgttgagtg cacgttgcct actctctcgt ggcttggctg 300
ggcccacgag cccgattgac tcgacggtgt tacttgggta tctatggccc cgttttctgg 360
cacggtaatg ataagtactt actagtcatc gagcggggga gtgttgctct gcccgagcat 420
caacgattgg cctgatcgca ccgtctgcaa atgccacggt gcggaccgac tgaaatctca 480
gaccaccaaa gaccctccga cttcgagata cggttactaa ttttacactg gctccagcgg 540
ccccatccag taagcatctg ggctgcaagc gtataatgtc tccaggttgt ctcagcataa 600
acaccccgcc cccgctcagg cacacaggaa gagagctcag gtcgtttcca ttgcgtccat 660
actcttcact cattgtcatc tgcaggagaa cttcccctgt ccctttgcca agccctctct 720
tcgtcgttgt ccacgccttc aagttttcac cattattttc accgtcaaaa tgggagacc 779

<210> SEQ ID NO 51
<211> LENGTH: 1021
<212> TYPE: DNA
<213> ORGANISM: Aspergillus niger

<400> SEQUENCE: 51
ggtctcggtg cttttccctc acatgttttg ccgcaccagc catcccacta tcaaaaagcg 60
atgatgtttg agattgtcgg gtgtccacat cttttagtgt gaatcgctag tagaatttgg 120
gatattattg agcatcatcc catgatagcg agtacaagcc ccgagtaaat accaacattg 180
ctatgctgct gtgctgctat ctagtttgct acgttggtcg ttgacctcac agggatttcc 240
accaaaaagt ggaccgggcg ggcgccactc ggccgtgcca cagcagcctg agagcggaca 300
aataacaaca gccgcctgcc gcggggttcg gttgcaaaca tgaccaacag gccaggccat 360
catcaaccca ccgctgcgtt gatgcccagg atttcagtcc aataatccac aatttaccaa 420
cggatagagc taggtgaatt agatagacag gagggccaga gggaggggac cgagatgaaa 480
aattttcgat gaaagagtgg tcaaggtggg gtcgtagttc ggcgctccga gggcgaggaa 540
ccaaggaaag gcgaggaaag gacaggctga tcgcgctgcg ttgctgggct gcaagcgtgt 600
ccagttgagt ctggaaaagg ctccgccgtg aagattctgc gttggtcccg cacctgcgcg 660
gtgggggcat taccccctcca tgtccaatga tttcaagtca aagccaaggg ttgaagcccg 720
cccgcttagt cgccttctcg cttgacccct ccatataagt atttcccctc ctccccctcc 780
cacaaatttt tcctttccct ttcctccctc gtccgcttca gtacgtatat cttccccccc 840
tctctcttcc ttctcactct tctctccttc tttcttgatt catcctctct ctaactgact 900
tctttgctca gcacctctac gcgttctggc cgtagtatct gagcaatttt tctacagact 960
ttttctatct aattccaaaa aagaacttcg agttcattca ccaccgtcaa aatgggagac 1020
c 1021

<210> SEQ ID NO 52
<211> LENGTH: 880
<212> TYPE: DNA
<213> ORGANISM: Penicillium chrysogenum

<400> SEQUENCE: 52
ggtctcgaat gtctccaacc gggaaccgcg ccgactgggc cgacgacgaa gatttcgatg 60
acccctccgt gctcccgccg caagaagtga tcacgaacaa ggacggcacc aagaccgtca 120
tttcctaccg ctacaatgat gacaacaaga aagtgaaggt cacccgccga attaagacca 180
ccgttgtccg cgaacatgtc aacccccaag tcgccgaacg ccgcaaatgg gagaagttcg 240
gcctcgagaa gggccacgcc gccggtccct cgttcgacac cacctccgtc ggcgagaaca 300
tcatcttccg ccccagcgtc aactggaagg ctaatgctaa ggaggccgag aaggagggtg 360
gcgaaaaggg cagcatgaag gaccagttga aggacaagaa ggtcaagtgt cgtatttgca 420
gtggagagca tttcacggct cgctgtccct tcaaggacac catggctccc gtcgaggagg 480
gcactgctgc tgctcctggt gtcgaggcag aggaggatgc aggtggtctt ggtgctggaa 540
agtccagcta cgttcctcct cacatgcgga agggcggtgc tggtggcggc gagaagatgg 600
gcggtcgttt cgagaaggac gatttggcga ctctcagagt tacaaacgtc agcgagttgg 660
cagaggagaa cgagttgcgg gatctcttcg agcgtttcgg tcgtgtcacc agagtcttcc 720

-continued

```
ttgcacggga tcgggaaacc cagagagcca agggctttgc tttcatcagc tatgcggacc    780

gtggcgacgc agcacttgct tgcgagaagg tggatggctt cggttaccgc caccttattc    840

tccgcgtcga gttcgccaag cgcactactt aaaggagacc                          880


<210> SEQ ID NO 53
<211> LENGTH: 883
<212> TYPE: DNA
<213> ORGANISM: Aspergillus niger

<400> SEQUENCE: 53

ggtctcgaat gtcgaagctt ggaaaccgcg ccgactgggc cgacgacgag gagttcgacg     60

acccctccgc tctccccccg cagcaaatca cgaccaacaa agatggcacg aagacgatcg    120

tttcctaccg attcaacgac gaaggcaaga aggtgaaggt gacccgccgg atcaaaaacga   180

ccgttgtgcg cgaacatgtc aacccgcagg tcgcggagcg gaggtcctgg gccaagttcg    240

gtctggagaa gggcaacgcg cccggacctt cgttcgatac gacctccgtg ggtgagaaca    300

ttgttttccg gcccagcgtc aactggaagc ttcaggcggc tgaggcggag aagaacggtg    360

gcgagaaggg cagtgtgaag gatcagctga aggacaagaa ggtcaagtgt cgtatttgca    420

gtggcgagca ctttactgct cgctgtccct tcaaggatac tatggctcct gtcgacgagc    480

ccactgctgg tggagaggct ggtgatgagg attctccggc tgctggcgct ttgggtgctg    540

gtacttctag ctacgtgccc cctcatctgc ggaagggtgc tgctggtggc ggagagagaa    600

tggctggcaa gtatgagaag gatgatttgg cgactctgag agttacgaac gtgagcgagt    660

tggcagagga aggagaactg cgggatctgt tcgaacgctt cggtcgtgtc accagagtct    720

tccttgccag agacagagaa acccagagag ccaagggctt cgctttcatc agctttgcgg    780

atcggagcga tgctgcacgt gcttgcgaga agatggatgg cttcggttac cgtcacctta    840

tcctgcgcgt cgaattcgcc aagcgtgcca cttaaaggag acc                      883


<210> SEQ ID NO 54
<211> LENGTH: 763
<212> TYPE: DNA
<213> ORGANISM: Artificial Sequence
<220> FEATURE:
<223> OTHER INFORMATION: Tet-on gene fungal

<400> SEQUENCE: 54

ggtctcgaat gagccgtctg gacaagtcca aggtcatcaa cggcgctctc gagctgctca     60

acggtgtcgg tatcgagggt ctgaccaccc gcaagctggc ccagaagctc ggtgttgagc    120

agcccaccct ctactggcac gtcaagaaca agcgtgctct cctggatgct ctgcccattg    180

agatgcttga ccgtcaccac acccacttct gccccttgga aggcgagagc tggcaggact    240

tcctccgcaa caacgccaag tctttccgct gcgctctcct ctcccaccgt gacggtgcca    300

aggtccacct gggcactcgt cccaccgaga agcagtacga gactctggag aaccagctgg    360

ctttcctttg ccagcagggt ttctccctcg agaacgccct ctacgctctt tctgctgtcg    420

gccacttcac cctgggctgc gttctcgagg agcaggagca ccaggttgcc aaggaggagc    480

gtgagactcc caccaccgac tccatgcccc ctctcctccg ccaggccatt gagctgttcg    540

accgccaggg tgctgagccc gccttcctgt tcggtctgga gctgatcatc tgcggtcttg    600

agaagcaatt gaagtgcgaa tccggtggtc ctgctgatgc ccttgacgac ttcgacctcg    660

acatgttgcc tgccgatgcc ttggatgact tcgatcttga catgcttccc gccgatgctc    720

tcgatgactt tgacctcgat atgcttcctg gctaaaggag acc                      763
```

<210> SEQ ID NO 55
<211> LENGTH: 763
<212> TYPE: DNA
<213> ORGANISM: Artificial Sequence
<220> FEATURE:
<223> OTHER INFORMATION: Tet-off gene fungal

<400> SEQUENCE: 55
ggtctcgaat gagccgtctg gacaagtcca aggtcatcaa ctccgctctc gagctgctca 60
acgaggtcgg tatcgagggt ctgaccaccc gcaagctggc ccagaagctc ggtgttgagc 120
agcccaccct ctactggcac gtcaagaaca agcgtgctct cctggatgct ctggccattg 180
agatgcttga ccgtcaccac acccacttct gccccttgga aggcgagagc tggcaggact 240
tcctccgcaa caacgccaag tctttccgct gcgctctcct ctcccaccgt gacggtgcca 300
aggtccacct gggcactcgt cccaccgaga agcagtacga gactctggag aaccagctgg 360
ctttcctttg ccagcagggt ttctccctcg agaacgccct ctacgctctt tctgctgtcg 420
gccacttcac cctgggctgc gttctcgagg accaggagca ccaggttgcc aaggaggagc 480
gtgagactcc caccaccgac tccatgcccc ctctcctccg ccaggccatt gagctgttcg 540
accaccaggg tgctgagccc gccttcctgt tcggtctgga gctgatcatc tgcggtcttg 600
agaagcaatt gaagtgcgaa tccggtggtc ctgctgatgc ccttgacgac ttcgacctcg 660
acatgttgcc tgccgatgcc ttggatgact tcgatcttga catgcttccc gccgatgctc 720
tcgatgactt tgacctcgat atgcttcctg gctaaaggag acc 763

<210> SEQ ID NO 56
<211> LENGTH: 1288
<212> TYPE: DNA
<213> ORGANISM: Saccharomyces cerevisiae

<400> SEQUENCE: 56
ggtctcgaat gcctcagttc ggtatcctct gcaagactcc tcccaaggtc ctcgtccgcc 60
agttcgttga gcgcttcgag cgtcccagcg gcgagaagat tgctctctgc gctgctgagc 120
tgacctacct ctgctggatg atcacccaca acggtactgc catcaagcgt gccactttca 180
tgtcctacaa caccattatc tccaactcgc tgtctttcga cattgtcaac aagtctcttc 240
agttcaagta caagacccag aaggccacca ttcttgaggc ctccctcaag aagttgattc 300
ctgcctggga gttcaccatc atcccctact acggccagaa gcaccagtcg gatatcaccg 360
atatagtatc ttctctccag ctccagttcg agagcagcga agaagcggac aagggtaact 420
cccactccaa gaagatgctc aaggccctcc tcagcgaagg cgagagcatc tgggagatca 480
ctgagaagat cctcaactcg ttcgagtaca cctcccgctt caccaagacc aagactctct 540
accagttcct gttcctggcc accttcatca actgcggtcg tttctccgat atcaagaacg 600
ttgaccccaa gtcgttcaag ctcgtccaga acaagtacct tggtgtcatc atccagtgct 660
tggtgaccga gactaagacc tccgtcagcc gtcacatcta cttcttctct gctcgtggtc 720
gtatcgaccc tctggtctac ctggatgagt tcctccgcaa ctccgagcct gttctgaagc 780
gtgtcaaccg tactggcaac tcctcctcca acaagcagga gtaccagctt ctgaaggaca 840
acctggtccg cagctacaac aaggctctga agaagaacgc cccctactcc atcttcgcca 900
ttaagaacgg tcccaagtcc cacatcggtc gtcacctgat gacttctttc ctgagcatga 960
agggattgac cgaattgacc aacgttgttg gaaactggtc cgacaagcgc gcttctgctg 1020
ttgctcgcac cacctacacc caccagatca ccgccatccc cgaccactac ttcgctcttg 1080
tctcccgcta ctacgcctac gaccccatct ccaaggagat gattgccctc aaggatgaaa 1140
ccaaccccat tgaggaatgg cagcacattg agcagctcaa gggctctgct gagggcagca 1200
tccgttaccc cgcctggaac ggtatcatct cccaggaggt ccttgactac ctttcttcct 1260
acatcaaccg caggatctaa aggagacc 1288

<210> SEQ ID NO 57
<211> LENGTH: 733
<212> TYPE: DNA
<213> ORGANISM: Artificial Sequence
<220> FEATURE:
<223> OTHER INFORMATION: Venus GFP

<400> SEQUENCE: 57
ggtctcgaat gagcaagggt gaagaactct tcactggtgt tgttcccatt cttgttgagc 60
ttgacggtga tgtcaacggc cacaagttct ccgtcagcgg tgagggcgag ggtgatgcca 120
cctacggcaa gttgactctc aagctgatct gcaccactgg caagcttcct gttccttggc 180
ccaccctcgt caccaccctc ggatacggtc tgcagtgctt cgctcgttac cccgaccaca 240
tgaagcagca cgacttcttc aagtccgcca tgcccgaggg ctacgtgcag gagcgcacca 300
tcttcttcaa ggatgacggc aactacaaga cccgtgccga ggtcaagttc gagggtgaca 360
ccctcgtcaa ccgcattgag ctgaagggta tcgacttcaa ggaagatggc aacatccttg 420
gccacaagct ggaatacaac tacaactctc acaacgtcta catcaccgcc gacaagcaga 480
agaacggcat caaggccaac ttcaagatcc gccacaacat tgaggatggt ggtgtgcagc 540
tggcggacca ctaccagcag aacaccccca tcggtgatgg acctgtgttg ctccccgaca 600
accactacct gtcctaccag tctgctctct ccaaggaccc caacgagaag cgtgaccaca 660
tggtcctcct cgagttcgtc actgctgctg gtatcaccca cggaatggat gagctgtaca 720
aataaaggag acc 733

<210> SEQ ID NO 58
<211> LENGTH: 391
<212> TYPE: DNA
<213> ORGANISM: Streptoalloteichus hindustanus

<400> SEQUENCE: 58
ggtctcgaat ggccaagttg accagtgccg ttccggtgct caccgcgcgc gacgtcgccg 60
gagcggtcga gttctggacc gaccggctcg ggttctcccg ggacttcgtg gaggacgact 120
tcgccggtgt ggtccgggac gacgtgaccc tgttcatcag cgcggtccag gaccaggtgg 180
tgccggacaa caccctggcc tgggtgtggg tgcgcggcct ggacgagctg tacgccgagt 240
ggtcggaggt cgtgtccacg aacttccggg acgcctccgg gccggccatg accgagatcg 300
gcgagcagcc gtgggggcgg gagttcgccc tgcgcgaccc ggccggcaac tgcgtgcact 360
tcgtggccga ggagcaggac taaaggagac c 391

<210> SEQ ID NO 59
<211> LENGTH: 1513
<212> TYPE: DNA
<213> ORGANISM: Aspergillus niger

<400> SEQUENCE: 59
ggtctcgaat ggttgcctgg tggtccctct tcctgtacgg actccaggtt gctgctcctg 60
ctcttgctgc cactcctgcc gactggcgct cccagtccat ctacttcctg ctgaccgacc 120
gcttcgctcg taccgatgga agcaccactg ccacctgcaa cactgcggac cagaagtact 180

-continued

```
gcggtggaac ctggcagggt atcattgaca agctcgacta catccagggc atgggtttca    240
ctgccatctg gatcaccccc gtgactgctc agctccccca gaccactgcc tacggtgatg    300
cctaccacgg atactggcag caggatatct actctctgaa cgagaactac ggcactgccg    360
atgacctcaa ggccctttct tctgctctgc acgagcgtgg aatgtacctg atggtggatg    420
ttgttgccaa ccacatgggc tacgacggtg ctggcagctc tgttgactac tctgtcttca    480
agcccttctc ttcccaggac tacttccacc ccttctgctt catccagaac tacgaagacc    540
agacccaggt tgaggactgc tggttgggtg acaacaccgt gtccctcccc gatcttgaca    600
ccaccaagga tgttgtcaag aacgaatggt acgactgggt gggatccctg gtgtccaact    660
actccatcga tggactccgc attgacaccg tcaagcacgt ccagaaggac ttctggcctg    720
gctacaacaa ggctgctggt gtctactgca ttggtgaggt cctcgatgga gatcctgcct    780
acacctgccc ctaccagaac gtcatggatg gtgttctcaa ctacccccatc tactacccct    840
tgctcaacgc cttcaagtcc acctccggca gcatggatga cctctacaac atgatcaaca    900
ccgtcaagtc cgactgcccc gacagcactc tccttggaac cttcgtcgag aaccacgaca    960
accctcgttt cgccagctac accaacgaca ttgctcttgc caagaacgtc gctgctttca   1020
tcatcctgaa cgacggtatc cccatcatct acgctggcca ggagcagcac tacgctggtg   1080
gcaacgaccc tgccaaccgt gaggccacct ggctgtctgg ctaccccacc gacagcgaat   1140
tgtacaagtt gattgcctct gccaacgcca tccgcaacta cgccatctcc aaggacactg   1200
gtttcgtcac ctacaagaac tggcccatct acaaggatga caccaccatt gccatgcgca   1260
agggtactga tggcagccag atcgtcacca tcctgtccaa caagggtgcc tccggtgact   1320
cctacaccct ctccctctcc ggtgctggct acactgctgg ccagcagctg accgaggtca   1380
ttggctgcac caccgtcacc gttggatcgg atggcaacgt gcctgtgccc atggccggtg   1440
gtcttcctcg tgtcctctac cccactgaga agcttgctgg cagcaagatc tgctcgtcgt   1500
cgtaaaggag acc                                                      1513
```

<210> SEQ ID NO 60
<211> LENGTH: 1036
<212> TYPE: DNA
<213> ORGANISM: Artificial Sequence
<220> FEATURE:
<223> OTHER INFORMATION: HygB gene

<400> SEQUENCE: 60

```
ggtctcgaat gcctgaactc accgcgacgt ctgtcgagaa gtttctgatc gaaaagttcg     60
acagcgtctc cgacctgatg cagctctcgg agggcgaaga atctcgtgct ttcagcttcg    120
atgtaggagg gcgtggatat gtcctgcggg taaatagctg cgccgatggt ttctacaaag    180
atcgttatgt ttatcggcac tttgcatcgg ccgcgctccc gattccggaa gtgcttgaca    240
ttggggaatt cagcgagagc ctgacctatt gcatctcccg ccgtgcacag ggtgtcacgt    300
tgcaagacct gcctgaaacc gaactgcccg ctgttctgca gccggtcgcg gaggccatgg    360
atgcgatcgc tgcggccgat cttagccaga cgagcgggtt cggcccattc ggaccgcaag    420
gaatcggtca atacactaca tggcgtgatt tcatatgcgc gattgctgat ccccatgtgt    480
atcactggca aactgtgatg gacgacaccg tcagtgcgtc cgtcgcgcag gctctcgatg    540
agctgatgct ttgggccgag gactgccccg aagtccggca cctcgtgcac gcggatttcg    600
gctccaacaa tgtcctgacg gacaatggcc gcataacagc ggtcattgac tggagcgagg    660
```

```
cgatgttcgg ggattcccaa tacgaggtcg ccaacatctt cttctggagg ccgtggttgg    720

cttgtatgga gcagcagacg cgctacttcg agcggaggca tccggagctt gcaggatcgc    780

cgcggctccg ggcgtatatg ctccgcattg gtcttgacca actctatcag agcttggttg    840

acggcaattt cgatgatgca gcttgggcgc agggtcgatg cgacgcaatc gtccgatccg    900

gagccgggac tgtcgggcgt acacaaatcg cccgcagaag cgcggccgtc tggaccgatg    960

gctgtgtaga agtactcgcc gatagtggaa accgacgccc cagcactcgt ccgagggcaa   1020

aggaataaag gagacc                                                   1036


<210> SEQ ID NO 61
<211> LENGTH: 730
<212> TYPE: DNA
<213> ORGANISM: Artificial Sequence
<220> FEATURE:
<223> OTHER INFORMATION: DsRed-SKL

<400> SEQUENCE: 61

ggtctcgaat ggcctccagc gaagatgtca tcaaggagtt catgcgcttc aaggtccgca     60

tggaaggatc cgtcaacggc cacgagttcg agattgaggg tgagggtgag ggccgcccct    120

acgaaggcac ccagactgcc aagctcaagg tcaccaaggg tggtcctctc cccttcgctt    180

gggatatcct gtctcctcag ttccagtacg gctccaaggt ctacgtcaag caccccgccg    240

acatccccga ctacaagaag ctttctttcc ccgagggttt caagtgggag cgtgtcatga    300

acttcgagga tggtggtgtt gtgaccgtta ctcaggacag cagcttgcag gatggctctt    360

tcatctacaa ggtcaagttc attggtgtca acttcccctc cgacggccct gtcatgcaga    420

agaagaccat gggctgggaa gcgtcgactg agcgtctgta cccccgtgac ggtgttctca    480

agggtgagat ccacaaggct ctcaagctca aggacggtgg tcactacctt gttgagttca    540

agtccatcta catggccaag aagcctgtgc agctgcccgg atactactac gtggactcca    600

agcttgacat cacctcccac aacgaagact acaccattgt tgagcagtac gagcgtgctg    660

agggccgcca ccacctcttc ctgacccacg gaatggatga gctgtacaag tcgaaactat    720

aaaggagacc                                                           730


<210> SEQ ID NO 62
<211> LENGTH: 372
<212> TYPE: DNA
<213> ORGANISM: Penicillium chrysogenum

<400> SEQUENCE: 62

ggtctcgtaa aacttcttta tcggttctct cttacgactt tttgaatgga acgtttcctt     60

cttctcaggc gggcctatct ttgggccgaa gctcttttcc ttgtactgta ggacctggtt    120

gataatgatt cccaaaaaga catccagcat gtcagttact tgcattcgtc agtctataca    180

aaagcaatgg tttagagaaa ttttgaactt tatacatggt tttatttgtt gcttcacggc    240

cgtaccttct ggaaatccac ggtaggagtg tcaatttgcg tttttgataa tccttccaag    300

gttcttctcg aagtagttgt tctataattg cttcacagct accatggaac atcccaagca    360

ccctcggaga cc                                                       372


<210> SEQ ID NO 63
<211> LENGTH: 322
<212> TYPE: DNA
<213> ORGANISM: Penicillium chrysogenum
```

<400> SEQUENCE: 63

```
ggtctcgtaa aatggaataa acccagtttg tttcctttta attgggatag gtgcacgagg     60

tcggggtttt tgtatggcga tactatctct ctggcgataa cgaaatttaa ggattgtgca    120

tggcatgtcc ggctcgggcc ttgtcatagt gccgggcgct gtgaagcgag agaattgttc    180

tctgaaatga caacaaaaat tgcaaaaatc ccttttggtc caagacattt caattaggcg    240

gatttccaat ctggccttgt atatgtagtg tgtatgtatc cctgtacata caatgtagtc    300

cgatatccac acctcggaga cc                                             322
```

<210> SEQ ID NO 64
<211> LENGTH: 322
<212> TYPE: DNA
<213> ORGANISM: Penicillium chrysogenum

<400> SEQUENCE: 64

```
ggtctcgtaa aaggctcttg atgacgagcc aatgcatctt ttgtatgtag cttcaaccga     60

ctccgtcttc acttcttcgc ccgcactgcc taccgtttgt accatctgac tcatataaat    120

gtctagcccc tacctacact atacctaagg gagagaagcg tagagtgatt aacgtacggg    180

cctatagtac cccgatctct agatagaaca tttagtagag attaggatgc ctaactaatt    240

taacttgagc attgtcccgt tcatattgat tttcagtcca ttatacactc ttaatcgttt    300

cccggtagaa gcctcggaga cc                                             322
```

<210> SEQ ID NO 65
<211> LENGTH: 322
<212> TYPE: DNA
<213> ORGANISM: Aspergillus nidulans

<400> SEQUENCE: 65

```
ggtctcgtaa ataaatggtt tgcgttgcga ttgactgaaa cgaaaaaaag cgaaaatgat     60

tctgggaatg aattgataaa gcgcgggctc tgcggtacgg ttacggttgc ggtcgcggac    120

gaatggactg ggctgagctg ggctggagga agtccatcga acaaggacaa ggggtggaat    180

atggcacggg tcgattttgt tatacatacc ctaccatcca tctatccatt taaataccaa    240

atgagttgtt gaatggattc gcggtcttct cggtttattt ttgcttgctt gcgtgcttaa    300

gggatagtgt gcctcggaga cc                                             322
```

<210> SEQ ID NO 66
<211> LENGTH: 356
<212> TYPE: DNA
<213> ORGANISM: Artificial Sequence
<220> FEATURE:
<223> OTHER INFORMATION: CYC1 terminator fused to lox71 recombination site

<400> SEQUENCE: 66

```
ggtctcgtaa accgacgccg accaacaccg ccggtccgac gcggcccgac gggtccgagg     60

cctcggagat ccgtccccct tttcctttgt cgatatcatg taattagtta tgtcacgctt    120

acattcacgc cctcccccca catccgctct aaccgaaaag gaaggagtta gacaacctga    180

agtctaggtc cctatttatt tttttatagt tatgttagta ttaagaacgt tatttatatt    240

tcaaattttt cttttttttc tgtacagacg cgtgtacgca tgtaacatta tactgaaaac    300

cttgcttgag aataacttcg tataatgtat gctatacgaa cggtacctcg gagacc        356
```

-continued

<210> SEQ ID NO 67
<211> LENGTH: 356
<212> TYPE: DNA
<213> ORGANISM: Artificial Sequence
<220> FEATURE:
<223> OTHER INFORMATION: CYC1 terminator fused to FRT recombination site

<400> SEQUENCE: 67
ggtctcgtaa accgacgccg accaacaccg ccggtccgac gcggcccgac gggtccgagg 60
cctcggagat ccgtccccct tttcctttgt cgatatcatg taattagtta tgtcacgctt 120
acattcacgc cctcccccca catccgctct aaccgaaaag gaaggagtta gacaacctga 180
agtctaggtc cctatttatt tttttatagt tatgttagta ttaagaacgt tatttatatt 240
tcaaattttt cttttttttc tgtacagacg cgtgtacgca tgtaacatta tactgaaaac 300
cttgcttgag agaagttcct attctctaga aagtatagga acttccctcg gagacc 356

<210> SEQ ID NO 68
<211> LENGTH: 322
<212> TYPE: DNA
<213> ORGANISM: Aspergillus nidulans

<400> SEQUENCE: 68
ggtctcgtaa aaatagttca tattccactc tggaaggagg gaaatgaact ggcgcccgca 60
tcaaccctta gctgggttca tgacggtgtg gttgtcgatg ggcttgcaga agatctagca 120
acgctgggtc gacttcgata cccgttaaaa acagtcataa aaatggaaga gttgcaaagc 180
gtatactata tatagctcct atcgctttcg tattgtgact taactattgt agagcctggt 240
agagaagagt agaacacttg accgcattat atctggtatt ctacaaagcc agtgcaccct 300
cggctaacag acctcggaga cc 322

<210> SEQ ID NO 69
<211> LENGTH: 322
<212> TYPE: DNA
<213> ORGANISM: Penicillium chrysogenum

<400> SEQUENCE: 69
ggtctcgtaa agcttcttgc agcactttac tactcgtatt cgctcgtact ttcctggtgt 60
atcaaaaagc aggatggagg cactggtgga ttgcaagcgt tgttggactc gcattatcaa 120
gcggatagcc tgaaaatgga atctcgattt tagtggaata gagtcggtcg ttttcttttt 180
gttactcttt accttactct ttactcgatc tctatccatc catttctgct ttgaaccatt 240
tcacctttac tccatctttt tccctttcct cattcgaatc cgctgtcccg tccacctctc 300
tgattgtttt gcctcggaga cc 322

<210> SEQ ID NO 70
<211> LENGTH: 34
<212> TYPE: DNA
<213> ORGANISM: Artificial Sequence
<220> FEATURE:
<223> OTHER INFORMATION: Lox66 recombination site

<400> SEQUENCE: 70
taccgttcgt ataatgtatg ctatacgaag ttat 34

<210> SEQ ID NO 71
<211> LENGTH: 34
<212> TYPE: DNA
<213> ORGANISM: Artificial Sequence
<220> FEATURE:
<223> OTHER INFORMATION: Lox71 recombination site

<400> SEQUENCE: 71
ataacttcgt ataatgtatg ctatacgaac ggta 34

<210> SEQ ID NO 72
<211> LENGTH: 34
<212> TYPE: DNA
<213> ORGANISM: Artificial Sequence
<220> FEATURE:
<223> OTHER INFORMATION: FRT recombination site

<400> SEQUENCE: 72
gaagttccta ttctctagaa agtataggaa cttc 34

<210> SEQ ID NO 73
<211> LENGTH: 1048
<212> TYPE: DNA
<213> ORGANISM: Artificial Sequence
<220> FEATURE:
<223> OTHER INFORMATION: Cre-recombinase gene

<400> SEQUENCE: 73
ggtctcgaat gtccaattta ctgaccgtac accaaaattt gcctgcatta ccggtcgatg 60
caacgagtga tgaggttcgc aagaacctga tggacatgtt cagggatcgc caggcgtttt 120
ctgagcatac ctggaaaatg cttctgtccg tttgccggtc gtgggcggca tggtgcaagt 180
tgaataaccg gaaatggttt cccgcagaac ctgaagatgt tcgcgattat cttctatatc 240
ttcaggcgcg cggtctggca gtaaaaacta tccagcaaca tttgggccag ctaaacatgc 300
ttcatcgtcg gtccgggctg ccacgaccaa gtgacagcaa tgctgtttca ctggttatgc 360
ggcggatccg aaaagaaaac gttgatgccg gtgaacgtgc aaaacaggct ctagcgttcg 420
aacgcactga tttcgaccag gttcgttcac tcatggaaaa tagcgatcgc tgccaggata 480
tacgtaatct ggcatttctg gggattgctt ataacaccct gttacgtata gccgaaattg 540
ccaggatcag ggttaaagat atctcacgta ctgacggtgg gagaatgtta atccatattg 600
gcagaacgaa aacgctggtt agcaccgcag gtgtagagaa ggcacttagc ctgggggtaa 660
ctaaactggt cgagcgatgg atttccgtgt ctggtgtagc tgatgatccg aataactacc 720
tgttttgccg ggtcagaaaa aatggtgttg ccgcgccatc tgccaccagc cagctatcaa 780
ctcgcgccct ggaagggatt tttgaagcaa ctcatcgatt gatttacggc gctaaggatg 840
actctggtca gagatacctg gcctggtctg gacacagtgc ccgtgtcgga gccgcgcgag 900
atatggcccg cgctggagtt tcaataccgg agatcatgca agctggtggc tggaccaatg 960
taaatattgt catgaactat atccgtaacc tggatagtga aacaggggca atggtgcgcc 1020
tgctggaaga tggcgattaa aggagacc 1048

<210> SEQ ID NO 74
<211> LENGTH: 1045
<212> TYPE: DNA
<213> ORGANISM: Saccharomyces cerevisiae

<400> SEQUENCE: 74
ggtctcgaat gggtaaaaag cctgaactca ccgcgacgtc tgtcgagaag tttctgatcg 60
aaaagttcga cagcgtctcc gacctgatgc agctctcgga gggcgaagaa tctcgtgctt 120
tcagcttcga tgtaggaggg cgtggatatg tcctgcgggt aaatagctgc gccgatggtt 180

-continued

```
tctacaaaga tcgttatgtt tatcggcact ttgcatcggc cgcgctcccg attccggaag    240

tgcttgacat tggggaattc agcgagagcc tgacctattg catctcccgc cgtgcacagg    300

gtgtcacgtt gcaagacctg cctgaaaccg aactgcccgc tgttctgcag ccggtcgcgg    360

aggccatgga tgcgatcgct gcggccgatc ttagccagac gagcgggttc ggcccattcg    420

gaccgcaagg aatcggtcaa tacactacat ggcgtgattt catatgcgcg attgctgatc    480

cccatgtgta tcactggcaa actgtgatgg acgacaccgt cagtgcgtcc gtcgcgcagg    540

ctctcgatga gctgatgctt tgggccgagg actgccccga agtccggcac ctcgtgcacg    600

cggatttcgg ctccaacaat gtcctgacgg acaatggccg cataacagcg gtcattgact    660

ggagcgaggc gatgttcggg gattcccaat acgaggtcgc caacatcttc ttctggaggc    720

cgtggttggc ttgtatggag cagcagacgc gctacttcga gcggaggcat ccggagcttg    780

caggatcgcc gcggctccgg gcgtatatgc tccgcattgg tcttgaccaa ctctatcaga    840

gcttggttga cggcaatttc gatgatgcag cttgggcgca gggtcgatgc gacgcaatcg    900

tccgatccgg agccgggact gtcgggcgta cacaaatcgc ccgcagaagc gcggccgtct    960

ggaccgatgg ctgtgtagaa gtactcgccg atagtggaaa ccgacgcccc agcactcgtc   1020

cgagggcaaa ggaataaagg agacc                                         1045


<210> SEQ ID NO 75
<211> LENGTH: 770
<212> TYPE: DNA
<213> ORGANISM: Saccharomyces pombe

<400> SEQUENCE: 75

ggtctcggtg cctacaacaa ctaagaaaat ggctatcatg cggaagctgg tgagaagaac     60

agcatcggga caagggaagg aagaacaaag acaaagaaaa caaaagaaag caattgaaaa    120

caaaacaaaa caattttcat tccttctctt atcattcctt ttcttttctt ttctctcatt    180

caacgcactc catcgtatcc gcattcctct tattttttct ctttctctat atccatttct    240

ttctctctag gtgtgtcctc tctctctctt caatttctct actccgcatt ccaacgcatc    300

cttcccccaa cctcccattt cctccttacg gcccgatagc gatcgtcttt ccctcgctat    360

cactcgctac cggcccctcc tctgcaccgt aacctcctac gtatttacca tatcataaag    420

tttttccgga cgcttatcgc tgaccccctg tcgccctcct attggcttcc ggattatctt    480

cttgtccata aggtgatcca tgcttcctga agattcccga aatgtgtcca ctttggcggg    540

gaatcattcc atccacttct ttctctctcg ctttcctcat tcggcgctcc ccttccgcgt    600

cacattggtc ttccgctccg tttttgcttt gccgatgtta cttggggaga ggtgcgataa    660

tcctttcgca aaaactcggt ttgacgcctc ccatggtata aatagtgggt ggtggacagg    720

tgccttcgct tttctttaag caagagaatt gcaattcata atgggagacc               770


<210> SEQ ID NO 76
<211> LENGTH: 3538
<212> TYPE: DNA
<213> ORGANISM: Artificial Sequence
<220> FEATURE:
<223> OTHER INFORMATION: TetR::SSN6 gene

<400> SEQUENCE: 76

ggtctcgaat gtctagatta gataaaagta aagtgattaa cagcgcatta gagctgctta     60

atgaggtcgg aatcgaaggt ttaacaaccc gtaaactcgc ccagaagcta ggtgtagagc    120

agcctacatt gtattggcat gtaaaaaata agcgggcttt gctcgacgcc ttagccattg    180
```

-continued

```
agatgttaga taggcaccat actcactttt gccctttaga aggggaaagc tggcaagatt    240
ttttacgtaa taacgctaaa agttttagat gtgctttact aagtcatcgc gatggagcaa    300
aagtacattt aggtacacgg cctacagaaa aacagtatga aactctcgaa aatcaattag    360
cctttttatg ccaacaaggt ttttcactag agaatgcatt atatgcactc agcgctgtgg    420
ggcattttac tttaggttgc gtattggaag atcaagagca tcaagtcgct aaagaagaaa    480
gggaaacacc tactactgat agtatgccgc cattattacg acaagctatc gaattatttg    540
atcaccaagg tgcagagcca gccttcttat tcggccttga attgatcata tgcggattag    600
aaaaacaact taaatgtgaa agtggatcta tgaatccggg cggtgaacaa acaataatgg    660
aacaacccgc tcaacagcaa caacaacagc aacaacaaca gcagcaacag caacagcagg    720
cagcagttcc tcagcagcca ctcgacccat taacacaatc aactgcggaa acttggctct    780
ccattgcttc tttggcagaa acccttggtg atggcgacag ggccgcaatg gcatatgacg    840
ccactttaca gttcaatccc tcatctgcaa aggctttaac atctttggct cacttgtacc    900
gttccagaga catgttccaa agagctgcag aattatatga aagagcactt ttggtaaatc    960
ccgaactatc agatgtgtgg gctactttag gtcattgtta tctgatgctg gatgatctgc   1020
aaagagctta caatgcctat caacaggctc tctaccacct cagtaatccc aacgtaccga   1080
aattatggca tggaatcggc attctttatg acagatatgg ttcgctcgac tatgccgaag   1140
aagcttttgc caaagttttg gaattggacc ctcattttga aaaggcaaac gaaatttact   1200
tcagactagg tattatttat aaacatcagg gtaaatggtc acaagctttg gaatgcttca   1260
gatacattct ccctcaacct cctgctccct tgcaggagtg ggacatatgg tttcagttgg   1320
gtagtgtttt ggagagtatg ggagagtggc aaggtgcgaa ggaagcctac gagcatgtct   1380
tggctcaaaa tcaacatcat gccaaagtat tacaacaatt aggttgtctt tacggtatga   1440
gtaacgtaca attttatgac cctcaaaagg cattggatta tcttctaaag tcgttagaag   1500
cagatccctc cgatgccact acatggtatc atctcggtag agtgcatatg attagaacag   1560
attatactgc cgcatatgat gctttccaac aagctgttaa tagagattca agaaacccta   1620
tcttttggtg ctcaatcggt gttttatatt accaaatttc tcaatacaga gatgccttag   1680
acgcgtacac aagagccata agattaaatc cttatattag tgaagtttgg tacgatctag   1740
gtactcttta cgaaacttgt aacaaccaat tatctgacgc ccttgatgcg tataagcaag   1800
ctgcaagact ggacgtaaat aatgttcaca taagagaaag attagaagct ttaacaaagc   1860
agttagaaaa cccaggcaat ataaacaaat cgaacggtgc gccaacgaat gcctctcctg   1920
ccccacctcc tgtgatttta caacctacct tacaacctaa tgatcaagga aatcctttga   1980
acactagaat ttcagcccaa tctgccaatg ctactgcttc aatggtacaa caacagcatc   2040
ctgctcaaca aacgcctatt aactcttctg caacaatgta cagtaatgga gcttcccctc   2100
aattacaagc tcaagctcaa gctcaagctc aagcacaagc tcaagcacaa gcacaagctc   2160
aagcacaagc acaagcacaa gcgcaagcac aagcacaagc acaggcgcaa gcacaggcac   2220
aagcacaagc acaagcacat gcacaagcgc aagcacaagc acaagcaaag gcacaagcac   2280
aagcacaggc gcaggcacaa caacaacaac aacaacagca acaacaacaa caacaacaac   2340
aacaacaaca acaacaacaa caacaacaac aacaacaaca gcagcagcaa ttacagcccc   2400
taccaagaca acagctgcag caaaagggag tttctgtgca aatgttaaat cctcaacaag   2460
ggcaaccata tatcacacag ccaacagtca tacaagctca ccaactgcaa ccattttcta   2520
cacaagctat ggaacatccg caaagctctc aactgccacc tcaacagcaa caactacaat   2580
```

-continued ctgttcaaca tccacaacaa cttcaaggcc agcctcaagc ccaagctccc caacctttaa 2640
tccagcataa cgtggaacag aacgttttac ctcaaaagag atacatggaa ggtgcaatcc 2700
acactttagt agatgccgcc gtatccagta gcacccacac agagaataac acaaagtctc 2760
ctcgtcaacc aacccatgcc attccaacgc aagctcccgc aacaggaata acgaacgctg 2820
aaccacaggt aaagaagcaa aagttgaact ctccaaattc aaacatcaac aaattagtaa 2880
atactgctac ttccattgaa gaaaatgcaa aatctgaggt gagcaaccaa tcgccagcag 2940
tagtggagtc taataccaat aatacttcac aagaagaaaa acctgtaaaa gcaaactcaa 3000
taccttcagt aattggcgca caggaacctc cacaggaagc tagtcctgct gaagaagcta 3060
ccaaagcagc ttctgtttct ccttctacaa aaccgcttaa tacggaacca gagtcatcta 3120
gtgtccaacc aactgtatca tcagaaagtt caacaacaaa agcaaatgac caaagcactg 3180
ctgagactat agaactttct actgctactg ttcctgcaga agcaagccct gtagaagacg 3240
aagtaagaca gcattctaaa gaggaaaacg gcacaactga agcatctgca ccttctactg 3300
aagaggcgga gccagcagct tccagagatg ctgaaaaaca acaagatgaa accgctgcta 3360
caacgataac tgtaatcaaa cctactttgg aaacaatgga aacagtgaaa gaggaggcca 3420
aaatgcgtga ggaagaacaa acatctcaag aaaaatcccc acaggagaac acacttccaa 3480
gagaaaatgt agtaaggcaa gtggaagaag atgaaaacta cgacgactaa aggagacc 3538

<210> SEQ ID NO 77
<211> LENGTH: 321
<212> TYPE: DNA
<213> ORGANISM: Saccharomyces cerevisiae

<400> SEQUENCE: 77
ggtctcgtaa aaaagtttgc attcaaaaaa ttaatctact aatttataat caacgagaaa 60
tgttgtgtag ctcacaattc attcattatg ttgtggatac atatataaat aaagaaaagg 120
ctaaaaaaaa aggtgggtaa cgtgaattag gttatttttc atatatgcac atgtaaatat 180
atgcgtatat aaatatatta ttatttgtat cattacatac ttagaaatct attattgctt 240
aaaaggtttt cccgatgagc atatgtaata atattgggaa ttaaggtgca ttttcgtatc 300
cttcattgtg cctcggagac c 321

<210> SEQ ID NO 78
<211> LENGTH: 1292
<212> TYPE: DNA
<213> ORGANISM: Artificial Sequence
<220> FEATURE:
<223> OTHER INFORMATION: URA3 marker cassette

<400> SEQUENCE: 78
agcttttcaa ttcaattcat cattttttttt ttattctttt ttttgatttc ggtttctttg 60
aaattttttt gattcggtaa tctccgaaca gaaggaagaa cgaaggaagg agcacagact 120
tagattggta tatatacgca tatgtagtgt tgaagaaaca tgaaattgcc cagtattctt 180
aacccaactg cacagaacaa aaacctgcag gaaacgaaga taaatcatgt cgaaagctac 240
atataaggaa cgtgctgcta ctcatcctag tcctgttgct gccaagctat ttaatatcat 300
gcacgaaaag caaacaaact tgtgtgcttc attggatgtt cgtaccacca aggaattact 360
ggagttagtt gaagcattag gtcccaaaat ttgtttacta aaaacacatg tggatatctt 420
gactgatttt tccatggagg gcacagttaa gccgctaaag gcattatccg ccaagtacaa 480
ttttttactc ttcgaagaca gaaaatttgc tgacattggt aatacagtca aattgcagta 540

-continued

```
ctctgcgggt gtatacagaa tagcagaatg ggcagacatt acgaatgcac acggtgtggt    600

gggcccaggt attgttagcg gtttgaagca ggcggcagaa gaagtaacaa aggaacctag    660

aggccttttg atgttagcag aattgtcatg caagggctcc ctatctactg gagaatatac    720

taagggtact gttgacattg cgaagagcga caaagatttt gttatcggct ttattgctca    780

aagagacatg ggtggaagag atgaaggtta cgattggttg attatgacac ccggtgtggg    840

tttagatgac aagggagacg cattgggtca acagtataga accgtggatg atgtggtctc    900

tacaggatct gacattatta ttgttggaag aggactattt gcaaagggaa gggatgctaa    960

ggtagagggt gaacgttaca gaaaagcagg ctgggaagca tatttgagaa gatgcggcca   1020

gcaaaactaa aaaactgtat tataagtaaa tgcatgtata ctaaactcac aaattagagc   1080

ttcaatttaa ttatatcagt tattacccta tgcggtgtga aataccgcac agatgcgtaa   1140

ggagaaaata ccgcatcagg aaattgtaaa cgttaatatt ttgttaaaat tcgcgttaaa   1200

tttttgttaa atcagctcat tttttaacca ataggccgaa atcggcaaaa tcccttataa   1260

atcaaaagaa tagaccgaga tagggttgag tg                                 1292
```

<210> SEQ ID NO 79
<211> LENGTH: 1202
<212> TYPE: DNA
<213> ORGANISM: Artificial Sequence
<220> FEATURE:
<223> OTHER INFORMATION: NAT marker cassette

<400> SEQUENCE: 79

```
agatctgttt agcttgcctc gtccccgccg ggtcacccgg ccagcgacat ggaggcccag     60

aataccctcc ttgacagtct tgacgtgcgc agctcagggg catgatgtga ctgtcgcccg    120

tacatttagc ccatacatcc ccatgtataa tcatttgcat ccatacattt tgatggccgc    180

acggcgcgaa gcaaaaatta cggctcctcg ctgcagacct gcgagcaggg aaacgctccc    240

ctcacagacg cgttgaattg tccccacgcc gcgcccctgt agagaaatat aaaaggttag    300

gatttgccac tgaggttctt ctttcatata cttcctttta aaatcttgct aggatacagt    360

tctcacatca catccgaaca taaacaacca tgggtaccac tcttgacgac acggcttacc    420

ggtaccgcac cagtgtcccg ggggacgccg aggccatcga ggcactggat gggtccttca    480

ccaccgacac cgtcttccgc gtcaccgcca ccggggacgg cttcaccctg cgggaggtgc    540

cggtggaccc gcccctgacc aaggtgttcc ccgacgacga atcggacgac gaatcggacg    600

acggggagga cggcgacccg gactcccgga cgttcgtcgc gtacggggac gacggcgacc    660

tggcgggctt cgtggtcgtc tcgtactccg gctggaaccg ccggctgacc gtcgaggaca    720

tcgaggtcgc cccggagcac cgggggcacg gggtcgggcg cgcgttgatg gggctcgcga    780

cggagttcgc ccgcgagcgg ggcgccgggc acctctggct ggaggtcacc aacgtcaacg    840

caccggcgat ccacgcgtac cggcggatgg ggttcaccct ctgcggcctg gacaccgccc    900

tgtacgacgg caccgcctcg gacggcgagc aggcgctcta catgagcatg ccctgcccct    960

aatcagtact gacaataaaa agattcttgt tttcaagaac ttgtcatttg tatagttttt   1020

ttatattgta gttgttctat tttaatcaaa tgttagcgtg atttatattt tttttcgcct   1080

cgacatcatc tgcccagatg cgaagttaag tgcgcagaaa gtaatatcat gcgtcaatcg   1140

tatgtgaatg ctggtcgcta tactgctgtc gattcgatac taacgccgcc atccagtgtc   1200

ga                                                                  1202
```

-continued

```
<210> SEQ ID NO 80
<211> LENGTH: 468
<212> TYPE: DNA
<213> ORGANISM: Artificial Sequence
<220> FEATURE:
<223> OTHER INFORMATION: pGAL1 promoter

<400> SEQUENCE: 80

ctagtacgga ttagaagccg ccgagcgggt gacagccctc cgaaggaaga ctctcctccg     60

tgcgtcctcg tcttcaccgg tcgcgttcct gaaacgcaga tgtgcctcgc gccgcactgc    120

tccgaacaat aaagattcta caatactagc ttttatggtt atgaagagga aaaattggca    180

gtaacctggc cccacaaacc ttcaaatgaa cgaatcaaat taacaaccat aggatgataa    240

tgcgattagt tttttagcct tatttctggg gtaattaatc agcgaagcga tgatttttga    300

tctattaaca gatatataaa tgcaaaaact gcataaccac tttaactaat actttcaaca    360

ttttcggttt gtattacttc ttattcaaat gtaataaaag tatcaacaaa aaattgttaa    420

tatacctcta tactttaacg tcaaggagaa aaaaccccgg attctaga                 468
```